(12) United States Patent
Briesewitz et al.

(10) Patent No.: US 10,736,932 B2
(45) Date of Patent: Aug. 11, 2020

(54) SMALL MOLECULE RAS INHIBITORS

(71) Applicants: Roger Briesewitz, Columbus, OH (US); Dehua Pei, Columbus, OH (US); Punit Upadhyaya, Columbus, OH (US); Ohio State Innovation Foundation, Columbus, OH (US)

(72) Inventors: Roger Briesewitz, Columbus, OH (US); Dehua Pei, Columbus, OH (US); Punit Upadhyaya, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 391 days.

(21) Appl. No.: 15/312,593

(22) PCT Filed: May 19, 2015

(86) PCT No.: PCT/US2015/031624
§ 371 (c)(1),
(2) Date: Nov. 18, 2016

(87) PCT Pub. No.: WO2015/179434
PCT Pub. Date: Nov. 26, 2015

(65) Prior Publication Data
US 2017/0304383 A1 Oct. 26, 2017

Related U.S. Application Data

(60) Provisional application No. 62/000,984, filed on May 20, 2014, provisional application No. 62/039,753, filed on Aug. 20, 2014.

(51) Int. Cl.
| | |
|---|---|
| *A61K 47/68* | (2017.01) |
| *A61K 38/12* | (2006.01) |
| *C07K 7/64* | (2006.01) |
| *A61K 38/01* | (2006.01) |
| *C07K 16/28* | (2006.01) |
| *A61K 31/01* | (2006.01) |
| *A61K 39/395* | (2006.01) |
| *C07K 14/47* | (2006.01) |
| *A61K 38/00* | (2006.01) |
| *A61K 39/00* | (2006.01) |

(52) U.S. Cl.
CPC ............ *A61K 38/012* (2013.01); *A61K 31/01* (2013.01); *A61K 38/12* (2013.01); *A61K 39/3955* (2013.01); *A61K 47/6811* (2017.08); *A61K 47/6849* (2017.08); *C07K 7/64* (2013.01); *C07K 14/4703* (2013.01); *C07K 16/2863* (2013.01); *A61K 38/00* (2013.01); *A61K 2039/585* (2013.01); *A61K 2039/627* (2013.01); *A61K 2300/00* (2013.01)

(58) Field of Classification Search
CPC ....... A61K 38/12; A61K 47/6811; C07K 7/64
See application file for complete search history.

(56) References Cited

U.S. PATENT DOCUMENTS

| | | | |
|---|---|---|---|
| 6,921,531 | B2 | 7/2005 | Briesewitz et al. |
| 7,390,784 | B2 | 6/2008 | Briesewitz et al. |
| 7,393,529 | B2 | 7/2008 | Krah et al. |
| 2008/0249124 | A1 | 10/2008 | Gu et al. |
| 2009/0203671 | A1 | 8/2009 | Glaser et al. |
| 2013/0164317 | A1 | 6/2013 | Yousef et al. |
| 2017/0304383 | A1 | 10/2017 | Briesewitz et al. |

FOREIGN PATENT DOCUMENTS

| | | | |
|---|---|---|---|
| CA | 2089747 A1 * | 4/1992 | ........... C07K 14/582 |
| WO | WO-2005/009457 | 2/2005 | |
| WO | WO-2010/101622 | 9/2010 | |
| WO | WO-2012/174489 A2 | 12/2012 | |

OTHER PUBLICATIONS

Chabard et al, ERK implication in cell cycle regulation. Biochim Biophys Acta. Aug.;1773(8):1299-310(2007).
Dhanasekaran, et al, Scaffold proteins of MAP-kinase modules. Oncogene, 26, pp. 3185-3202(2007).
International Search Report and Written Opinion for PCT International Patent Application No. PCT/US2015/031624, dated Aug. 11, 2015.
Moro, et al, Constitutive activation of MAPK/ERK inhibits prostate cancer cell proliferation through upregulation of BRCA2. Int J Oncol. Jan.;30(1):217-24 (2007).
Restriction Requirement for U.S. Appl. No. 14/126,343, dated Sep. 22, 2014.
Tamaki et al. (2011), "Novel gratisin derivatives with high antimicrobial activity and low hemolytic activity", Bioorganic & Medicinal Chemistry Letters, 21(1): 440-443.
Upadhyaya P. et al. (2015), "Inhibition of Ras Signaling by Blocking Ras-Effector Interactions With Cyclic Peptides", Angewandte Chemie International Edition, May 7, 2015, vol. 127, pp. 7712-7716.

(Continued)

*Primary Examiner* — James H Alstrum-Acevedo
*Assistant Examiner* — Kaipeen E Yang
(74) *Attorney, Agent, or Firm* — Foley & Lardner LLP

(57) ABSTRACT

Disclosed herein are novel compounds that are Ras inhibitors. Also disclosed are compositions comprising the compounds and methods of using the compounds in treating various diseases. In another aspect, provided is an antibody-drug-conjugate comprising an antibody conjugated with a compound described herein. In still another aspect, provided is a pharmaceutical composition comprising a compound or antibody-drug-conjugate described herein. In a further aspect, provided is method of treating a cancer comprising administering a therapeutically effective amount of a compound or antibody-drug-conjugate described herein to a patient in need thereof.

12 Claims, 12 Drawing Sheets

(56) References Cited

OTHER PUBLICATIONS

Non-Final Office Action for U.S. Appl. No. 14/126,343, dated Feb. 26, 2015.
Notice of Allowance for U.S. Appl. No. 14/126,343, dated Oct. 7, 2015.
Restriction Requirement for U.S. Appl. No. 14/997,302, dated Sep. 13, 2016.
Villalona-Calero (2010), "Challenging Targets in Lung Cancer", Lung Cancer Conference, The Ohio State University, p. 26-28.
Wu X. et al. (2013), "Inhibition of Ras-Effector Interaction by Cyclic Peptides", MedChemComm, Feb. 1, 2013, vol. 4, No. 1, pp. 378-382.
Prenen, et al., "New Strategies for Treatment of KRAS Mutant Metastatic Colorectal Cancer", Clinical Cancer Research, Published Online First May 11, 2010.
U.S. Office Action dated Jan. 17, 2018, from U.S. Appl. No. 15/312,590.
U.S. Office Action dated Mar. 1, 2017, from U.S. Appl. No. 14/997,302.
U.S. Office Action dated Nov. 2, 2017, from U.S. Appl. No. 14/997,302.
Wei, et al., "K-Ras mutation-mediated IGF-1-induced feedback ERK activation contributes to the rapalog resistance in pancreatic ductal adenocarcinomas", Cancer Letters 322 (2012) 58-69.
Wu, et al.,"Inhibition of Ras-effector interactions by cyclic peptidest", Med. Chem. Commun., 2013, 4, 378-382.

* cited by examiner

Cyclorasin 3A: cyclo(Arg-Arg-nal-Arg-Fpa-asn-nal-MeLeu-Gln)

Cyclorasin 4A: cyclo(Arg-Arg-nal-Arg-Fpa-Gly-Fpa-ala-ala-Gln)

Cyclorasin 5A: cyclo(Arg-Arg-nal-Arg-Fpa-nle-val-glu-Ile-val-Gln)

Cyclorasin 6A: cyclo(Arg-Arg-nal-Arg-Fpa-nle-phe-Gly-His-Tyr-Gln)

Cyclorasin 7A: cyclo(Arg-Arg-nal-Arg-Fpa-Arg-Tyr-val-Fpa-Gln)

Cyclorasin 8A: cyclo(Arg-Arg-nal-Arg-Fpa-Phg-Tyr-ser-phe-Gln)

Cyclorasin 9A: cyclo(Arg-Arg-nal-Arg-Fpa-nle-ser-Trp-Thr-ala-Gln)

Cyclorasin 10A: cyclo(Arg-Arg-nal-Arg-Fpa-nle-Tyr-asn-ala-Ile-Gln)

Cyclorasin 11A: cyclo(Arg-Arg-nal-Arg-Fpa-ala-Fpa-Thr-nal-Gln)

Cyclorasin 12A: cyclo(Arg-Arg-nal-Arg-Fpa-Arg-Trp-Arg-ala-Gln)

SMALL MOLECULE RAS INHIBITORS

CROSS-REFERENCE TO RELATED APPLICATIONS

This application is a national stage application under 35 U.S.C. § 371 of International Application No. PCT/US2015/031624, filed on May 19, 2015, which in turn claims priority under 35 U.S.C. § 119(e) of U.S. Provisional Application Nos. 62/000,984, filed May 20, 2014, and 62/039,753, filed Aug. 20, 2014, the content of each of which is incorporated by reference in its entirety into the current disclosure.

STATEMENT OF GOVERNMENT SUPPORT

This invention was made with government support under Grant Nos. CA132855 and GM062820 awarded by the National Institutes of Health. The government has certain rights in the invention.

BACKGROUND

Ras genes are frequently activated in human cancers. For example, K-Ras is a member of the small guanosine triphosphate (GTP) binding protein family which constitutes over 100 members. Wild-type K-Ras oscillates between an active, GTP-bound form and an inactive guanosine diphosphate (GDP) form. The GTP-bound form has a distinct conformation that promotes its interaction with multiple effector proteins via its Switch I and Switch II regions. 30% of all solid tumors show activating point mutations in K-Ras. K-Ras mutants are insensitive to down regulation by GAP-mediated hydrolysis of bound GTP. As a result, mutant K-Ras is "frozen" in its activated form which results in constitutive signaling into proliferation and survival pathways. K-Ras point mutations are usually found at codons 12, 13 and 61 and less frequently at codons 59 and 63. Typical point mutations at codon 12 replace a glycine by aspartate or valine. Transgenic mouse models have demonstrated that expression of mutated K-Ras by itself or in combination with the introduction of other oncogenic lesions can promote cancer. Similarly, it was shown that cancer cells undergo apoptosis if oncogenic K-Ras is down regulated by RNA interference. These data strongly suggest that inhibition of oncogenic K-Ras may have therapeutic benefits in cancer patients. K-Ras is farnesylated and located at the inner leaflet of the plasma membrane. In recent years the pharmaceutical industry has attempted to target oncogenic K-Ras proteins by disrupting its subcellular localization with farnesyl transferase inhibitors (FTIs). However, in clinical trials FTIs have proved largely ineffective in pancreatic and other cancers, possibly because the loss of FT activity is compensated for by geranyl-geranyl transferase (Sebti, S. M. & Adjei, A. A. Farnesyltransferase inhibitors, *Seminars in Oncology,* 31:28-39 (2004)).

There is a need for the development of small molecule therapeutic agents that inhibit Ras.

SUMMARY

Disclosed herein are small molecule Ras inhibitory compounds, compositions, and uses thereof.

In one aspect, provided herein are compounds of Formula A

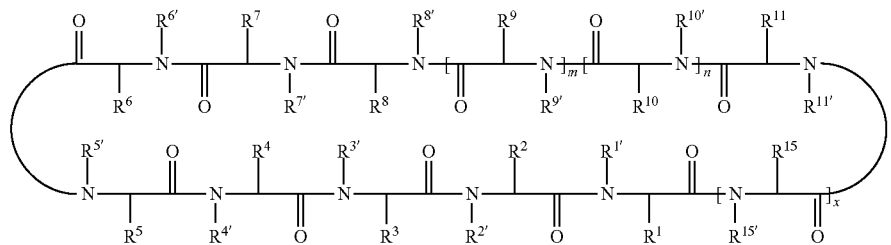

or a tautomer, a pharmaceutically acceptable salt and/or a solvate thereof;
wherein
$R^1$, $R^2$, $R^4$, $R^6$, $R^7$, $R^8$, $R^{10}$, $R^{11}$ and each $R^{15}$ are independently H, $C_1$-$C_6$ alkyl, substituted $C_1$-$C_6$ alkyl, phenyl, or substituted phenyl, wherein at least two of $R^1$, $R^2$, $R^4$, $R^6$, $R^7$, $R^8$, $R^{10}$, $R^{11}$ and $R^{15}$ are $C_1$-$C_6$ alkyl substituted with NHC(=NH)NH$_2$ and no four consecutive $R^1$, $R^2$, $R^4$, $R^6$, $R^7$, $R^8$, $R^{10}$, $R^{11}$ and $R^{15}$ are (CH$_2$)$_3$NHC(=NH)NH$_2$;
$R^3$ and $R^5$ are independently L-R, wherein L is covalent bond, $C_1$-$C_6$ alkylene, (CH$_2$)$_s$C(O)NH or (CH$_2$)$_s$NHC(O), and R is aryl, substituted aryl, heteroaryl or substituted heteroaryl;
$R^9$ is $C_1$-$C_6$ alkyl or $C_1$-$C_6$ alkyl substituted with OH;
$R^{1'}$, $R^{2'}$, $R^{3'}$, $R^{4'}$, $R^{5'}$, $R^{6'}$, $R^{7'}$, $R^{8'}$, $R^{9'}$, $R^{10'}$, $R^{11'}$ and each $R^{15'}$ are independently H or methyl;
x is 0, 1, 2, 3 or 4;
s is 0, 1, 2, or 3;
m is 0 or 1; and
n is 0 or 1.

In one aspect, provided herein are compounds of Formula I, II or III:

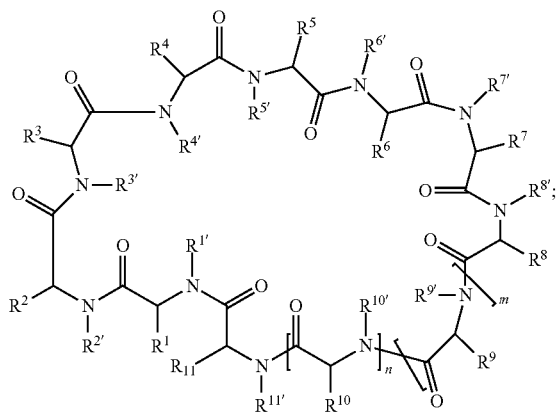

or a tautomer, a pharmaceutically acceptable salt and/or a solvate thereof;

wherein $R^1$, $R^2$, $R^4$, $R^6$, $R^7$, $R^8$, $R^{10}$ and $R^{11}$ are independently H, $C_1$-$C_6$ alkyl, substituted $C_1$-$C_6$ alkyl, phenyl, or substituted phenyl, wherein at least two of $R^1$, $R^2$, $R^4$, $R^6$, $R^7$, $R^8$, $R^{10}$ and $R^{11}$ are $C_1$-$C_6$ alkyl substituted with NHC(=NH)NH$_2$ and $R^1$, $R^2$, $R^{10}$, and $R^{11}$ cannot be all (CH$_2$)$_3$NHC(=NH)NH$_2$;

$R^3$ and $R^5$ are independently L-R, wherein L is covalent bond, $C_1$-$C_6$ alkylene, (CH$_2$)$_s$C(O)NH or (CH$_2$)$_s$NHC(O), and R is aryl, substituted aryl, heteroaryl or substituted heteroaryl;

$R^9$ is $C_1$-$C_6$ alkyl or $C_1$-$C_6$ alkyl substituted with OH;

$R^{1'}$, $R^{2'}$, $R^{3'}$, $R^{4'}$, $R^{5'}$, $R^{6'}$, $R^{7'}$, $R^{8'}$, $R^{9'}$, $R^{10'}$ and $R^{11'}$ are independently H or methyl;

s is 0, 1, 2, or 3;

m is 0 or 1; and n is 0 or 1.

In one aspect, provided herein are compounds of Formula IB, IIB, IIIB, IVB, VB or VIB:

-continued

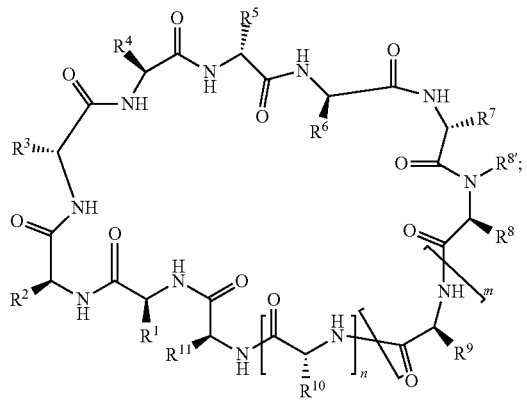

IVB

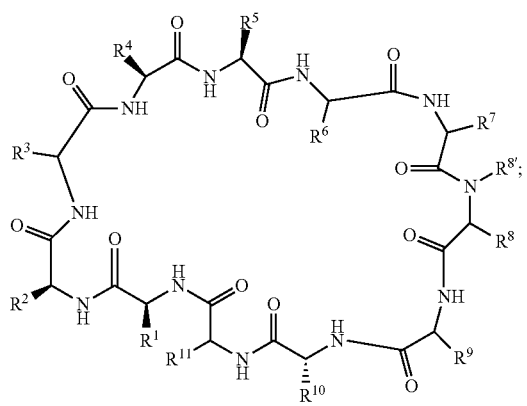

VB

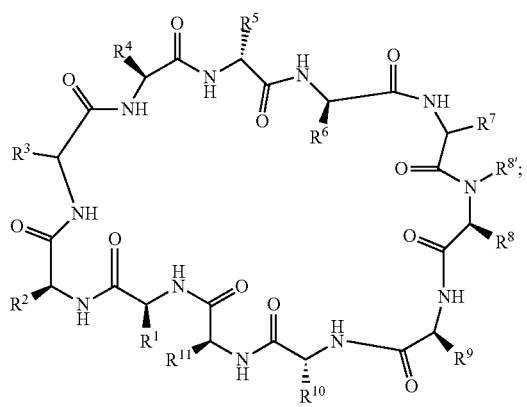

VIB or a tautomer, a pharmaceutically acceptable salt and/or a solvate thereof;
wherein
$R^1$, $R^2$, $R^4$, $R^6$, $R^7$, $R^8$, $R^{10}$ and $R^{11}$ are independently H, $C_1$-$C_6$ alkyl, substituted $C_1$-$C_6$ alkyl, phenyl, or substituted phenyl, wherein at least two of $R^1$, $R^2$, $R^4$, $R^6$, $R^7$, $R^8$, $R^{10}$ and $R^{11}$ are $C_1$-$C_6$ alkyl substituted with $NHC(=NH)NH_2$ and $R^1$, $R^2$, $R^{10}$, and $R^{11}$ cannot be all $(CH_2)_3NHC(=NH)NH_2$;
$R^3$ and $R^5$ are independently L-R, wherein L is covalent bond, $C_1$-$C_6$ alkylene, $(CH_2)_sC(O)NH$ or $(CH_2)_sNHC(O)$, and R is aryl, substituted aryl, heteroaryl or substituted heteroaryl;
$R^9$ is $C_1$-$C_6$ alkyl or $C_1$-$C_6$ alkyl substituted with OH;
$R^{8'}$ is hydrogen or methyl;
s is 0, 1, 2, or 3;
m is 0 or 1; and
n is 0 or 1.

In another aspect, provided is an antibody-drug-conjugate comprising an antibody conjugated with a compound described herein.

In still another aspect, provided is a pharmaceutical composition comprising a compound or antibody-drug-conjugate described herein.

In a further aspect, provided is method of treating a cancer comprising administering a therapeutically effective amount of a compound or antibody-drug-conjugate described herein to a patient in need thereof.

In a still further aspect, provided is a method of treating a disease mediated at least in part by Ras, which method comprises administering a therapeutically effective amount of a compound or antibody-drug-conjugate described herein to a patient in need thereof.

In a still further aspect, provided is a method of treating a disease mediated at least in part by epidermal growth factor receptor (EGFR), which method comprises administering a therapeutically effective amount of a compound or antibody-drug-conjugate described herein to a patient in need thereof.

In a still further aspect, provided is a method of treating a disease resistant to, or a disease likely resistant to, an EGFR inhibitor, which method comprises administering an effective amount of a compound or antibody-drug-conjugate described herein to a patient in need of the treatment. In one aspect, the disease is a cancer that is resistant to an EGFR inhibitor.

In a still further aspect, provided is a method of treating a patient in need of a Ras inhibitor, which method comprises determining the amount of phospho-Akt, phospho-Mek and/or phospho-Erk in a cell of the patient;
administering a therapeutically effective amount of a compound or antibody-drug-conjugate described herein to the patient;
determining the amount of phospho-Akt, phospho-Mek and/or phospho-Erk in a cell of the patient after the administration; and
continuing to administer a therapeutically effective amount of the compound or antibody-drug-conjugate to the patient if a decrease in phospho-Akt, phospho-Mek and/or phospho-Erk is detected.

In a still further aspect, provided is a method of inhibiting phosphorylation of Akt, Mek and/or Erk, which method comprises contacting a cell in need of inhibition of Akt, Mek and/or Erk with an effective amount of a compound or antibody-drug-conjugate described herein. The contacting can be in vitro or in vivo.

In a further aspect, this disclosure provides kits for the therapeutic administration of the compounds and compositions of this disclosure. The kits comprise a composition or compound and instructions for use. In a further aspect, the kit also comprises diagnostic reagents and/or instructions for determining the genotype of a patient biopsy that may guide therapeutic use of the compounds and compositions as disclosed herein.

These and other aspects are further described in the text that follows.

The fold of reduction in the Ras inhibitory activity upon replacing each residue of Cyclorasin 9A with alanine (or D-alanine) is shown in boldfaced figures next to the residue. Amino acid residues derived from compound 12, library screening, and individual synthesis are shown in black, red and blue colors, respectively, whereas the residue numbering in Cyclorasin 9A1 to 9A54 is shown in green color.

Figure 2:
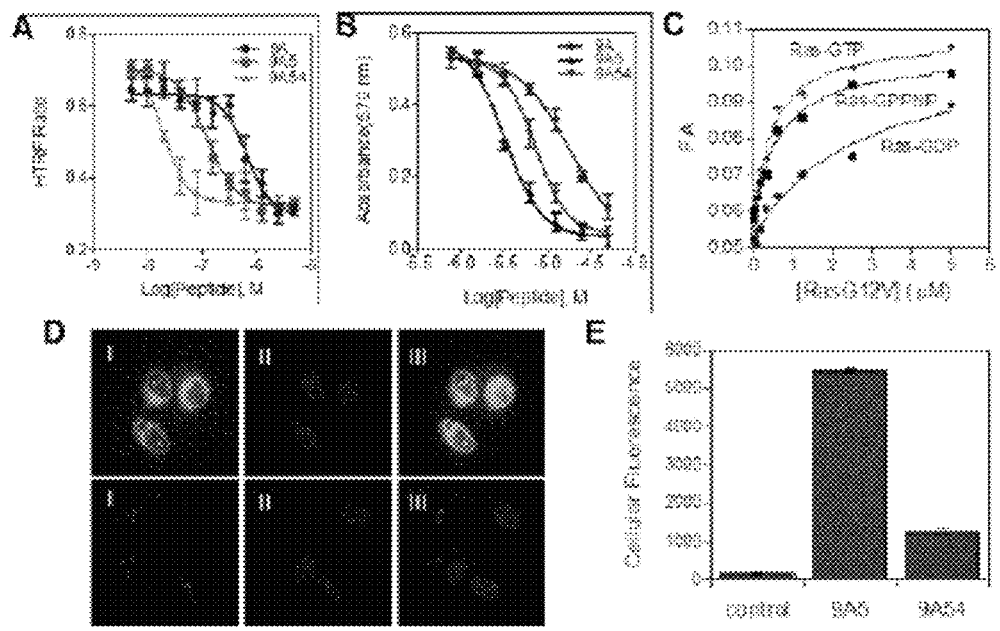

FIG. 2A shows inhibition of Ras-Raf RBD interaction by Cyclorasin 9A, 9A5 and 9A54 as analyzed by the HTRF assay. FIG. 2B shows anti-proliferative activity of 9A, 9A5 and 9A54 against H1299 lung cancer cells as determined by the MTT assay. FIG. 2C shows binding of FITC-labeled Cyclorasin 9A5 to Ras-GTP, Ras-GDP, and Ras-GPPNP as analyzed by FA. FIG. 2D shows live-cell confocal microscopic images of A549 cells after treatment with 10 µM FITC-labeled 9A5 (top panel) or 9A54 (bottom panel) for 15 min followed by 5 µM nuclear stain DRAQ5 for 10 min. I, FITC fluorescence; II, nuclear stain with DRAQ5; III, merge of I and II. FIG. 2E shows a comparison of the mean fluorescence intensity of A549 cells after treatment with 10 µM FITC-labeled 9A5 or 9A54 as determined by fluorescence-activated cell sorting. Control, untreated cells.

Figure 3:
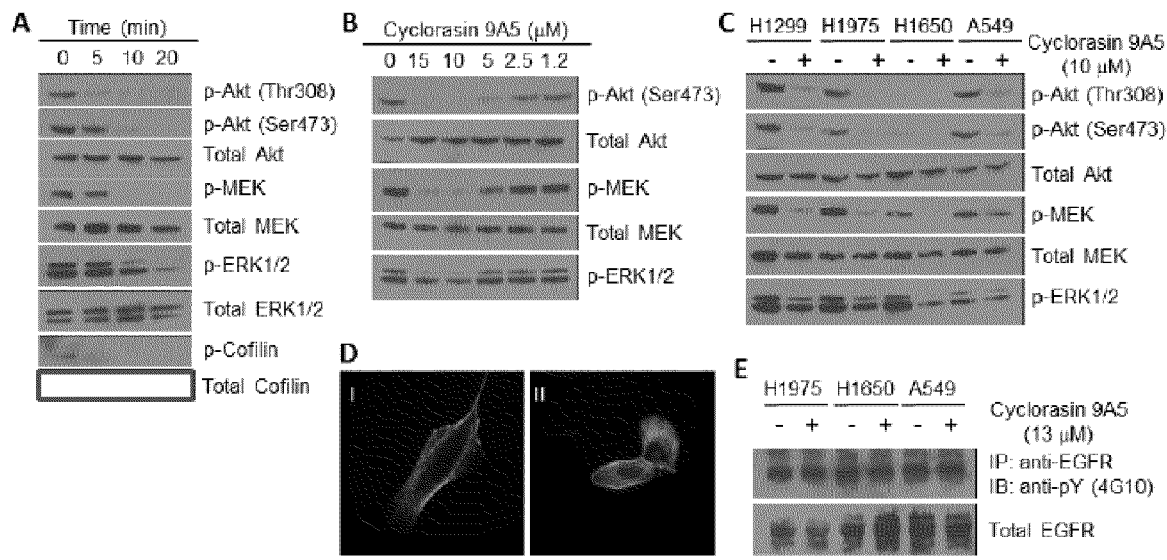

FIG. 3A shows the Western blots illustrating time-dependent inhibition of the phosphorylation of signaling proteins downstream of Ras (Akt, Mek, and Erk) as well as Rac and Rho (cofilin) in H1299 cells by Cyclorasin 9A5 (13 µM). FIG. 3B shows dose-dependent inhibition of Ras signaling in H1299 cells by Cyclorasin 9A5 (10 min treatment). FIG. 3C shows varying sensitivities of different lung cancer cell lines to Cyclorasin 9A5 (treatment with 10 µM peptide for 10 min) as monitored by Akt, Mek, and Erk phosphorylation. FIG. 3D shows confocal microscopic images of A549 cells untreated (I) or treated with 10 µM Cyclorasin 9A5 for 15 min (II), fixed with formaldehyde, and then stained with phalloidin-FITC (100 nM). FIG. 3E shows immunoblot analysis showing that Cyclorasin 9A5 (13 µM) had no effect on EGF receptor phosphorylation.

Figure 4:
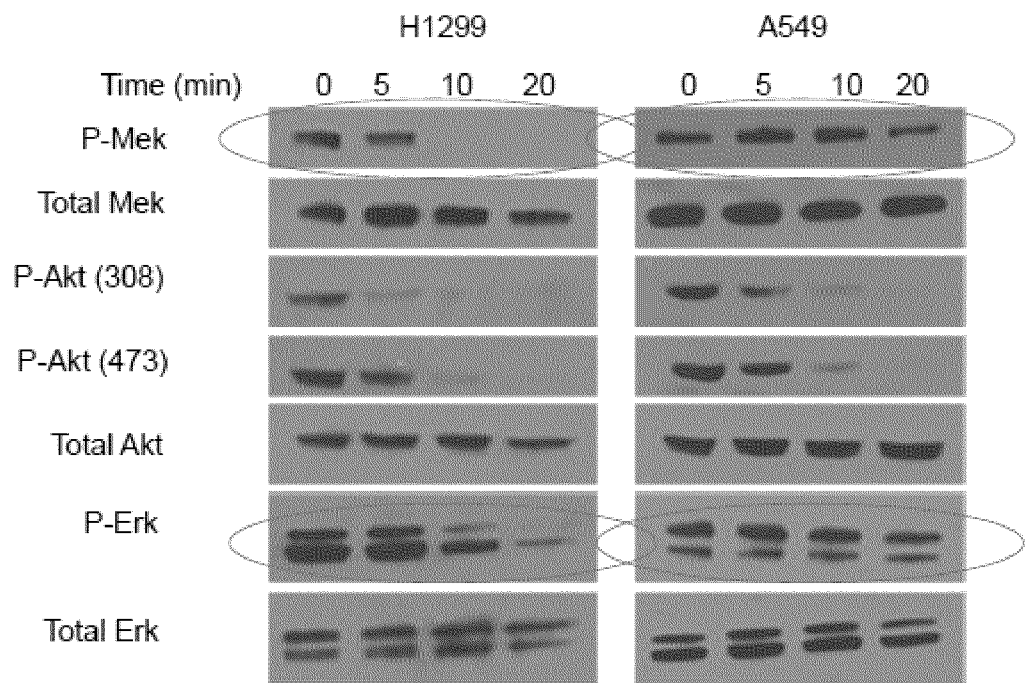

FIG. 4 shows the time course of treatment of H1299 or A549 cell lines with Compound 9A5, which demonstrates that some cancer cells like A549 are resistant to Ras inhibitors because the MAPK pathway is not downregulated after exposure to the drug.

Figure 5:
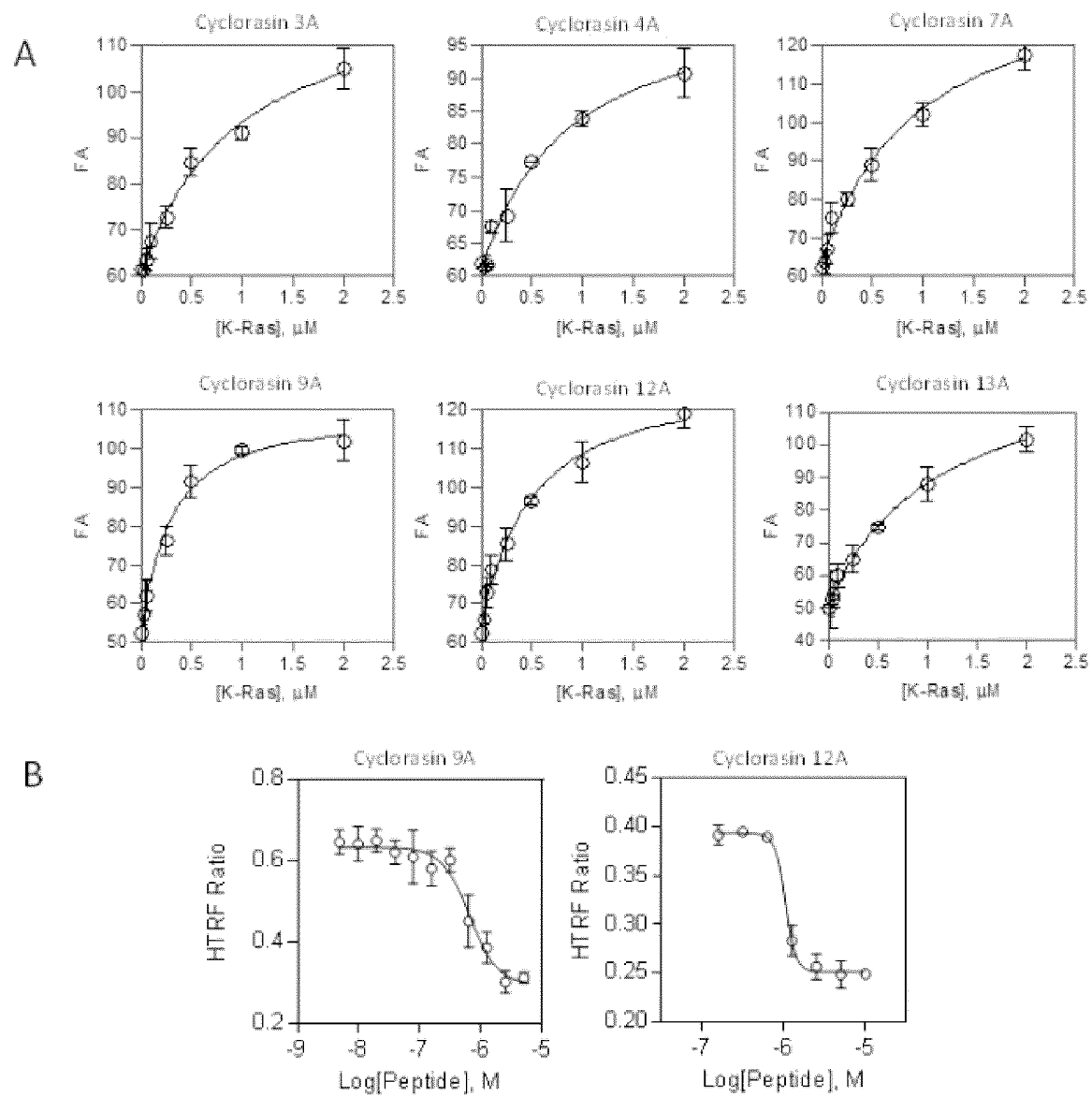

FIG. 5A shows binding of resynthesized cyclic peptide hits 3A, 4A, 7A, 9A, 12A, and 13A identified from the 2nd-generation library to K-Ras(G12V) as analyzed by FA. The peptides were synthesized with a lysine linker added to the invariant Gln side chain and labeled at the lysine side chain with FITC. FIG. 5B shows HTRF assay showing the inhibition of Ras(G12V)-Raf RBD interaction by Cyclorasin 9A and 12A (unlabeled). All experiments were carried out in triplicates and the error bars indicate standard deviation from three independent experiments. The sequences and binding affinities of the peptides are listed in Tables 1 and 2.

Figure 6:
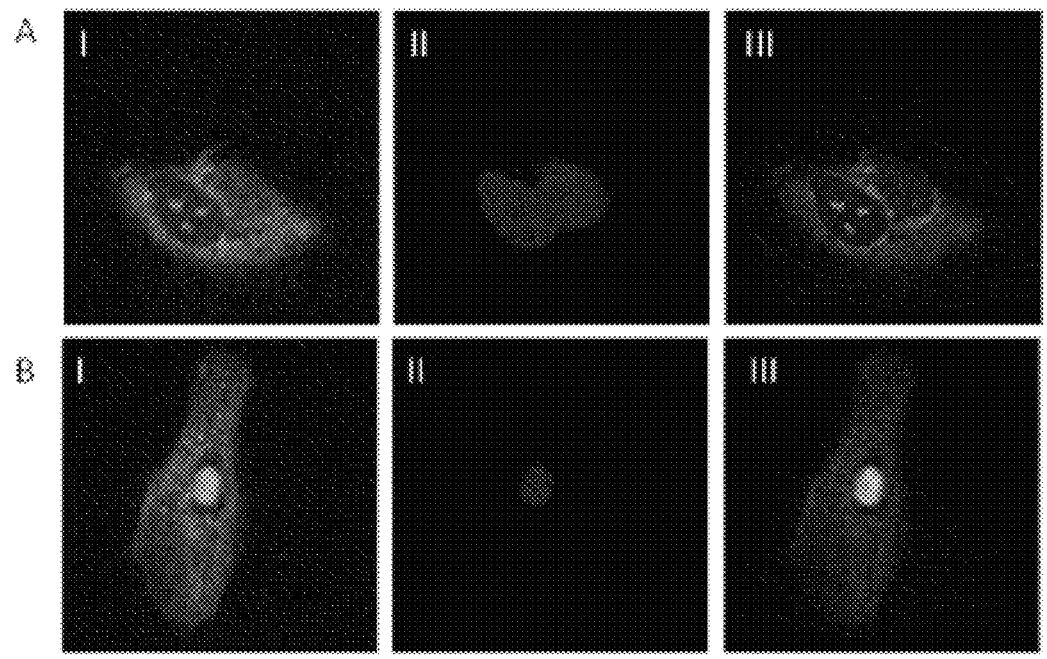

FIGS. 6A-6B show live-cell confocal microscopic images of A549 lung cancer cells treated with 10 µM FITC-labeled Cyclorasin 9A (FIG. 6A) and 12A (FIG. 6B) for 1.5 h. I, Green fluorescence of FITC-labeled peptide; II, nuclear stain with Hoescht 33342; and III, Merged images of I and II.

Figure 7:
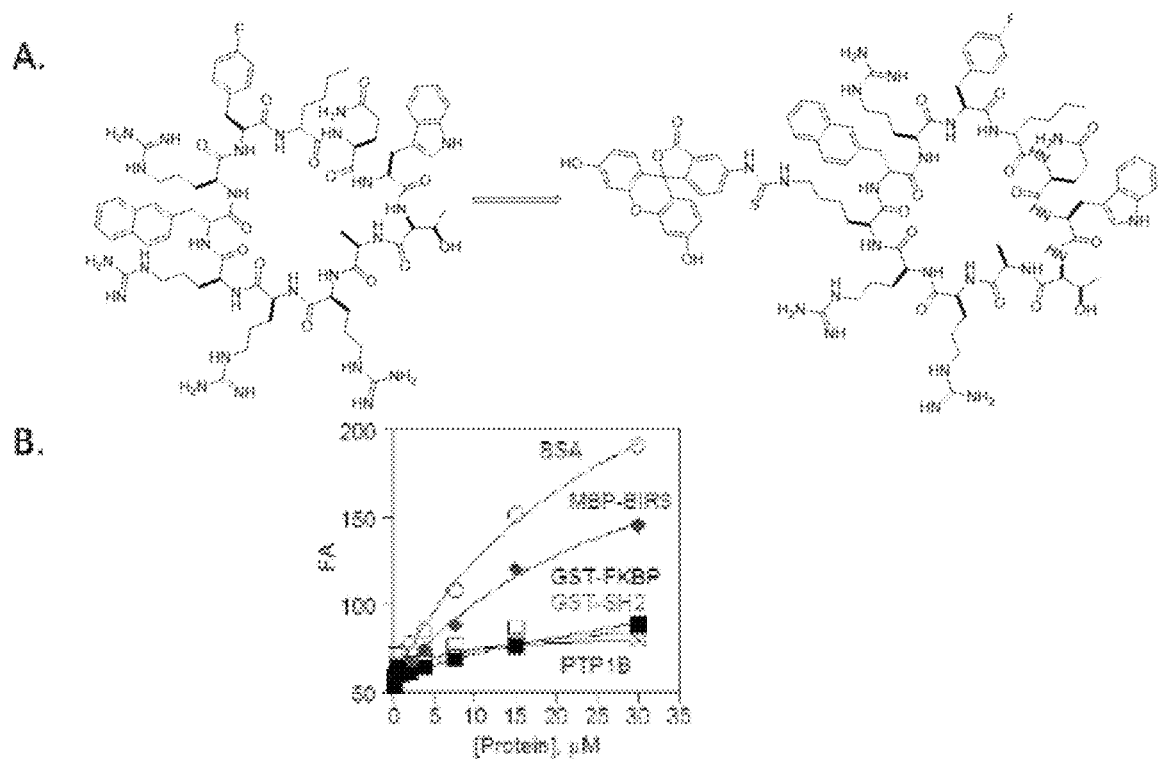

FIG. 7A shows structures of unlabeled and FITC-labeled Cyclorasin 9A5. Note the replacement of an arginine at position 6 with a lysine for FITC labeling. This modification reduced the binding affinity of Cyclorasin 9A5 for K-Ras by 3-4-fold. Labeling with FITC at other positions (e.g., Gln1, Arg4, or Arg7) abolished or greatly reduced its binding affinity to K-Ras. FIG. 7B shows binding of FITC-labeled Cyclorasin 9A5 to 5 arbitrarily selected control proteins BSA ($K_D$=31 µM), MBP-XIAP BIR3 ($K_D$=30 µM), GST-FKBP, GST-SH2, and PTP1B.

Figure 8:
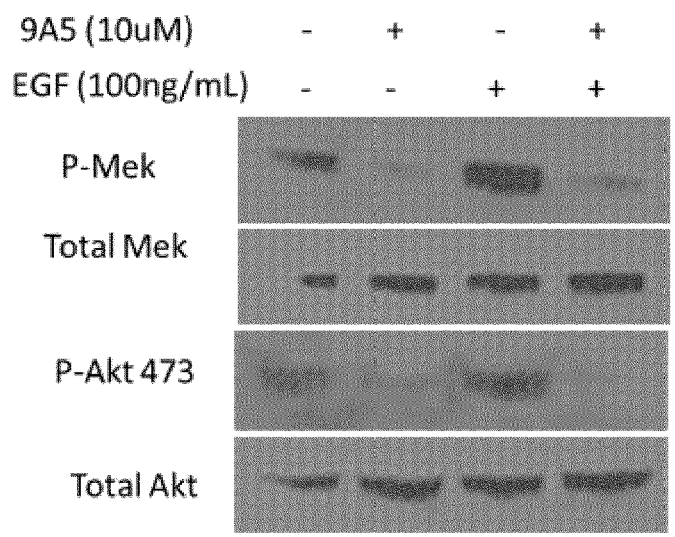

FIG. 8 shows Western blots showing the inhibition of Akt and Mek phosphorylation in H1299 cells by Cyclorasin 9A5 (10 µM for 10 min) in the presence and absence of EGF stimulation (100 ng/mL).

Figure 9:
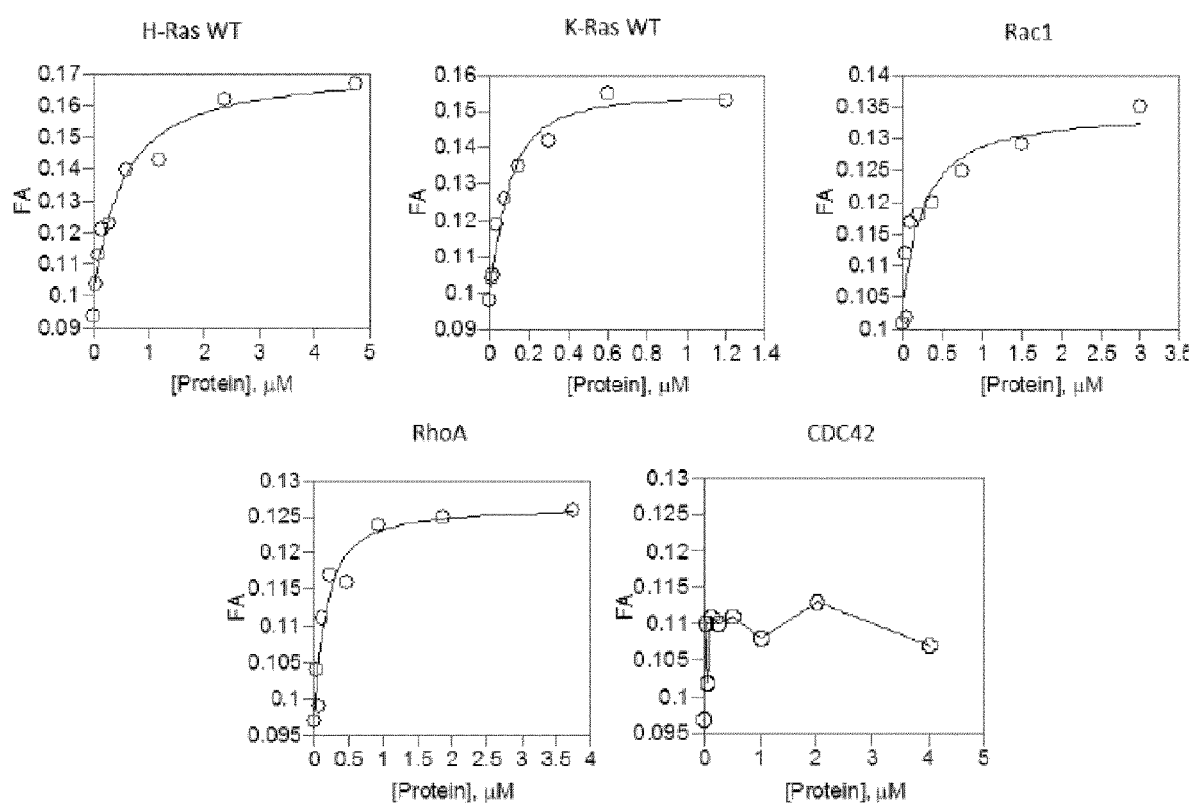

FIG. 9 shows FA analysis of the binding of FITC-labeled Cyclorasin 9A5 to purified recombinant H-Ras(WT), K-Ras (WT), Rac1, RhoA and CDC42.

FIGS. 10-22 show sequence determination of 13 positive hits by PED-MS. Positive beads derived from library screening were subjected to 10 cycles of PED and the peptides were released from each bead using CNBr and analyzed by MALDI-TOF MS. The peptide sequences corresponding to the randomized region of the peptide library are underlined.

DETAILED DESCRIPTION

Definitions

The practice of the present invention will employ, unless otherwise indicated, conventional techniques of tissue culture, immunology, molecular biology, microbiology, cell biology and recombinant DNA, which are within the skill of the art. See, e.g., Sambrook et al., (1989) Molecular Cloning: A Laboratory Manual, 2nd edition; Ausubel et al., eds. (1987) Current Protocols In Molecular Biology; MacPherson, B. D. Hames and G. R. Taylor eds., (1995) PCR 2: A Practical Approach; Harlow and Lane, eds. (1988) Antibodies, A Laboratory Manual; Harlow and Lane, eds. (1999) Using Antibodies, a Laboratory Manual; and R. I. Freshney, ed. (1987) Animal Cell Culture.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

The term "about" when used with numerical designations, e.g., pH, temperature, time, concentration, and molecular weight, including ranges, indicates approximations (+) or (−) 10%, 5%, or 1%, as appropriate.

As used in the specification and claims, the singular form "a," "an" and "the" include plural references unless the context clearly dictates otherwise.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps. Embodiments defined by each of these transition terms are within the scope of this invention.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not. For example, the term "optionally substituted" when describing a moiety means that the moiety is unsubstituted (i.e., all substituents are hydrogen) or substituted (i.e., at least one of the hydrogen atoms of the moiety is replaced by a non-hydrogen substituent).

As used herein, the term "ligand" refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates. The terms "natural ligand" and "cognate ligand" are used interchangeably, and refer to a naturally occurring ligand, found in nature, which binds to a receptor. For example, cognate ligands of Ras include Raf and PI3K.

As used herein, the terms "effective amount" and "amount effective" refer to an amount that is sufficient to achieve the desired result or to have an effect on an undesired condition.

As used herein, "$EC_{50}$," refers to the concentration of a substance (e.g., a compound or a drug) that is required for 50% activation or enhancement of a biological process, or component of a process. For example, $EC_{50}$ can refer to the concentration of agonist that provokes a response halfway between the baseline and maximum response in an appropriate assay of the target activity.

As used herein, "$IC_{50}$," refers to the concentration of a substance (e.g., a compound or a drug) that is required for 50% inhibition of a biological process, or component of a process. For example, $IC_{50}$ refers to the half maximal (50%) inhibitory concentration (IC) of a substance as determined in a suitable assay.

A "composition" is also intended to encompass a combination of active agent and a carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term "pharmaceutically acceptable carrier" (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

As used herein, the term "patient" or "subject" intends an animal, a mammal or in particular a human. For the purpose of illustration only, a mammal includes but is not limited to a human, a feline, a canine, a simian, a murine, a bovine, an equine, a porcine or an ovine.

In the context of chemical formulas, the symbol "—" means a single bond, "=" means a double bond, and "≡" means triple bond. The symbol "-----" represents an optional bond, which if present is either single or double. The symbol "⚌" represents a single bond or a double bond. For example, the structure

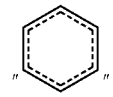

includes the structures

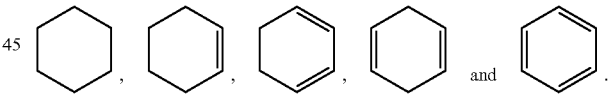

As will be understood by a person of skill in the art, no one such ring atom forms part of more than one double bond. The symbol "∿" when drawn perpendicularly across a bond indicates a point of attachment of the group.

Embraced herein and unless otherwise indicated, where applicable, are permissible isomers such as tautomers, racemates, enantiomers, diastereomers, atropisomers, configurational isomers of double bonds (E- and/or Z-), cis- and trans-configurations in ring substitution patterns, and isotopic variants, pure isomers or a mixture of the isomers, such as a mixture of enantiomers. A 50:50 mixture of enantiomers is referred to as a racemic mixture.

In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory, and (+) or d meaning that the compound is dextrorotatory. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula.

The symbol "—◾" means a single bond where the group attached to the thick end of the wedge is "out of the page." The symbol "⦙⦙⦙⦙⦙" means a single bond where the group attached to the thick end of the wedge is "into the page". The symbol "∿∿∿" when used to represent a single bond means that the conformation (e.g., either R or S) or the geometry (e.g., either E or Z) of the bond is undefined, and can be either or both.

It is also appreciated that certain compounds described herein can be present as an equilibrium of tautomers. For example, ketones with an α-hydrogen can exist in an equilibrium of the keto form and the enol form.

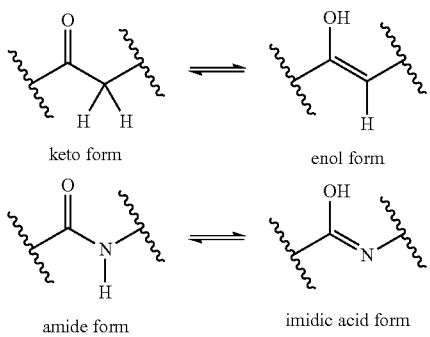

Unless stated to the contrary, the invention includes all such possible tautomers of a compound.

The symbol "$(C_n)$" defines the number (n) of carbon atoms in a group. "$C_{n-m}$" defines the range of the number of carbon atoms in a group. For example, $C_3$ alkyl defines an alkyl group having 3 carbon atoms and $C_{3-8}$ cycloalkyl defines a cycloalkyl group having 3 to 8 carbon atoms.

A "residue" of a chemical species refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to a —CO(CH$_2$)$_8$CO— moiety in the polyester, regardless of whether the residue is obtained by reacting sebacic acid or an ester thereof to obtain the polyester.

An "amino acid residue" refers to the moiety of an amino acid resulting from formation of an amide bond with another compound having an acid or an amino group. For example, when an alanine (Ala) and an aspartic acid (Asp) forms an amide bond to form the dipeptide NH$_2$-Ala-Asp-COOH:

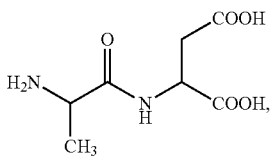

then

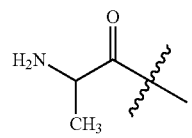

is called an analine residue, and

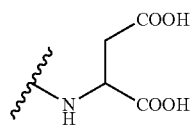 [SMILES: *NC(CC(=O)O)C(=O)O]

is called an aspatic acid residue. Similarly, in the tripeptide NH$_2$-Ala-Asp-Gly-COOH:

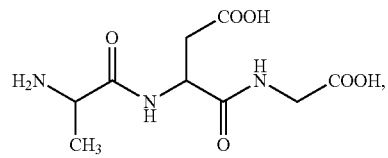

the moiety

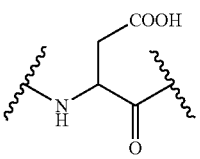 [SMILES: *NC(CC(=O)O)C(*)=O]

is called an aspartic acid residue.

An "amino acid" refers to a compound having at least one amino group (—NHR$^a$, wherein R$^a$ is hydrogen, alkyl or substituted alkyl, or R$^a$ may optionally cyclize with the nitrogen atom, such in proline) and at least one carboxyl group (—COOH). Amino acids include naturally occurring amino acids and non-naturally occurring amino acids, α-amino acids, β-amino acids, etc. Naturally occurring L-amino acids include:

| amino acid name | 3 letter code | 1 letter code |
|---|---|---|
| alanine | Ala | A |
| arginine | Arg | R |
| asparagine | Asn | N |
| aspartic acid | Asp | D |
| cysteine | Cys | C |
| glutamine | Gln | Q |
| glutamic acid | Glu | E |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |

| amino acid name | 3 letter code | 1 letter code |
| --- | --- | --- |
| tryptophan | Trp | W |
| tyrosine | Tyr | Y |
| valine | Val | V |

D-amino acids include:

| amino acid name | 3 letter code | Alternative abbreviation |
| --- | --- | --- |
| D-alanine | ala | dAla |
| D-arginine | arg | dArg |
| D-asparagine | asn | dAsn |
| D-aspartic acid | asp | dAsp |
| D-cysteine | cys | dCys |
| D-glutamine | gln | dGln |
| D-glutamic acid | glu | dGlu |
| D-glycine | gly | dGly |
| D-histidine | his | dHis |
| D-isoleucine | ile | dIle |
| D-leucine | leu | dLeu |
| D-lysine | lys | dLys |
| D-methionine | met | dMet |
| D-phenylalanine | phe | dPhe |
| D-proline | pro | dPro |
| D-serine | ser | dSer |
| D-threonine | thr | dThr |
| D-tryptophan | trp | dTrp |
| D-tyrosine | tyr | dTyr |
| D-valine | val | dVal |

Non-naturally occurring amino acids include:

| amino acid name | Abbreviation for L form | Abbreviation for D form |
| --- | --- | --- |
| 4-fluorophenylalanine | Fpa | dFpa |
| 2-amino butyric acid | Abu | dAbu |
| ornithine | Orn | dOrn |
| phenylglycine | Phg | dPhg |
| 2-naphthylalanine | Nal | dNal |
| 2,3-diaminopropionic acid | Dap | dDap |
| t-leucine (t-butylglycine) | Tle | dTle |
| Norleucine | Nle | dNle |
| 3-amino-5-phenylpentanoic acid | L-homoPhe (R form) | D-homoPhe (S form) |
| N-methylglycine | Sar | D-Sar |
| N-methylalanine | L-N-MeAla | D-N-MeAla |
| N-methylleucine | L-N-MeLeu | D-N-MeLeu |
| N-methylphenylalanine | L-N-MePhe | D-N-MePhe |

Unless otherwise indicated, an amino acid includes both the L and D forms and mixtures thereof.

An "amino acid side chain" refers to the group attached to a carbon atom of the amino acid backbone. For example, in an -amino acid represented by $NH_2—CH(R^b)—COOH$, $R^b$ is the side chain of this amino acid. Thus, an alanine side chain is a methyl group, and an aspartic acid side chain is a $—CH_2COOH$ group.

An "amide bond" is a covalent chemical bond, $C(O)NR^a$ or $NR^aC(O)$ (wherein $R^a$ is hydrogen, alkyl or substituted alkyl, or $R^a$ may optionally cyclize with the nitrogen atom), formed between two molecules when the carboxyl group of one molecule reacts with the amino group of the other molecule. An amide bond can also be called a peptide bond, amide link, or peptide link, etc. Reactions that lead to the formation of an amide bond are known in the art, such as by using an amide coupling reagent, such as carbodiimides, e.g., dicyclohexylcarbodiimide (DCC), N-(3-dimethylaminopropyl)-N'-ethylcarbodiimide (EDC) and diisopropylcarbodiimide (DIC), triazoles, e.g., 1-hydroxy-benzotriazole (HOBt) and 1-hydroxy-7-aza-benzotriazole (HOAt), triaminophosphonium compounds, benzotriazol-1-yloxy)tris (dimethylamino)phosphonium hexafluorophosphate (BOP) and benzotriazol-1-yloxy)tripyrrolidinophosphonium hexafluorophosphate (PyBOP), tetramethylaminium/Tetramethyluronium compounds, e.g., 2-(1H-7-azabenzotriazol-1-yl)-1,1,3,3-tetramethyl uronium hexafluorophosphate (HATU) and O-benzotriazole-N,N,N',N'-tetramethyluronium-hexafluoro-phosphate (HBTU), etc.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$", etc. are used herein as generic symbols to represent various specific substituents. These symbols can be any substituent, not limited to those disclosed herein, and when they are defined to be certain substituents in one instance, they can, in another instance, be defined as some other substituents.

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

When used in the context of a chemical group, "hydrogen" means —H; "hydroxy" and "hydroxyl" can be used interchangeably and mean —OH; "oxo" means=O; "halo," and "halogen", as used herein can be used interchangeably, mean independently —F, —Cl, —Br or —I; "hydroxyamino" means —NHOH; "nitro" means —$NO_2$; imino means=NH; "cyano" and "nitrile" can be used interchangeably and mean —CN; "isocyanate" means —N═C═O; "azido" means —$N_3$; in a monovalent context "phosphate" means —OP(O)(OH)$_2$ or a deprotonated form thereof; in a divalent context "phosphate" means —OP(O)(OH)O— or a deprotonated form thereof; "mercapto" and "thiol" can be used interchangeably and mean —SH; and "thio" means=S; "sulfonyl" means —S(O)$_2$—; and "sulfinyl" means —S(O)—.

The term "alkyl" a straight or branched chain monovalent hydrocarbyl group. In an embodiment, alkyl has from 1 to 20 carbon atoms (i.e., $C_1$-$C_{20}$ alkyl). In some embodiments, alkyl is a $C_1$-$C_{10}$ alkyl group or a $C_1$-$C_6$ alkyl group. The groups —$CH_3$ (Me), —$CH_2CH_3$ (Et), —$CH_2CH_2CH_3$ (w-Pr), —CH(CH$_3$)$_2$ (iso-Pr), —CH(CH$_3$)$_2$ (cyclopropyl), —$CH_2CH_2CH_2CH_3$ (n-Bu), —CH(CH$_3$)CH$_2$CH$_3$ (sec-butyl), —CH₂CH(CH₃)₂ (iso-butyl), —C(CH₃)₃ (tert-butyl), —CH₂C(CH₃)₃ and (weo-pentyl) are non-limiting examples of alkyl groups.

The term "alkylene" refers to a divalent alkyl group, such as —CH₂—, —CH₂CH₂—, —CH₂CH₂CH₂—, —CH(CH₃)CH₂—, etc.

The term "alkenyl" refers to a monovalent straight or branched hydrocarbyl group with at least one site of unsaturation, i.e., a carbon-carbon, sp² double bond. In some embodiments, alkenyl is a $C_2$-$C_{20}$ alkenyl group, a $C_2$-$C_{10}$ alkenyl group or a $C_2$-$C_6$ alkenyl group. Examples of alkenyl group include, but are not limited to, —CH=CH₂ (vinyl), —CH=CHCH₃, —CH=CHCH₂CH₃, —CH₂CH=CH₂ (allyl), and —CH₂CH=CHCH₃.

The term "alkenylene" refers to a divalent unsaturated alkenyl group. The groups —CH=CH—, —CH=C(CH₃)CH₂—, and —CH=CHCH₂— are non-limiting examples of alkenylene groups.

"Alkynyl" refers to a monovalent hydrocarbon containing normal, secondary or tertiary carbon atoms with at least one site of unsaturation, i.e., a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkynyl) or 2 to 6 carbon atoms (i.e., $C_2$-$C_6$ alkynyl). Examples of alkynyl groups include, but are not limited to, acetylenic (—C≡CH) and propargyl (—CH₂C≡CH).

In some embodiments, the terms "substituted alkyl," "substituted alkylene," "substituted alkenyl," "substituted alkenylene" or "substituted alkynyl" refer to alkyl, alkylene, alkenyl, alkenylene or alkynyl wherein at least one of the hydrogen atoms, for example, one to five, one to three, or one or two hydrogen atoms, are independently replaced by a substituent selected from the group consisting of alkenyl, alkynyl, —O—$R^{100}$, —C(O)—$R^{100}$, —N$R^{100}$C(O)$R^{100}$, —C(O)O—$R^{100}$, —N$R^{100}R^{100}$, —C(O)N$R^{100}R^{100}$, —C(S)N$R^{100}R^{100}$, —N$R^{100}$C(O)N$R^{100}R^{100}$, —N$R^{100}$C(S)N$R^{100}R^{100}$, —O—C(O)N$R^{100}R^{100}$, —S(O)₂N$R^{100}R^{100}$, —O—S(O)₂N$R^{100}R^{100}$, —N$R^{100}$—S(O)₂N$R^{100}R^{100}$, —C(=N$R^{100}$)N$R^{100}R^{100}$, aryl, arylthio, azido, carboxyl, —C(O)O—$R^{101}$, —N$R^{100}$—C(O)O—$R^{101}$, —O—C(O)O—$R^{101}$, cyano, cycloalkyl, —N$R^{100}$C(=N$R^{100}$)N($R^{100}$)₂, halo, hydroxy, hydroxyamino, alkoxyamino, —N$R^{100}$N$R^{100}R^{100}$, heteroaryl, heterocycle, nitro, spirocycloalkyl, —SO₃H, —OS(O)₂—$R^{101}$, —S—$R^{100}$, —S(O)₂—$R^{101}$, —C(S)—$R^{101}$, thiocyanate, thiol, alkylthio, and aryl substituted with halo, CN or OH, wherein each $R^{100}$ is independently selected from the group consisting of hydrogen, alkyl, cycloalkyl, aryl, heteroaryl, and heterocycle, or is a fluorescent label, or two $R^{100}$ groups attached to a common atom are optionally joined together with the atom bound thereto to form a cycloalkyl or heterocycle; and each $R^{101}$ is independently selected from the group consisting of alkyl, cycloalkyl, aryl, heteroaryl, and heterocycle.

The term "halogenated alkyl" or "haloalkyl" is a subset of substituted alkyl, in which one or more hydrogens has been substituted with a halo group (i.e., fluorine, chlorine, bromine, or iodine) and no other atoms aside from carbon, hydrogen and halogen are present. The group —CH₂Cl is a non-limiting example of a haloalkyl. The term "fluoroalkyl" is a subset of substituted alkyl, in which one or more hydrogens has been substituted with a fluoro group and no other atoms aside from carbon, hydrogen and fluorine are present. The groups, —CH₂F, —CF₃, and —CH₂CF₃ are non-limiting examples of fluoroalkyl groups. The term "haloaryl" is a subset of substituted aryl, in which one or more hydrogens has been substituted with a halo group (i.e., fluorine, chlorine, bromine, or iodine) and no other atoms aside from carbon, hydrogen and halogen are present.

The term "alkoxy" refers to the group —O-alkyl, and the term "substituted alkoxy" refers the group —O-(substituted alkyl) wherein alkyl and substituted alkyl are as defined above. Non-limiting examples of alkoxy groups include: —OCH₃, —OCH₂CH₃, —OCH₂CH₂CH₃, —OCH(CH₃)₂, and —OCH(CH₂)₂.

The term "cycloalkyl" as used herein is monovalent a non-aromatic carbon-based ring composed of at least three carbon atoms, for example, 3-14, 3-10 or 3-8 carbons. Cycloalkyl groups include hydrocarbon mono-, bi-, and poly-cyclic rings, whether fused, bridged, or spiro. Examples of cycloalkyl groups include, but are not limited to, cyclopropyl, cyclobutyl, cyclopentyl, cyclohexyl, norbornyl, and the like. The condensed rings may or may not be non-aromatic hydrocarbyl rings provided that the point of attachment is at a cycloalkyl carbon atom. For example, and without limitation, the following is a cycloalkyl group:

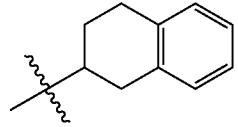

"Cycloalkylene" refers to a cycloalkyl, as defined herein, having two monovalent radical centers derived by the removal of two hydrogen atoms from the same or two different carbon atoms of a parent cycloalkyl. Examples of cycloalkylene include, but are not limited to, cyclopropylene, cyclobutylene, cyclopentylene and cyclohexylene.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" refers to any monocyclic or bicyclic carbon ring of up to 7 atoms in each ring, wherein at least one ring is aromatic, or an aromatic ring system of 5 to 14 carbons atoms which includes a carbocyclic aromatic group fused with a 5-, 6- or 7-membered cycloalkyl group. Examples of aryl groups include, but are not limited to, phenyl, naphthyl, tetrahydronaphthyl and indanyl. Non-limiting examples of aryl groups include phenyl (Ph) or naphthyl, and the monovalent group derived from biphenyl. The condensed ring may or may not be aromatic provided that the point of attachment is at an aromatic carbon atom. For example, and without limitation, the following is an aryl group:

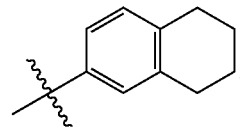

"Arylene" refers to an aryl as defined above having two monovalent radical centers derived by the removal of two hydrogen atoms from two different carbon atoms of a parent aryl. Typical arylene radicals include, but are not limited to, phenylene, e.g.,

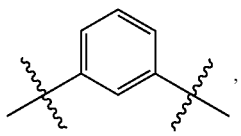 [SMILES: *c1cccc(*)c1]

and naphthylene, e.g.,

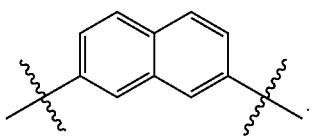 [SMILES: *c1ccc2ccc(*)cc2c1]

"Arylalkylene" refers to an aralkyl as defined above having two monovalent radical centers derived by the removal of one hydrogen atom from the aryl radical and the other hydrogen removed from the alkyl radical of the group.

The term "heteroaryl" refers to a monocyclic, bicyclic or tricyclic ring having from 5 to 7 atoms in each ring, wherein at least one ring is aromatic and contains from 1 to 4 heteroatoms in the ring selected from the group consisting of N, O and S. If more than one ring is present, the rings may be fused or unfused. In some embodiments, the heteroaryl has a total of 5 to 14 ring atoms. In some embodiments, the heteroaryl has a total of 5, 6 or 7 ring atoms. Attachment of heteroaryl can occur via an aromatic ring comprising a heteroatom, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl. The condensed rings may or may not be a heteroatom containing aromatic ring provided that the point of attachment is a heteroaryl atom. For example, and without limitation, the following is a heteroaryl group:

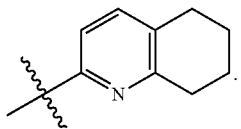 [SMILES: *c1ccc2c(n1)CCCC2]

The term "heterocycloalkyl" or "heterocycle" is a monovalent non-aromatic ring group comprising 3 to 14, 3 to 10, or 3 to 8 ring atoms, where at least one of the ring atoms is carbon atom, and at least one of the ring atoms, for example, 1, 2, 3, or 4 ring atoms, are heteroatoms such as, but not limited to, nitrogen, oxygen, sulfur, or phosphorus. Heterocycloalkyl groups comprise 3 to 14 or 3 to 10 ring atoms may be referred to as 3 to 14 membered or 3 to 10 membered heterocycloalkyl. Heterocycloalkyl groups include, for example, 4-membered, 5-membered, 6-membered, and 7-membered heterocycloalkyl. The condensed rings may or may not be a non-aromatic heteroatom containing ring provided that the point of attachment is a heterocycle group. For example, and without limitation, the following is a heterocycle group:

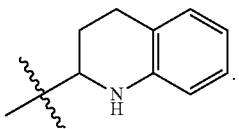 [SMILES: *C1CCc2ccccc2N1]

Examples of heterocycloalkyl and heteroaryl include, but are not limited to, pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1, 2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl, 1H-pyrrolo[3,2-b]pyridin-3-yl, and 1H-pyrazolo [3,2-b] pyridin-3-yl.

"Heteroarylene" refers to a heteroaryl, as defined above, having two monovalent radical centers derived by the removal of two hydrogen atoms from the same or two different carbon atoms of a parent heteraryl group. Non-limiting examples of heteroarylene groups are:

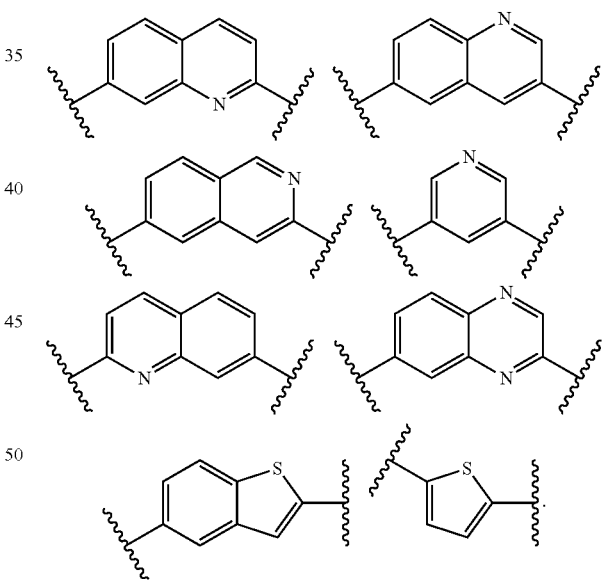

In some embodiments, the terms "substituted cycloalkyl," "substituted cycloalkylene," "substituted aryl," "substituted aryl," "substituted heteroaryl", or "substituted heteroarylene" refer to cycloalkyl, cycloalkylene, cycloalkenyl, aryl, arylene, heteroaryl or heteroarylene wherein at least one of the hydrogen atoms, for example, one to five, one to three, or one or two hydrogen atoms, are independently replaced by a substituent selected from the group consisting of alkyl, alkenyl, alkynyl, —O—$R^{100}$, —C(O)—$R^{100}$, —$NR^{100}$C(O)$R^{100}$, —C(O)O—$R^{100}$, —$NR^{100}R^{100}$, —C(O)$NR^{100}R^{100}$, —C(S)$NR^{100}R^{100}$, —$NR^{100}$C(O)$NR^{100}R^{100}$, —NR$^{100}$C(S)NR$^{100}$R$^{100}$, —O—C(O)NR$^{100}$R$^{100}$, —S(O)$_2$NR$^{100}$R$^{100}$, —O—S(O)$_2$NR$^{100}$R$^{100}$, —NR$^{100}$—S(O)$_2$NR$^{100}$R$^{100}$, —C(=NR$^{100}$)NR$^{100}$R$^{100}$, aryl, arylthio, azido, carboxyl —C(O)O—R$^{101}$, —NR$^{100}$—C(O)O—R$^{101}$, —O—C(O)O—R$^{101}$, cyano, cycloalkyl, —NR$^{100}$C(=NR$^{100}$)N(R$^{100}$)$_2$, halo, hydroxy, hydroxyamino, alkoxyamino, —NR$^{100}$NR$^{100}$R$^{100}$, heteroaryl, heterocycle, nitro, spirocycloalkyl, —SO$_3$H, —OS(O)$_2$—R$^{101}$, —S—R$^{100}$, —S(O)$_2$—R$^{101}$, —C(S)—R$^{101}$, thiocyanate, thiol, and alkylthio, wherein each R$^{100}$ is independently selected from the group consisting of hydrogen, alkyl, cycloalkyl, aryl, heteroaryl, and heterocycle, or is a fluorescent label, or two R$^{100}$ groups attached to a common atom are optionally joined together with the atom bound thereto to form a heterocycle; and each R$^{101}$ is independently selected from the group consisting of alkyl, cycloalkyl, aryl, heteroaryl, and heterocycle.

"Cycloalkylalkyl" refers to an alkyl moiety substituted with a cycloalkyl group. Examples of cycloalkylalkyl groups include cyclopropylmethyl, cyclobutylmethyl, cyclopentylethyl and cyclohexylmethyl. Substituted cycloalkylalkyl refers to a cycloalkylalkyl wherein either or both the alkyl or cycloalkyl portions are substituted as defined herein.

The term "aralkyl" refers to an alkyl group, as defined herein, in which a hydrogen atom has been replaced with an aryl group. Substituted aralkyl refers to an aralkyl wherein either or both the alkyl or aryl portions are substituted as defined herein.

The term "arylalkylene" refers to an aralkyl as defined above having two monovalent radical centers derived by the removal of one hydrogen atom from the aryl radical and the other hydrogen removed from the alkyl radical of the group.

The term "heteroaralkyl," refers to an alkyl group, as defined herein, in which a hydrogen atom has been replaced with a heteroaryl group. Substituted heteroaralkyl refers to a heteroaralkyl wherein either or both the alkyl or heteroaryl portions are substituted as defined herein.

The term "aldehyde" as used herein is represented by the formula —C(O)H. Throughout this specification "CO" or "C(O)" is a short hand notation for a carbonyl group, i.e., C=O.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, heterocycle, alkynyl, cycloalkynyl, aryl, or heteroaryl group as described herein.

The term "ether" as used herein is represented by the formula A$^1$-O-A$^2$, where A$^1$ and A$^2$ can be, independently, optionally substituted alkyl, cycloalkyl, heterocycle, alkenyl, cycloalkenyl, alkynyl, cycloalkynyl, aryl, or heteroaryl group described herein.

The term "stable," as used herein, refers to compounds that are not substantially altered when subjected to conditions to allow for their production, detection, and, in certain aspects, their recovery, purification, and use for one or more of the purposes disclosed herein.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, halo, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "pharmaceutically acceptable salt" refers to a salt of the compound described herein that is, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See Barge, S. M. et al. (1977) J. Pharm. Sci. 66:1, which is incorporated herein by reference in its entirety, at least, for compositions taught therein).

A solvate of a compound is a solid-form of the compound that crystallizes with less than one, one or more than one molecules of a solvent inside in the crystal lattice. A few examples of solvents that can be used to create solvates, such as pharmaceutically acceptable solvates, include, but are not limited to, water, $C_1$-$C_6$ alcohols (such as methanol, ethanol, isopropanol, butanol, and can be optionally substituted) in general, tetrahydrofuran, acetone, ethylene glycol, propylene glycol, acetic acid, formic acid, and solvent mixtures thereof. Other such biocompatible solvents which may aid in making a pharmaceutically acceptable solvate are well known in the art. Additionally, various organic and inorganic acids and bases can be added to create a desired solvate. Such acids and bases are known in the art. When the solvent is water, the solvate can be referred to as a hydrate. In some embodiments, one molecule of a compound can form a solvate with from 0.1 to 5 molecules of a solvent, such as 0.5 molecules of a solvent (hemisolvate, such as hemihydrate), one molecule of a solvent (monosolvate, such as monohydrate) and 2 molecules of a solvent (disolvate, such as dihydrate).

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder, or the relief or elimination of a symptom thereof. Thus, treatment includes:

preventing or protecting against the disease or disorder, that is, causing the clinical symptoms not to develop;

inhibiting the disease or disorder, that is, arresting or suppressing the development of clinical symptoms; and/or relieving the disease or disorder that is, causing the regression of clinical symptoms.

As used herein, the term "a disease mediated at least in part by Ras" and "a disease mediated at least in part by EGFR," etc., intends to refer to a disease, condition, or disorder that is partially or completely caused, sustained or aggravated by the activity (such as abnormal activity) of the gene (including a mutant) or protein of Ras and EGFR, etc. respectively.

As used herein, the expression "a disease resistant to an EGFR inhibitor" includes situations when a disease is non-responsive to an EGFR inhibitor treatment, stops to respond to the EGFR inhibitor treatment after an initial period of responsiveness, or that the patient relapses after completion of the EGFR inhibitor treatment. Non-limiting examples of EGFR inhibitors include for example, commercially available small molecule inhibitors, such as erlotinib, and gefitinib, and anti-EGFR antibodies, such as cetuximab, matuzumab, nimotuzumab, panitumumab, and zalutumumab.

"Administration" can be effected in one dose, continuously or intermittently throughout the course of treatment. Methods of determining the effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, topical application, intrapentoneal, intravenous and by inhalation. An agent of the present invention can be administered for therapy by any suitable route of administration. It will also be appreciated that the preferred route will vary with the condition and age of the recipient, and the disease being treated.

The agents and compositions can be used in the manufacture of medicaments and for the treatment of humans and other animals by administration in accordance with conventional procedures, such as an active ingredient in pharmaceutical compositions.

Compounds

In one aspect, provided herein are compounds of Formula A

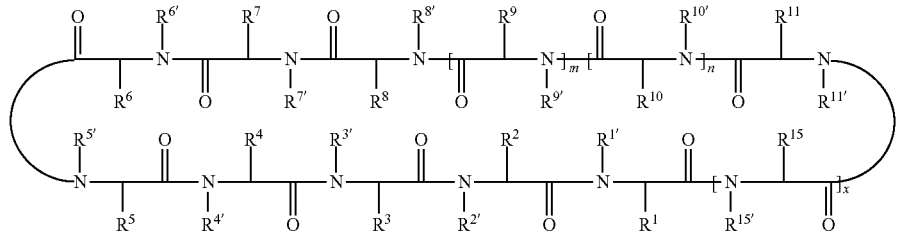

or a tautomer, a pharmaceutically acceptable salt and/or a solvate thereof;

wherein $R^1$, $R^2$, $R^4$, $R^6$, $R^7$, $R^8$, $R^{10}$, $R^{11}$ and each $R^{15}$ are independently H, $C_1$-$C_6$ alkyl, substituted $C_1$-$C_6$ alkyl, phenyl, or substituted phenyl, wherein at least two of $R^1$, $R^2$, $R^4$, $R^6$, $R^7$, $R^8$, $R^{10}$, $R^{11}$ and $R^{15}$ are $C_1$-$C_6$ alkyl substituted with $NHC(=NH)NH_2$ and no four consecutive $R^1$, $R^2$, $R^4$, $R^6$, $R^7$, $R^8$, $R^{10}$, $R^{11}$ and $R^{15}$ are $(CH_2)_3NHC(=NH)NH_2$;

$R^3$ and $R^5$ are independently L-R, wherein L is covalent bond, $C_1$-$C_6$ alkylene, $(CH_2)_sC(O)NH$ or $(CH_2)_sNHC(O)$, and R is aryl, substituted aryl, heteroaryl or substituted heteroaryl;

$R^9$ is $C_1$-$C_6$ alkyl or $C_1$-$C_6$ alkyl substituted with OH;

$R^{1'}$, $R^{2'}$, $R^{3'}$, $R^{4'}$, $R^{5'}$, $R^{6'}$, $R^{7'}$, $R^{8'}$, $R^{9'}$, $R^{10'}$, $R^{11'}$ and each $R^{15'}$ are independently H or methyl;

x is 0, 1, 2, 3 or 4;

s is 0, 1, 2, or 3;

m is 0 or 1; and n is 0 or 1.

In one aspect, provided herein are compounds of Formula B

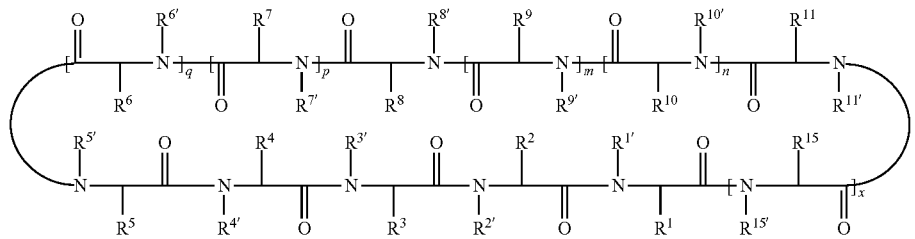

or a tautomer, a pharmaceutically acceptable salt and/or a solvate thereof;

wherein $R^1$, $R^2$, $R^4$, $R^6$, $R^7$, $R^8$, $R^{10}$, $R^{11}$ and each $R^{15}$ are independently H, $C_1$-$C_6$ alkyl, substituted $C_1$-$C_6$ alkyl, phenyl, or substituted phenyl, wherein at least two of $R^1$, $R^2$, $R^4$, $R^6$, $R^7$, $R^8$, $R^{10}$, $R^{11}$ and $R^{15}$ are $C_1$-$C_6$ alkyl substituted with $NHC(=NH)NH_2$ and no four consecutive $R^1$, $R^2$, $R^4$, $R^6$, $R^7$, $R^8$, $R^{10}$, $R^{11}$ and $R^{15}$ are $(CH_2)_3NHC(=NH)NH_2$;

$R^3$ and $R^5$ are independently L-R, wherein L is covalent bond, $C_1$-$C_6$ alkylene, $(CH_2)_sC(O)NH$ or $(CH_2)_sNHC(O)$, and R is aryl, substituted aryl, heteroaryl or substituted heteroaryl;

$R^9$ is $C_1$-$C_6$ alkyl or $C_1$-$C_6$ alkyl substituted with OH;
$R^{1'}$, $R^{2'}$, $R^{3'}$, $R^{4'}$, $R^{5'}$, $R^{6'}$, $R^{7'}$, $R^{8'}$, $R^{9'}$, $R^{10'}$, $R^{11'}$ and each $R^{15'}$ are independently H or methyl;
x is 0, 1, 2, 3 or 4;
s is 0, 1, 2, or 3;
m is 0 or 1;
n is 0 or 1;
p is 0 or 1; and
q is 0 or 1.

In some embodiments, no four consecutive $R^1$, $R^2$, $R^4$, $R^6$, $R^7$, $R^8$, $R^{10}$, $R^{11}$ and $R^{15}$ are $C_1$-$C_6$ alkyl substituted with NHC(=NH)NH$_2$.

In one aspect, provided herein are compounds of Formula I, II or III:

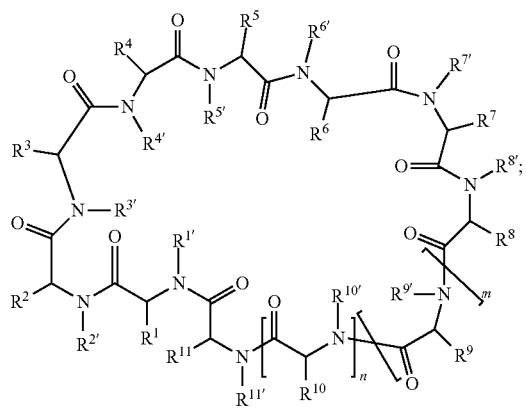

I

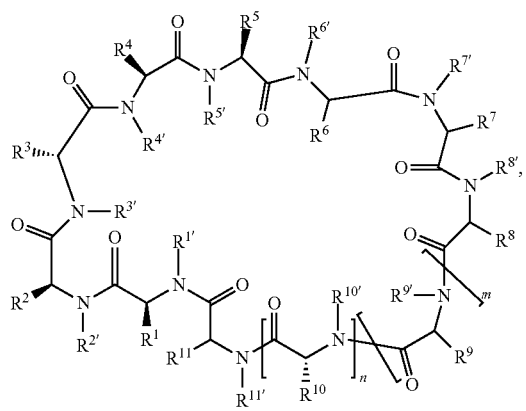

II

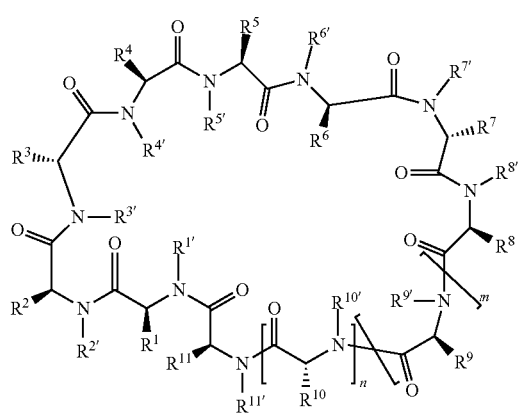

III or a tautomer, a pharmaceutically acceptable salt and/or a solvate thereof;

wherein $R^1$, $R^2$, $R^4$, $R^6$, $R^7$, $R^8$, $R^{10}$ and $R^{11}$ are independently H, $C_1$-$C_6$ alkyl, substituted $C_1$-$C_6$ alkyl, phenyl, or substituted phenyl, wherein at least two of $R^1$, $R^2$, $R^4$, $R^6$, $R^7$, $R^8$, $R^{10}$ and $R^{11}$ are $C_1$-$C_6$ alkyl substituted with NHC(=NH)NH$_2$ and $R^1$, $R^2$, $R^{10}$, and $R^{11}$ cannot be all (CH$_2$)$_3$NHC(=NH)NH$_2$;

$R^3$ and $R^5$ are independently L-R, wherein L is covalent bond, $C_1$-$C_6$ alkylene, (CH$_2$)$_s$C(O)NH or (CH$_2$)$_s$NHC(O), and R is aryl, substituted aryl, heteroaryl or substituted heteroaryl;

$R^9$ is $C_1$-$C_6$ alkyl or $C_1$-$C_6$ alkyl substituted with OH;
$R^{1'}$, $R^{2'}$, $R^{3'}$, $R^{4'}$, $R^{5'}$, $R^{6'}$, $R^{7'}$, $R^{8'}$, $R^{9'}$, $R^{10'}$ and $R^{11'}$ are independently H or methyl;
s is 0, 1, 2, or 3;
m is 0 or 1; and
n is 0 or 1.

In some embodiments, $R^1$, $R^2$, $R^{10}$, and $R^{11}$ are not all $C_1$-$C_6$ alkyl substituted with NHC(=NH)NH$_2$.

In one aspect, provided herein are compounds of any one of Formulas IB-VIB:

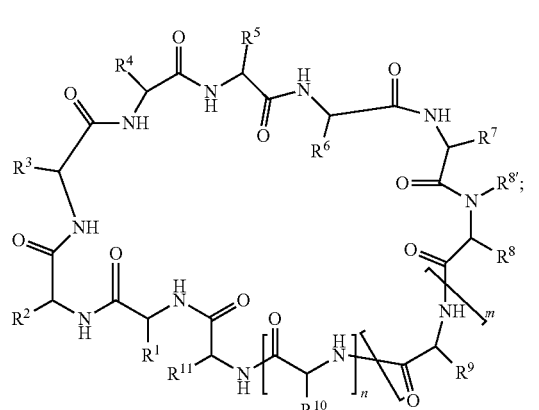

IB

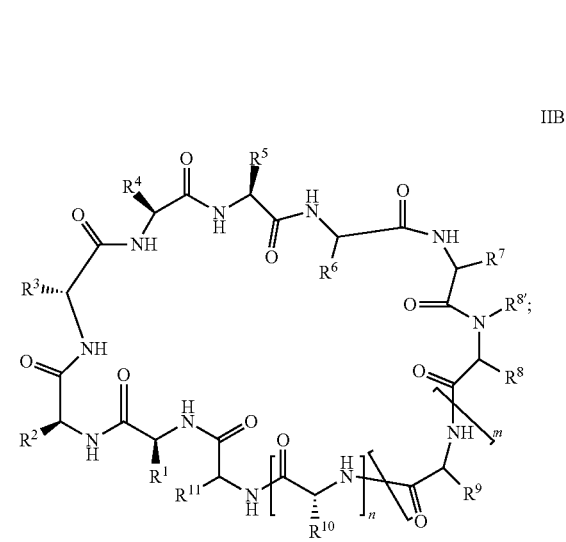

IIB

IIIB

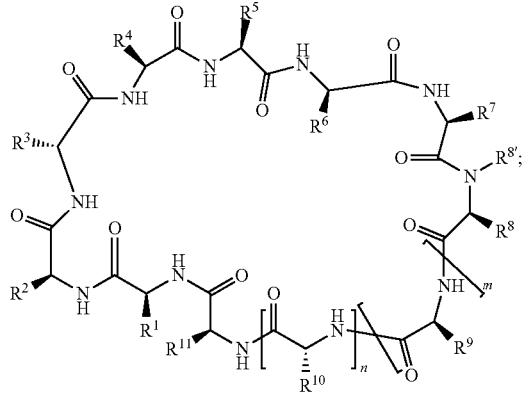

VIB

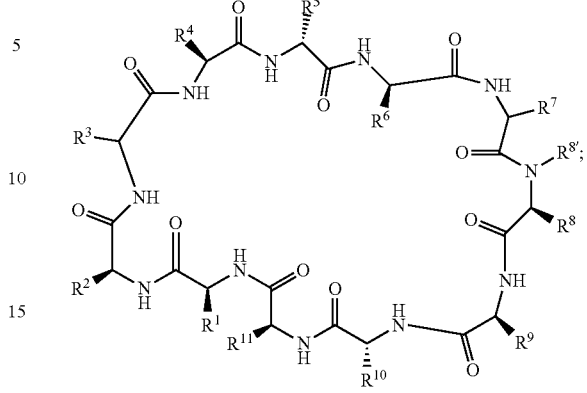

IVB

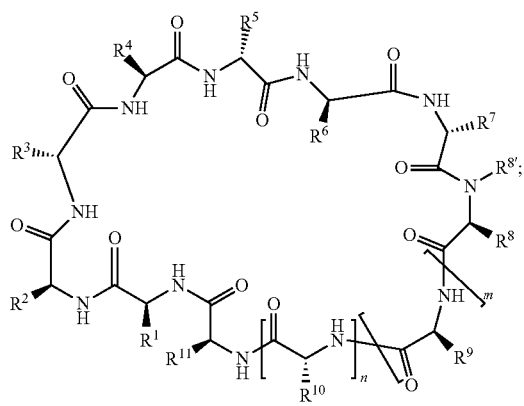

VB

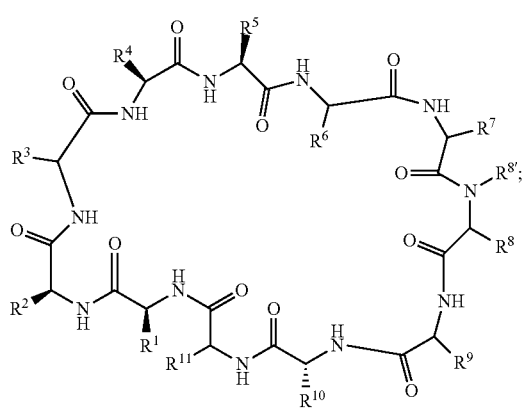

or a tautomer, a pharmaceutically acceptable salt and/or a solvate thereof;
wherein
$R^1$, $R^2$, $R^4$, $R^6$, $R^7$, $R^8$, $R^{10}$ and $R^{11}$ are independently H, $C_1$-$C_6$ alkyl, substituted $C_1$-$C_6$ alkyl, phenyl, or substituted phenyl, wherein at least two of $R^1$, $R^2$, $R^4$, $R^6$, $R^7$, $R^8$, $R^{10}$ and $R^{11}$ are $C_1$-$C_6$ alkyl substituted with NHC(=NH)NH$_2$ and $R^1$, $R^2$, $R^{10}$, and $R^{11}$ cannot be all (CH$_2$)$_3$NHC(=NH)NH$_2$;
$R^3$ and $R^5$ are independently L-R, wherein L is covalent bond, $C_1$-$C_6$ alkylene, (CH$_2$)$_s$C(O)NH or (CH$_2$)$_s$NHC(O), and R is aryl, substituted aryl, heteroaryl or substituted heteroaryl;
$R^9$ is $C_1$-$C_6$ alkyl or $C_1$-$C_6$ alkyl substituted with OH;
$R^{8'}$ is hydrogen or methyl;
s is 0, 1, 2, or 3;
m is 0 or 1; and
n is 0 or 1.

In some embodiments, $R^1$, $R^2$, $R^{10}$, and $R^{11}$ are not all $C_1$-$C_6$ alkyl substituted with NHC(=NH)NH$_2$.

In some embodiments, m is 0 and n is 0. In some embodiments, m is 1 and n is 0. In some embodiments, m is 0 and n is 1. In some embodiments, m is 1 and n is 1.

In some embodiments, $R^1$, $R^2$ and $R^4$ are independently selected from the group consisting of $C_1$-$C_6$ alkyl or $C_1$-$C_6$ alkyl substituted with $R^{20}$, wherein $R^{20}$ is —NH$_2$, —NHC(=NH)NH$_2$, —NHR$^{30}$ or —NHC(=NH)NHR$^{30}$; and wherein $R^{30}$ is a fluorescent label, provided that only one of $R^1$, $R^2$ and $R^4$ is $C_1$-$C_6$ alkyl.

In some embodiments, $R^1$, $R^2$ and $R^4$ are independently selected from —CH$_3$, —(CH$_2$)$_3$NHC(=NH)NH$_2$, —(CH$_2$)$_3$NHC(=NH)NHR$^{30}$, —(CH$_2$)$_4$NH$_2$ and —(CH$_2$)$_4$NHR$^{30}$.

In some embodiments, $R^1$ and $R^4$ are —(CH$_2$)$_3$NHC(=NH)NH$_2$, and $R^2$ is selected from —(CH$_2$)$_3$NHC(=NH)NH$_2$, —(CH$_2$)$_4$NHC(=NH)NHR$^{30}$, —(CH$_2$)$_4$NH$_2$ and —(CH$_2$)$_4$NHR$^{30}$.

In some embodiments, $R^3$ is —(CH$_2$)$_p$-L$^3$-R$^{23}$, wherein p is 0, 1, 2 or 3, L$^3$ is a covalent bond, C(O)NH or NHC(O), and $R^{23}$ is phenyl or naphthyl. In some embodiments, $R^3$ is —(CH$_2$)$_p$—R$^{23}$. In some embodiments, $R^3$ is —CH$_2$naphthyl.

In some embodiments, $R^5$ is —(CH$_2$)$_p$-L$^5$-R$^{25}$, wherein p is 0, 1, 2 or 3, L$^5$ is a covalent bond, C(O)NH or NHC(O), and $R^{25}$ is phenyl or pyridyl, wherein the phenyl and pyridyl are optionally substituted with 1 to 3 substituents independently selected from halo, cyano and OH.

In some embodiments, $R^5$ is selected from the group consisting of —CH$_2$Ph, —CH$_2$Ph(4-fluoro), —CH$_2$Ph(4- chloro), —CH₂Ph(3,4-difluoro), —CH₂Ph(4-OH), —CH₂NHC(O)Ph(3-bromo-5-fluoro), —CH₂NHC(O)Ph(3-chloro), —CH₂NHC(O)Ph(4-cyano), —CH₂NHC(O)Ph(6-chloronicotinoyl) and —CH₂NHC(O)Ph(4-chloro).

In some embodiments, $R^6$ is selected from the group consisting of H, phenyl, $C_1$-$C_6$ alkyl or $C_1$-$C_6$ alkyl substituted with $R^{26}$, wherein $R^{26}$ is selected from the group consisting of $NH_2$, $C(O)NH_2$, $NHC(=NH)NH_2$, and $NH$-$L^6$-$R^{36}$, wherein $L^6$ is a covalent bond, $C(O)$, $C(O)CH=CH$, $C(O)NH$ or $C(S)NH$, and $R^{36}$ is selected from the group consisting of phenyl, pyridyl, or a fluorescent label, wherein the phenyl or pyridyl are optionally substituted with 1 to 3 halo.

In some embodiments, $R^6$ is selected from the group consisting of H, methyl, phenyl, n-butyl, —CH₂CH(CH₃)₃, —CH(CH₃)₃, —(CH₂)₃NHC(=NH)NH₂, —(CH₂)₄NH₂, —CH₂C(O)NH₂, —CH₂Ph, —CH(CH₃)₂, —(CH₂)₄NH(3-bromo-5-fluorobenzoyl), —(CH₂)₄NH(6-chloronicotinoyl), —(CH₂)₄NH(4-chlorocinnamoyl), —(CH₂)₄NH(isonicotinoyl), and —(CH₂)₄NH(3-bromobenzoyl).

In some embodiments, $R^7$ is —(CH₂)$_q$-$L^7$-$R^{27}$, wherein q is 0, 1, 2 or 3, $L^7$ is a covalent bond, $C(O)NH$ or $NHC(O)$, and $R^{27}$ is H, OH, $C(O)NH_2$, heteroaryl, phenyl or naphthyl, wherein the heteroaryl, phenyl or naphthyl is optionally substituted with 1 to 3 substituents independently selected from halo and OH.

In some embodiments, $R^7$ is selected from the group consisting of —CH₂Ph, —CH₂Ph(4-fluoro), —CH₂Ph(4-OH), —CH₂-indolyl, —CH₂OH, —CH₂CH₂C(O)NH₂ and —CH₂C(O)NH₂.

In some embodiments, $R^8$ is selected from the group consisting of H, phenyl, $C_1$-$C_6$ alkyl or $C_1$-$C_6$ alkyl substituted with $R^{28}$, wherein $R^{28}$ is selected from the group consisting of OH, phenyl, naphthyl, heteroaryl, $NH_2$, $NHC(=NH)NH_2$, and $NH$-$L^8$-$R^{38}$, wherein the phenyl, naphthyl, and heteroaryl are optionally substituted with 1 to 3 halo or aralkyl; $L^8$ is a covalent bond, $C(O)$, $C(O)CH=CH$, $C(O)NH$, $NHC(O)CH=CH$, or $C(S)NH$, and $R^{38}$ is selected from the group consisting of H, alkyl, phenyl, pyridyl, or a fluorescent label, wherein the phenyl or pyridyl are optionally substituted with 1 to 3 halo.

In some embodiments, $R^8$ is selected from the group consisting of H, phenyl, n-butyl, isobutyl, —CH₂-indolyl, —(CH₂)₃NHC(=NH)NH₂, —CH₂C(O)NH₂, —(CH₂)₂COOH,

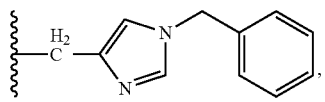 [SMILES: *Cc1cn(Cc2ccccc2)cn1]

—CH₂OH, —CH(CH₃)OH, —(CH₂)₄NH₂, —CH(CH₃)OCH₂Ph, —CH₂Ph, —CH₂— naphthyl, —CH(CH₃)₂, —CH₂NH(3-bromo-5-fluorobenzoyl), —CH₂NH(6-chloronicotinoyl), —CH₂(4-chlorocinnamoyl), —CH₂NH(isonicotinoyl), and —CH₂NH(3-bromobenzoyl). In some embodiments, $R^8$ is selected from —CH₂-indolyl,

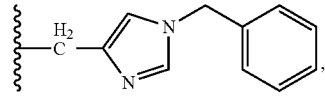 [SMILES: *Cc1cn(Cc2ccccc2)cn1]

—CH(CH₃)OCH₂Ph, —CH₂Ph, —CH₂-naphthyl, —CH(CH₃)₂, —CH₂NH(3-bromo-5-fluorobenzoyl), —CH₂NH(6-chloronicotinoyl), —CH₂(4-chlorocinnamoyl), —CH₂NH(isonicotinoyl), and —CH₂NH(3-bromobenzoyl). In some embodiments, $R^8$ is —CH₂(indol-3-yl).

In some embodiments, $R^9$ is —(CH₂)$_p$-$L^9$-$R^{29}$, wherein p is 0, 1, 2 or 3, $L^9$ is a covalent bond, $C(O)NH$ or $NHC(O)$, and $R^{29}$ is H, OH, aryl or heteroaryl, wherein the aryl or heteroaryl are optionally substituted with 1 to 3 substituents independently selected from halo, cyano and OH.

In some embodiments, $R^{29}$ is selected from the group consisting of OH, phenyl, imidazole and pyridyl, and wherein the phenyl, imidazole and pyridyl are optionally substituted with 1 to 3 substituents independently selected from halo, cyano and OH.

In some embodiments, $R^9$ is selected from the group consisting of $C_1$-$C_3$ alkyl, —C(CH₃)₃, —CH₂OH, and —CH(CH₃)OH.

In some embodiments, $R^{10}$ is H or $C_1$-$C_6$ alkyl.

In some embodiments, $R^{11}$ is —(CH₂)$_p$—$R^{41}$, wherein p is 0, 1, 2 or 3, and $R^{41}$ is $C(O)NH_2$, $NHC(=NH)NH_2$, $C(O)NHR^{42}$, $NHC(=NH)NHR^{42}$, and wherein $R^{42}$ is an amino acid residue.

In some embodiments, $R^{11}$ is —CH₂CH₂C(O)NH₂, —(CH₂)₃—NHC(=NH)NH₂, —CH₂CH₂C(O)NHR⁴², or —(CH₂)₃—NHC(=NH)NH—$R^{42}$, wherein $R^{42}$ is a norleucine residue, a lysine residue or an arginine residue.

In some embodiments, $R^{30}$, $R^{36}$, and $R^{38}$ are independently

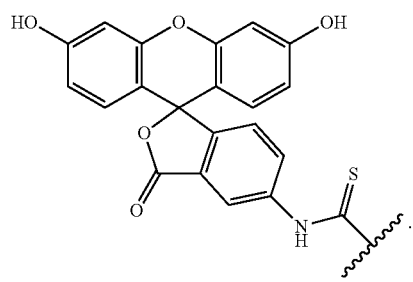 [SMILES: *C(=S)Nc1ccc2c(c1)C(=O)OC21c2ccc(O)cc2Oc2cc(O)ccc21]

In some embodiments, provided herein are compounds selected from:

| Cyclorasin | Sequence |
| --- | --- |
| 1A | (Arg-Arg-nal-Arg-Fpa-Arg-Tyr-Fpa-val-Gln) |
| 2A | (Arg-Arg-nal-Arg-Fpa-asn-Tyr-Thr-asn-Gln) |
| 3A | (Arg-Arg-nal-Arg-Fpa-asn-nal-MeLeu-Gln) |
| 4A | (Arg-Arg-nal-Arg-Fpa-Gly-Fpa-ala-ala-Gln) |
| 5A | (Arg-Arg-nal-Arg-Fpa-nle-val-glu-Ile-val-Gln) |
| 6A | (Arg-Arg-nal-Arg-Fpa-nle-phe-Gly-His-Tyr-Gln) |
| 7A | (Arg-Arg-nal-Arg-Fpa-Arg-Tyr-val-Fpa-Gln) |
| 8A | (Arg-Arg-nal-Arg-Fpa-Phg-Tyr-ser-phe-Gln) |
| 9A | (Arg-Arg-nal-Arg-Fpa-nle-ser-Trp-Thr-ala-Gln) |

-continued

| Cyclorasin | Sequence |
|---|---|
| 10A | (Arg-Arg-nal-Arg-Fpa-nle-Tyr-asn-ala-Ile-Gln) |
| 11A | (Arg-Arg-nal-Arg-Fpa-ala-Fpa-Thr-nal-Gln) |
| 12A | (Arg-Arg-nal-Arg-Fpa-Arg-Trp-Arg-ala-Gln) |
| 13A | (Arg-Arg-nal-Arg-Fpa-asn-Fpa-phe-Abu-Gln) |
| 9A | (Arg-Arg-nal-Arg-Fpa-nle-ser-Trp-Thr-ala-Gln)-Lys |
| 9A(Arg1A) | (Ala-Arg-nal-Arg-Fpa-nle-ser-Trp-Thr-ala-Gln)-Lys |
| 9A(Arg2A) | (Arg-Ala-nal-Arg-Fpa-nle-ser-Trp-Thr-ala-Gln)-Lys |
| 9A(nal3dA) | (Arg-Arg-ala-Arg-Fpa-nle-ser-Trp-Thr-ala-Gln)-Lys |
| 9A(Arg4A) | (Arg-Arg-nal-Ala-Fpa-nle-ser-Trp-Thr-ala-Gln)-Lys |
| 9A(Fpa5A) | (Arg-Arg-nal-Arg-Ala-nle-ser-Trp-Thr-ala-Gln)-Lys |
| 9A(nle6dA) | (Arg-Arg-nal-Arg-Fpa-ala-ser-Trp-Thr-ala-Gln)-Lys |
| 9A(ser7dA) | (Arg-Arg-nal-Arg-Fpa-nle-ala-Trp-Thr-ala-Gln)-Lys |
| 9A(Trp8A) | (Arg-Arg-nal-Arg-Fpa-nle-ser-Ala-Thr-ala-Gln)-Lys |
| 9A(Thr9A) | (Arg-Arg-nal-Arg-Fpa-nle-ser-Trp-Ala-ala-Gln)-Lys |
| 9A1 | (Arg-Arg-nal-Arg-Fpa-dNle-Gln-Trp-Thr-ala-Gln)-Lys |
| 9A2 | (Arg-Arg-nal-Arg-Fpa-dNle-Gln-Trp-Thr-ala-Gln)-lys |
| 9A3 | (Arg-Arg-nal-Arg-Fpa-dNle-Gln-Trp-Thr-ala-Gln)-Arg |
| 9A4 | (Arg-Arg-nal-Arg-Fpa-dNle-Gln-Trp-Thr-ala-Gln)-Nle |
| 9A5 | (Trp-Thr-ala-Arg-Arg-Arg-nal-Arg-Fpa-nle-Gln) |
| 9A6 | (Trp-Thr-ala-arg-Arg-Arg-nal-Arg-Fpa-nle-Gln) |
| 9A7 | (BzlHis-Thr-ala-Arg-Arg-Arg-nal-Arg-Fpa-nle-Gln) |
| 9A8 | (BzlHis-Thr-ala-arg-Arg-Arg-nal-Arg-Fpa-nle-Gln) |
| 9A9 | (Trp-Thr-ala-arg-Arg-Arg-nal-Arg-Fpa-phe-Gln) |
| 9A10 | (Trp-Thr-ala-arg-Arg-Arg-nal-Arg-Fpa-leu-Gln) |
| 9A11 | (Trp-Thr-ala-arg-Arg-Arg-nal-Arg-Fpa-val-Gln) |
| 9A12 | (Trp-Thr-ala-arg-Arg-Arg-nal-Arg-Phe-nle-Gln) |
| 9A13 | (Trp-Thr-ala-arg-Arg-Arg-nal-Arg-Tyr-nle-Gln) |
| 9A14 | (Trp-Thr-val-arg-Arg-Arg-nal-Arg-Fpa-nle-Gln) |
| 9A15 | (Trp-Thr-leu-arg-Arg-Arg-nal-Arg-Fpa-nle-Gln) |
| 9A16 | (Trp-Tle-ala-arg-Arg-Arg-nal-Arg-Fpa-nle-Gln) |
| 9A17 | (Trp-Ser-ala-arg-Arg-Arg-nal-Arg-Fpa-nle-Gln) |
| 9A18 | (Trp-Val-ala-arg-Arg-Arg-nal-Arg-Fpa-nle-Gln) |
| 9A25 | (Dap(3-bromo-5-fluorobenzoyl)-Tle-ala-Arg-Arg-Lys(FITC)-nal-Arg-Fpa-lys-Gln) |
| 9A26 | (Thr(Bzl)-Tle-ala-Arg-Arg-Lys(FITC)-nal-Arg-Fpa-lys-Gln) |
| 9A27 | (Dap(6-chloronicotinoyl)-Tle-ala-Arg-Arg-Lys(FITC)-nal-Arg-Fpa-lys-Gln) |
| 9A28 | (Dap(4-chlorocinnamoyl)-Tle-ala-Arg-Arg-Lys(FITC)-nal-Arg-Fpa-lys-Gln) |
| 9A29 | (Dap(isonicotinoyl)-Tle-ala-Arg-Arg-Lys(FITC)-nal-Arg-Fpa-lys-Gln) |
| 9A30 | (Dap(3-bromobenzoyl)-Tle-ala-Arg-Arg-Lys(FITC)-nal-Arg-Fpa-lys-Gln) |
| 9A31 | (Trp-Tle-ala-Arg-Arg-Lys(FITC)-nal-Arg-Fpa-lys-Gln) |
| 9A32 | (Trp-Tle-ala-Arg-Arg-Lys(FITC)-nal-Arg-Fpa-lys(3-bromo-5-fluorobenzoyl)-Gln) |
| 9A33 | (Trp-Tle-ala-Arg-Arg-Lys(FITC)-nal-Arg-Fpa-lys(6-chloronicotinoyl)-Gln) |
| 9A34 | (Trp-Tle-ala-Arg-Arg-Lys(FITC)-nal-Arg-Fpa-lys(4-chlorocinnamoyl)-Gln) |
| 9A35 | (Trp-Tle-ala-Arg-Arg-Lys(FITC)-nal-Arg-Fpa-lys(isonicotinoyl)-Gln) |
| 9A36 | (Trp-Tle-ala-Arg-Arg-Lys(FITC)-nal-Arg-Fpa-lys(3-bromobenzoyl)-Gln) |
| 9A41 | (Trp-Tle-leu-Arg-Arg-Arg-nal-Arg-Fpa-nle-Gln) |
| 9A42 | (Trp-Thr-ala-Arg-Arg-Arg-nal-Arg-Phe(4-chloro)-nle-Gln) |
| 9A43 | (Trp-Thr-ala-Arg-Arg-Arg-nal-Arg-Phe(3,4-difluoro)-nle-Gln) |
| 9A44a | (Trp-Thr-ala-Arg-Arg-Arg-nal-Arg-Dap(3-bromo-5-fluorobenzoyl)-nle-Gln) |
| 9A44b | (Trp-Tle-ala-Arg-Arg-Arg-nal-Arg-Dap(6-chloronicotinoyl)--nle-Gln) |
| 9A44c | (Trp-Tle-ala-Arg-Arg-Arg-nal-Arg-Dap(4-cyanobenzoyl)-nle-Gln) |
| 9A44d | (Trp-Tle-ala-Arg-Arg-Arg-nal-Arg-Dap(3-chlorobenzoyl)-nle-Gln) |
| 9A45 | (Trp-Thr-ala-Arg-Arg-Arg-nal-Arg-Fpa-arg-Gln) |
| 9A46 | (Trp-Tle-ala-Arg-Arg-Arg-nal-Arg-Fpa-nle-Gln) |
| 9A47 | (Trp-Thr-val-Arg-Arg-Arg-nal-Arg-Fpa-nle-Gln) |
| 9A48 | (Trp-Tle-val-Arg-Arg-Arg-nal-Arg-Fpa-nle-Gln) |
| 9A49 | (Nal-Thr-ala-Arg-Arg-Arg-nal-Arg-Fpa-nle-Gln) |
| 9A50 | (Trp-Tle-val-Arg-Arg-Arg-nal-Arg-Phe(3,4-difluoro)-arg-Gln) |
| 9A51 | (Trp-Tle-val-arg-Arg-Arg-nal-Arg-Phe(3,4-difluoro)-nle-Gln) |
| 9A52 | (Trp-Thr-ala-Arg-Arg-Arg-nal-Arg-Phe(3,4-difluoro)-arg-Gln) |
| 9A53 | (Trp-Tle-val-arg-Arg-Arg-nal-Arg-Fpa-nle-Gln) |
| 9A54 | (Trp-Tle-val-Arg-Arg-Arg-nal-Arg-Phe(3,4-difluoro)-nle-Gln) |
| 9A55 | (Trp-Thr-ala-Arg-Arg-Arg-Nal-Arg-Fpa-nle-Gln) | or a tautomer, a pharmaceutically acceptable salt and/or a solvate thereof;

wherein "(" and ")" represent the point of cyclization through an amide bond between the two amino acids to which "(" and ")" are connected.

In some embodiments, the compounds are not (Arg-Arg-nal-Arg-Fpa-Arg-Tyr-Fpa-val-Gln); (Arg-Arg-nal-Arg-Fpa-asn-Tyr-Thr-asn-Gln); (Arg-Arg-nal-Arg-Fpa-nle-val-glu-Ile-val-Gln); (Arg-Arg-nal-Arg-Fpa-Phg-Tyr-ser-phe-Gln); (Arg-Arg-nal-Arg-Fpa-nle-Tyr-asn-ala-Ile-Gln); or (Arg-Arg-nal-Arg-Fpa-ala-Fpa-Thr-nal-Gln);

or a tautomer, a pharmaceutically acceptable salt and/or a solvate thereof;

wherein "(" and ")" represent the point of cyclization through an amide bond between the two amino acids to which "(" and ")" are connected.

As used herein the symbols represent the structures:

| Symbol | Structure |
|---|---|
| Ph(4-fluoro) | [structure] |
| Ph(4-chloro) | [structure] |
| Ph(3,4-difluoro) | [structure] |
| Ph(4-OH) | [structure] |
| Ph(3-bromo-5-fluoro) | [structure] |
| Ph(4-cyano) | [structure] |
| Ph(6-chloronicotinoyl) | [structure] |
| 3-bromo-5-fluorobenzoyl | [structure] |
| 6-chloronicotinoyl | [structure] |
| 4-chlorocinnamoyl | [structure] |
| isonicotinoyl | [structure] |
| 3-bromobenzoyl | [structure] |

As used herein, the term "detectable label" intends a directly or indirectly detectable compound or composition that is conjugated directly or indirectly to the composition to be detected. Detectable labels include radioisotope labels, e.g., N-terminal histadine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. Detectable labels also include fluorescent labels which are fluorescence compounds, such as fluorescein isothiocyanate (FITC), NHS-fluorescein, fluorescein, green fluorescent protein (GFP) and the like, that can be attached or conjugated to the compounds described herein. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, luminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6$^{th}$ ed.).

In another aspect, the fluorescent label is functionalized to facilitate covalent attachment to a compound. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Antibody-Drug-Conjugates

In another aspect, provided is an antibody-drug-conjugate comprising an antibody conjugated with a compound of Formula A, B, I, II, III, IB, IIB, IIIB, IVB, VB or VIB.

The formation of an antibody drug conjugates (ADC) can combine the properties of both antibodies and cytotoxic drugs by targeting potent cytotoxic drugs to the antigen-expressing target cell, such as tumor cells, internalization, and release of the drug, thereby enhancing their anti-tumor activity. Antibodies that can be conjugated to the compounds described herein can be a whole mAb or an antibody fragment such as a single-chain variable fragment [scFv]. In some embodiments, the antibody is an antibody that targets EGFR.

Antibodies that can be conjugated to the compounds described herein can be monoclonal antibodies, polyclonal antibodies, dimers, multimers, multispecific antibodies (e.g., bispecific antibodies), and antibody fragments that exhibit the desired biological activity. The antibodies may be murine, human, humanized, chimeric, or derived from other species.

An antibody is a protein generated by the immune system that is capable of recognizing and binding to a specific antigen. (Janeway, C., et al., Immuno Biology, 5th Ed., Garland Publishing, New York (2001)). A target antigen generally has numerous binding sites, also called epitopes, recognized by complementary determining regions (CDRs) on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In some embodiment, the immunoglobulin is of human, murine, or rabbit origin, or a combination thereof.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; minibodies (Olafsen et al., Characterization of engineered anti-p185HER-2 (scFv-CH3)2 antibody fragments (minibodies) for tumor targeting, Protein Eng. Design & Sel. 17(4):315-323(2004)), fragments produced by a Fab expression library, anti-idiotypic (anti-Id) antibodies, CDR, and epitope-binding fragments of any of the above which immunospecifically bind to target cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibody is directed against a single determinant on the antigen, whereas polyclonal antibody preparations include different antibodies directed against different determinants (epitopes). Monoclonal antibodies may be made by the methods known in the art such as the hybridoma method described in Kohler et al., Continuous cultures of fused cells secreting antibody of predefined specificity, Nature, 256:495 (1975), or the recombinant DNA methods described in, for example, U.S. Pat. Nos. 4,816,567; 5,807,715. The monoclonal antibodies may also be isolated from phage antibody libraries using the techniques described in for example Clackson et al., Making antibody fragments using phage display libraries, Nature, 352:624-628 (1991); Marks et al., By-passing immunization: human antibodies from V gene libraries displayed on phage, J. Mol. Biol., 222:581-597 (1991).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. Examples of chimeric antibodies are described in, e.g., U.S. Pat. No. 4,816,567; and Morrison et al., Chimeric antibody with specificity to human B cell surface antigen, Proc. Natl. Acad. Sci. USA, 81:6851-6855 (1984)). Chimeric antibodies of interest herein include "primatized" antibodies comprising variable domain antigen-binding sequences derived from a non-human primate (e.g., Old World Monkey, Ape etc) and human constant region sequences.

Examples of antibodies that can be conjugated to the compounds described herein include huMAb4D5-1, huMAb4D5-2, huMAb4D5-3, huMAb4D5-4, huMAb4D5-5, huMAb4D5-6, huMAb4D5-7 and huMAb4D5-8 (trastuzumab), described in Table 3 of U.S. Pat. No. 5,821,337. In some embodiments, the antibody is a monoclonal antibody directed against the EGFR, such as cetuximab, panitumumab, zalutumumab, nimotuzumab, and matuzumab.

The antibody and compounds described herein can be conjugated directly, i.e., through a covalent bond, or through linker. The linker can be a stable, chemical linker with a labile bond which can be cleaved under certain conditions, such as presence of an enzyme or change in pH in vivo, to release the compound from the antibody. Examples of linkers that can be used and methods of preparing antibody-drug-conjugates include those described in, e.g., Nolting B., Linker technologies for antibody-drug conjugates, Methods Mol. Biol.; 1045:71-100 (2013), Flygare J. A., et al., Antibody-drug conjugates for the treatment of cancer, Chem Biol Drug Des., 81(1):113-21 (2013), Alley S. C., et al., Antibody-drug conjugates: targeted drug delivery for cancer, Current Opinion in Chemical Biology, 14(4): 529-537 (2010), Carter, P. J., et al., Antibody-Drug Conjugates for Cancer Therapy, Cancer Journal, 14(3): 154-169 (2008), and US2012/0121615, which are incorporated by reference in their entirety.

Pharmaceutical Compositions

In another aspect, provided are compositions comprising a compound described herein, such as a compound of Formula A, B, I, II, III, IB, IIB, or IIIB. In general, the compound is mixed with a suitable carrier or excipient in a therapeutically effective amount. By a "therapeutically effective dose", "therapeutically effective amount", or, interchangeably, "pharmacologically acceptable dose" or "pharmacologically acceptable amount", it is meant that a sufficient amount of the compound and a pharmaceutically acceptable carrier, will be present in order to achieve a desired result, e.g., treating a disease mediated at least in part by Ras.

In general, the compounds described herein will be administered in a therapeutically effective amount by any of the accepted modes of administration. The actual amount of the compound, i.e., the active ingredient, will depend upon numerous factors such as the severity of the disease to be treated, the age and relative health of the subject, the potency of the compound used, the route and form of administration, and other factors. The compound can be administered any suitable dosage regimes, such as once, twice, three times, or four times, etc. a day, or as needed. All of these factors are within the skill of the attending clinician.

Therapeutically effective amounts of the compounds may range from approximately 0.05 to 50 mg per kilogram body weight of the recipient per day; for example, about 0.1-25 mg/kg/day, or from about 0.5 to 10 mg/kg/day. Thus, for administration to a 70 kg person, the dosage range can be about 1-3500 mg per day.

In general, compounds of this invention will be administered as pharmaceutical compositions by any one of the following routes: oral, transdermal, intranasal, by suppository, parenteral (e.g., intramuscular, intravenous or subcutaneous), or intrathecal administration. Compositions can take the form of tablets, pills, capsules, semisolids, powders, sustained release formulations, solutions, suspensions, elixirs, aerosols, or any other appropriate compositions. The choice of formulation depends on various factors such as the mode of drug administration and bioavailability of the drug substance.

Another manner for administering compounds is inhalation. This is an effective method for delivering a therapeutic agent directly to the respiratory tract (see U.S. Pat. No. 5,607,915). For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

The compositions are comprised of in general, a compound described herein in combination with at least one pharmaceutically acceptable excipient. Acceptable excipients are non-toxic, aid administration, and do not adversely affect the therapeutic benefit of the compound. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, phosphate buffered saline, aqueous dextrose, and glycols.

Compressed gases may be used to disperse a compound in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of the compound of based on the total formulation, with the balance being one or more suitable pharmaceutical excipients. Preferably, the compound is present at a level of about 1-80 wt %.

Treatment of Diseases

In one aspect, provided are methods of inhibiting Ras comprising contacting Ras with a compound described herein, such as a compound of Formula A, B, I, II, III, IB, IIB, IIIB, IVB, VB or VIB, or an antibody-drug conjugate thereof. The contacting can be in vitro or in vivo. In one aspect, provided are methods of treating a disease mediated at least in part by Ras comprising administering a therapeutically effective amount of a compound described herein, such as a compound of Formula A, B, I, II, III, IB, IIB, IIIB, IVB, VB or VIB, or an antibody-drug conjugate thereof, to a patient in need thereof. In some embodiments, the Ras is K-Ras. In some embodiments, the Ras is H-Ras. In some embodiments, the Ras is N-Ras. In some embodiments, the Ras is wild-type Ras, such as wild-type K-Ras, H-Ras, or N-Ras. In some embodiments, the Ras is a Ras mutant, such as mutant K-Ras, H-Ras, or N-Ras. In some embodiments, the disease is a cancer, such as lung cancer, pancreatic cancer, colon cancer, or melanoma. In a further aspect, the cancer is resistant to an EGFR inhibitor can be a second line, third line, or fourth line treatment in addition to a first line treatment.

In one aspect, provided are methods of treating a cancer comprising administering a therapeutically effective amount of a compound described herein, such as a compound of Formula A, B, I, II, III, IB, IIB, IIIB, IVB, VB or VIB, or an antibody-drug conjugate thereof, to a patient in need thereof. In some embodiments, the cancer is lung cancer, pancreatic cancer, colon cancer, or melanoma. In a further aspect, the cancer is resistant to an EGFR inhibitor and the treatment can be a second line, third line, or fourth line treatment in addition to a first line treatment.

In one aspect, provided are methods of treating a disease mediated at least in part by EGFR comprising administering a therapeutically effective amount of a compound described herein, such as a compound of Formula A, B, I, II, III, IB, IIB, IIIB, IVB, VB or VIB, or an antibody-drug conjugate thereof, to a patient in need thereof.

In some embodiments, the disease mediated at least in part by EGFR is a cancer, such as colon cancer, lung cancer, anal cancer and glioblastoma multiforme. Treatment of disease includes sub-clinical as well as clinical suppression of the disease, e.g., slowing, reduction or inhibition of tumor growth, longer time to tumor progression after surgical resection, longer overall survival.

In connection with the therapies described above and disclosed herein, the therapies can be combined with other known therapies, e.g., surgical resection of a tumor mass or the administration of other anticancer agents such as tyrosine kinase inhibitor or antibodies that bind EGFR. In some embodiments, the patient's tumor expresses a mutant EGFR, such as a L858R or T790M mutant. The L858 mutation is sensitive to erlotinib and gefitinib. The T790 mutation confers resistance. Accordingly, the appropriate combination therapy is selected based on the patient's appropriate tumor genotype, which can be determined using methods. Methods to identify such tumors are known in the art. Accordingly, in one aspect, a patient's tumor is biopsied to determine EGFR status and the therapies as described herein are administered to patients identified as expressing mutant EGFR. The compounds of this invention have the benefit of being therapeutic in patients that have failed on EGFR inhibitors. They may also be selected as first line therapies in patients with mutant EGFR.

In a still further aspect, provided is a method of treating a disease resistant to, or likely resistant to, an EGFR inhibitor, such as erlotinib, cetuximab, gefitinib, lapatinib, or panitumumab, which method comprises administering an effective amount of a compound of Formula A, B, I, II, III, IB, IIB, IIIB, IVB, VB or VIB, or an antibody-drug conjugate thereof to a patient in need of the treatment. In some embodiments, the disease resistant to an EGFR inhibitor is a disease mediated at least in part by mutant EGFR, such as a T790M mutant. In some embodiments, the EGFR inhibitor is erlotinib. In a further aspect, the cancer is resistant to an EGFR inhibitor and the treatment can be a second line, third line, or fourth line treatment in addition to a first line treatment.

In some embodiments, the method further comprises determining whether a disease is resistant or likely resistant to an EGFR inhibitor without administering an EGFR inhibitor by determining the presence and types of EGFR mutants. EGFR inhibitor resistant EGFR mutants and methods of determining the presence of the EGFR mutants are generally known in the art, such as described in, e.g., William Pao and Juliann Chmielecki, Rational, biologically based treatment of EGFR-mutant non-small-cell lung cancer, Nat Rev Cancer, 2010; 10(11):760-774.

In one aspect, provided are methods of treating a patient in need of a Ras inhibitor, which method comprises
determining the amount of phospho-Mek and/or phospho-Erk in a cell of the patient;
administering a therapeutically effective amount of a compound described herein, such as a compound of Formula A, B, I, II, III, IB, IIB, IIIB, IVB, VB or VIB, or an antibody-drug conjugate thereof, to a patient;
determining the amount of phospho-Mek and/or phospho-Erk in a cell of the patient after the administration;
continuing to administer a therapeutically effective amount of the compound to the patient if a decrease in phospho-Mek and/or phospho-Erk is detected.

In a still further aspect, provided is a method of inhibiting phosphorylation of Mek and/or Erk, which method comprises contacting a cell in need of inhibition of phosphorylation of Mek and/or Erk with an effective amount of a compound of Formula A, B, I, II, III, IB, IIB, IIIB, IVB, VB or VIB, or an antibody-drug conjugate thereof.

In some embodiments, a decrease in the amount of phospho-Mek and/or phospho-Erk in a cell of the patient after the administration is detected if the amount of phospho-Mek and/or phospho-Erk after the administration is no more than 90%, no more than 80%, no more than 70%, no more than 60%, no more than 50%, no more than 40%, no more than 30%, no more than 20%, or no more than 10% of the amount of phospho-Mek and/or phospho-Erk before the administration.

In a still further aspect, provided is a method of inhibiting phosphorylation of Akt, which method comprises contacting a cell in need of inhibition of phosphorylation of Akt with an effective amount of a compound of Formula A, B, I, II, III, IB, IIB, IIIB, IVB, VB or VIB, or an antibody-drug conjugate thereof. The contacting can be in vitro or in vivo.

In one aspect, provided are methods of treating a patient in need of a Ras inhibitor, which method comprises
determining the amount of phospho-Akt in a cell or tissue sample isolated from the patient;
administering a therapeutically effective amount of a compound described herein, such as a compound of Formula A, B, I, II, III, IB, IIB, IIIB, IVB, VB or VIB, or an antibody-drug conjugate thereof, to a patient;
determining the amount of phospho-Akt in a cell of the patient after the administration;
continuing to administer a therapeutically effective amount of the compound to the patient if a decrease in phospho-Akt is detected and do not administer another dose if no decrease is detected and/or continuing to monitor the level of phospho-Akt in a sample isolated from the patient.

In some embodiments, a decrease in the amount of phospho-Akt in a sample isolated from the patient after the administration is detected if the amount of phospho-Akt after the administration is no more than 90%, no more than 80%, no more than 70%, no more than 60%, no more than 50%, no more than 40%, no more than 30%, no more than 20%, or no more than 10% of the amount of phospho-Akt before the administration.

The determination of the amount of phospho-Akt, phospho-Mek and/or phospho-Erk can be achieved by methods described herein or known in the art, such as by the use of an antibody that recognizes and binds phospho-Akt, e.g., with the use of a Western blots.

General Synthetic Methods

In one aspect, the invention relates to methods of preparing the compounds or antibody-drug-conjugates described herein.

The compounds or antibody-drug-conjugates can be prepared from readily available starting materials using methods described herein and known in the art, such as solution phase or solid phase peptide synthesis methods. For example, the cyclic peptides described herein can be prepared by coupling suitable protected amino acids using common coupling reagents, such as those described herein. It will be appreciated that where typical or preferred process conditions (i.e., reaction temperatures, times, mole ratios of reactants, solvents, pressures, etc) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. For example, when coupling the amino group of amino acid AA1 with the acid group of amino acid AA2, the acid group of AA1 can be protected by an acid protecting group such as a methy, ethyl, t-butyl, or benzyl ester, and the amino group of AA2 can be protected with an amino protecting group such as Fmoc, Boc or Cbz. After coupling of AA1 and AA2, the amino protecting group of AA2 can be removed by methods known in the art to give the free amino group, which can then be use to couple with a third amino acid AA3 having a free acid group and a protected amino group. Further, certain amino acids comprise one or more functional groups in the side chain, for example, lysine has a side-chain amino group. To avoid complication in the coupling reaction, the side-chain functional group can be protected, such as by a different protecting group. Such side-chain protecting groups can be removed after completion of the coupling of all amino acids in the sequence. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds or antibody-drug-conjugates may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials are generally known compounds or can be prepared by known procedures or obvious modifications thereof. For example, many of the starting materials, such as amino acids, are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4$^{th}$ Edition), and Larock's *Comprehensive Organic Transformations* (VCH Publishers Inc., 1989).

The various starting materials, intermediates, and compounds of the invention may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Examples

Ras genes are frequently activated in human cancers, but the Ras proteins remain "undruggable" by the conventional small-molecule approach due to absence of any obvious binding pockets on their surfaces. By using a combination of combinatorial library screening and medicinal chemistry approaches, a family of cyclic peptides were discovered with unique properties. These cell permeable cyclic peptides bound selectively to Ras-GTP with nanomolar affinities and inhibited Ras signaling and cancer cell proliferation by directly blocking the Ras-effector protein interactions. The results demonstrate the feasibility of developing bifunctional cyclic peptides for inhibition of intracellular protein-protein interactions and direct Ras inhibitors as a novel class of anticancer agents.

The Ras family GTPases (K-Ras, H-Ras, and N-Ras) play critical roles in many signaling pathways and regulate cell proliferation, differentiation, and survival (Karnoub, A. E. et al. (2008) Nat Rev. Mol. Cell Biol. 9:517). Wild-type Ras oscillates between inactive GDP-bound (Ras-GDP) and active GTP-bound forms (Ras-GTP), with the latter interacting with and activating multiple effector proteins including Raf, PI3K, and Ral-GDS. Somatic mutations that cause constitutive activation of Ras are the most common activating lesions found in human cancers. Genetic studies suggest that blocking the Ras-effector protein interaction should have therapeutic benefits in cancer patients (White, M. A. et al. (1995) Cell 80:533; Castellano, E. et al. (2013) Cancer Cell 24:617); however, doing so pharmacologically has been challenging, because the Ras protein surface has no obvious pockets for small-molecule drugs to bind (Wang, W. et al. (2012) Bioorg. Med. Chem. Lett. 22:5766). Consequently, most of the drug discovery efforts have so far been focused on inhibiting signaling molecules downstream of Ras (Gysin, S. et al. (2011) Genes Cancer 2:359), the posttranslational processing/membrane anchoring of Ras (Gysin, S. et al. (2011) Genes Cancer 2:359; Zimmermann, G. et al. (2013) Nature 497:638), or the nucleotide exchange activity of Ras (Taveras, A. G. et al. (1997) Bioorg. Med. Chem. 5:125; Maurer, T. et al. (2012) Proc. Natl. Acad. Sci. U.S.A. 109:5299; Sun, Q. et al. (2012) Angew. Chem. Int. Ed. 51:6140; Patgiri, A. et al. (2011) Nat. Chem. Biol. 7:585; Ostrem, J. M. et al. (2013) Nature 503:548).

A cyclic peptide inhibitor against K-Ras was discovered by screening a combinatorial library (compound 12) (Wu, X. et al. (2013) Med. Chem. Commun. 4:378).

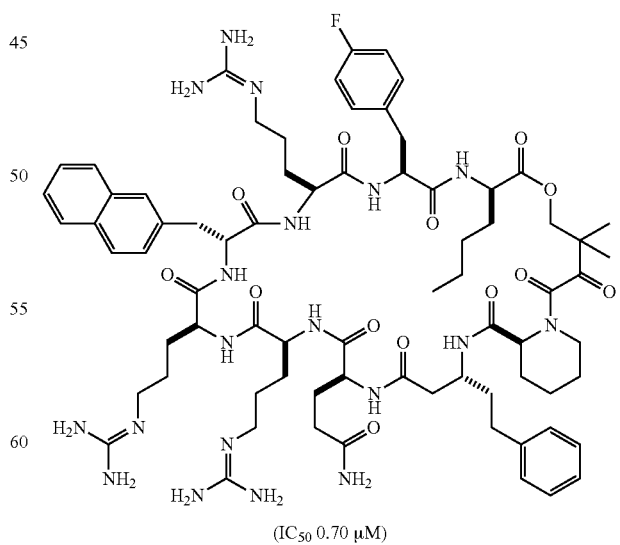

Compound 12

(IC$_{50}$ 0.70 µM)

Figure 1:
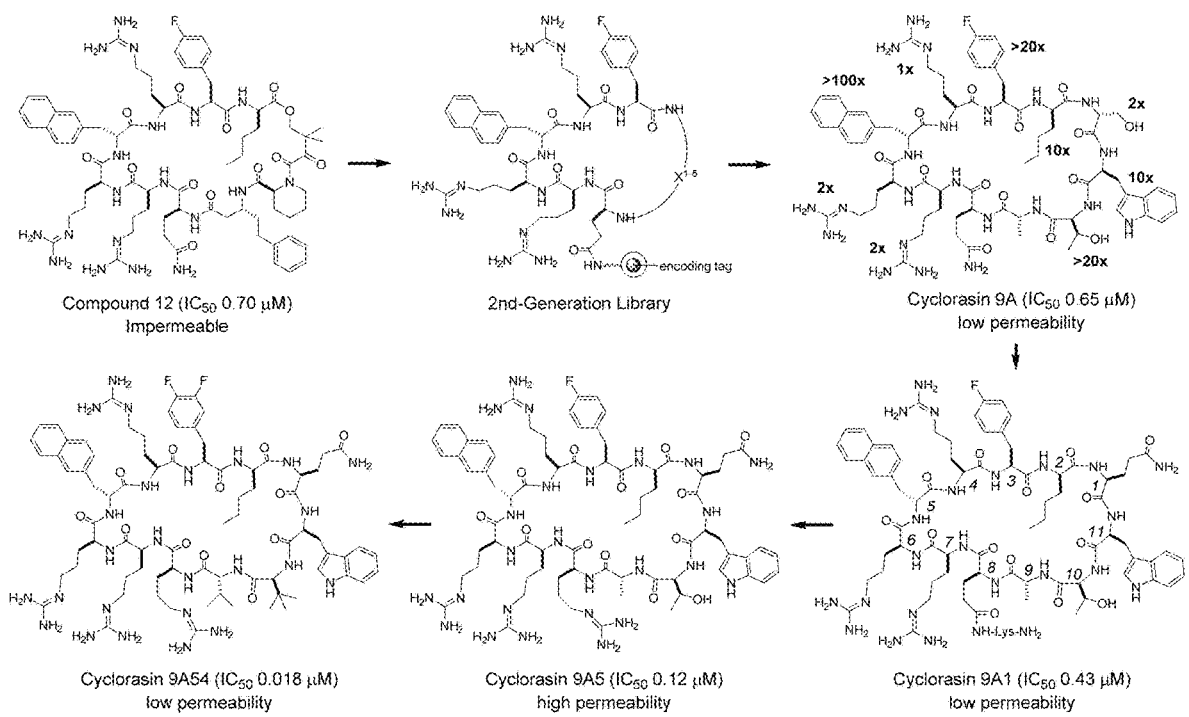
FIG. 1 is a flowchart showing the evolution of compound 12 into potent Ras inhibitors through combinatorial library synthesis/screening and individual synthesis of analogues.

Compound 12 bound directly to K-Ras (K$_D$ 0.83 µM), blocking the interaction of K-Ras with Raf, PI3K, and Ral-GDS in vitro, but lacked cellular activity due to inability to cross the cell membrane. To improve the potency, metabolic stability, and membrane permeability of compound 12, Applicants designed a second-generation library by replacing the nle-Dkb-Pip-D-homoPhe motif [where nle=D-norleucine; Dkb=3,3-dimethyl-2-ketobutyryl; Pip=L-pipecolinate; D-homoPhe=(R)-3-amino-5-phenylpentanoic acid], which is synthetically cumbersome and susceptible to hydrolysis at the lactone moiety, with a random peptide sequence of 0-5 amino acids (X1-5). The X1 position featured an nle or null residue whereas the X2-X5 positions were constructed with 28 proteinogenic and unnatural amino acids (The 28-amino acid set included 11 proteinogenic amino acids [Arg, Asp, Gln, Gly, His, Ile, Leu, Pro, Thr, Trp, and Tyr], 4 nonproteinogenic α-L-amino acids [L-4-fluorophenylalanine (Fpa), L-2-amino butyric acid (Abu), L-ornithine (Orn), and L-phenylglycine (Phg)], 9 α-D-amino acids [D-2-naphthylalanine (dNal), dAla, dAsn, dGlu, dLys, dNle, dPhe, dSer, and dVal] and 4 N-methylated amino acids [L-Sar, L-N-MeAla, L-N-MeLeu and L-N-MePhe]). The Arg-Arg-nal-Arg-Fpa motif was retained for binding to Ras. Interestingly, the Arg-Arg-nal-Arg-Fpa motif is rich in arginine residues, the residue that was reported to promote cell permeability of cyclic peptides (ACS Chem Biol. 2013 Feb. 15; 8(2):423-31). The invariant glutamine residue was also retained to serve as the point of cyclization and attachment to the solid support. The library (theoretical diversity 1.27× $10^6$) was synthesized on spatially segregated TentaGel microbeads in the one bead-two compound format (Joo, S. H. et al. (2006) J. Am. Chem. Soc. 128:13000), with each bead displaying a unique cyclic peptide on its surface and a linear peptide of the same sequence in its interior as an encoding tag (FIG. 1).

Screening of the cyclic peptide library against a constitutively active K-Ras mutant (G12V) identified 13 hits (Table 1). The 13 hits were resynthesized, labeled with fluorescein isothiocyanate (FITC), purified by HPLC, and tested for binding to K-Ras by fluorescence anisotropy (FA). Peptides 4A, 5A, 7A, 9A (FIG. 1), 12A, and 13A showed strong binding ($K_D$≤1 μM), with peptides 9A and 12A having the highest affinities ($K_D$=0.24 and 0.44 μM, respectively) (FIGS. 5A-5B). In a homogeneous time-resolved fluorescence (HTRF) assay, peptides 9A and 12A inhibited the Ras-Raf interaction with $IC_{50}$ values of 0.65 and 1.0 μM, respectively, whereas the other four peptides showed no significant inhibition (FIG. 2A and FIGS. 5A-5B). To Applicants' satisfaction, peptides 9A and 12A contained additional Trp and/or Arg residues and were cell permeable (FIGS. 6A-6B). Peptides 9A and 12A exhibited weak antiproliferative activity against lung cancer cells (FIG. 2B) and were named as Cyclorasin (for cyclic Ras inhibitor) 9A and 12A, respectively.

Next, Cyclorasin 9A was subjected to an alanine scan analysis (replacement of each residue with an L- or D-alanine) to identify the residues involved in K-Ras binding. Removal of the side chain of D-naphthylalanine (nal), L-4-fluorophenylalanine (Fpa), L-threonine (Thr), nle, or L-tryptophan (Trp) resulted in ≥10-fold reduction in K-Ras binding affinity, whereas replacement of the remaining residues had only minor effects (≤2-fold) (FIG. 1). Since the D-serine was not critical for Ras binding, Applicants replaced it with an L-Gln to provide an alternative site for peptide cyclization and attachment to solid support. The resulting peptides (Cyclorasin 9A1-4), which contained the newly installed Gln (designated as position 1) but differently substituted Gln side chain at position 8 (the original site of cyclization), all had similar potency for inhibition of the Ras-Raf interaction (Table 2), suggesting that the side chain of Gln8 was not critical for binding to Ras. Applicants therefore replaced Gln8 with an L- or D-arginine, anticipating that the increased arginine content would further improve the cell permeability of the peptide (Qian, Z. et al. (2013) ACS Chem. Biol. 8:423). To Applicants' delight, the resulting peptides (Cyclorasin 9A5 and 9A6) had both improved cell permeability (vide infra) and ~3-fold higher potency than 9A1 against K-Ras ($IC_{50}$=0.12 and 0.17 μM, respectively). Further modification of 9A5 and 9A6 produced mixed results; most of the substitutions either had no significant effect or decreased the binding affinity for Ras, however, a few resulted in significant improvements (Table 2). For example, replacement of D-Ala9 with a D-valine (val9) increased the affinity by ~2-fold, as was substitution of L-tert-leucine (Tle) for Thr10 (Cyclorasin 9A14 and 9A16). Introduction of a second fluorine to the Fpa3 side chain increased the Ras binding affinity by 2-fold ($IC_{50}$=0.064 μM for Cyclorasin 9A43). Replacement of nle2 with D-arginine (Cyclorasin 9A45) also increased the Ras binding affinity by 4-fold (Table 2). Finally, a combination of val9, Tle10, and 3,4-difluorophenylalanine (F2pa) at position 3 produced Cyclorasin 9A51 and 9A54 as highly potent Ras inhibitors ($IC_{50}$=0.015 and 0.018 μM, respectively) (FIG. 2A).

The ability of the cyclic peptides to inhibit the Ras-Raf interaction suggests that they are able to bind to Ras-GTP. To determine whether they are specific for Ras-GTP, pure Ras-GTP, Ras-GDP, and Ras bound with a nonhydrolyzable GTP analogue (Ras-GPPNP) (Maurer, T. et al. (2012) Proc. Natl. Acad. Sci. U.S.A. 109:5299) were prepared and tested for binding to FITC-labeled Cyclorasin 9A5 (FIGS. 7A-7B). FITC-9A5 bound to Ras-GTP, Ras-GPPNP, and Ras-GDP with $K_D$ values of 0.44, 0.64, and 2.5 μM, respectively (FIG. 2C) (Maurer, T. et al. (2012) Proc. Natl. Acad. Sci. U.S.A. 109:5299), which reduced its affinity for Ras by ~3-4 fold. FITC-9A5 was also tested for binding to H-Ras and five arbitrarily selected control proteins (bovine serum albumin, protein-tyrosine phosphatase 1B, glutathione-S-transferase-SHD SH2 domain fusion protein, maltose-binding protein-XIAP BIR3 domain fusion, and glutathione-S-transferase-FKBP fusion protein). As expected from the high sequence identity between K- and H-Ras, FITC-9A5 bound to H-Ras with an affinity ($K_D$=0.50 μM) similar to that of K-Ras. However, it showed only weak binding to bovine serum albumin and maltose-binding protein-XIAP BIR3 domain fusion ($K_D$~30 μM for both) but no significant binding to the other three control proteins (FIGS. 7A-7B). Thus, Cyclorasin 9A5 (and likely the other analogues) is a selective ligand for Ras-GTP.

Cyclorasin peptides that had good Ras binding affinities ($IC_{50}$<0.2 μM in the HTRF assay) were tested for antiproliferative activity against lung cancer cells using the MTT assay (Mosmann, T. (1983) J. Immunol. Methods 65:55). Cyclorasin 9A5 was most potent, having an $IC_{50}$ value of ~3 μM against H1299 cells (FIG. 2B); other peptides including those that had higher affinity for Ras than 9A5 (e.g., 9A51 and 9A54) were less effective for inhibition of cancer cell growth (Table 2). This indicates that factors other than the Ras-binding affinity (e.g., cellular uptake efficiency) also affect the cellular activity of the cyclic peptide inhibitors. Indeed, treatment of lung cancer A549 cells with FITC-labeled Cyclorasin 9A5 resulted in intense, defuse fluorescence throughout the cytoplasm, whereas cells treated with FITC-labeled 9A54 had weaker and predominantly punctate fluorescence (FIG. 2D). Fluorescence-activated cell sorting showed that A549 cells treated with FITC-9A5 had ~5-fold higher mean fluorescence intensity than those treated with FITC-9A54 (FIG. 2E). These data suggest that the lung cancer cells treated with Cyclorasin 9A5 accumulated a substantially higher cytoplasmic concentration of the Ras inhibitor as compared to those treated with 9A54, likely due to more efficient cellular uptake and/or endosomal escape of the former (Qian, Z. et al. (2013) ACS Chem. Biol. 8:423).

Two well characterized Ras effector pathways are the Raf-Mek-Erk and PI3K-Akt signaling pathways (Karnoub, A. E. et al. (2008) Nat Rev. Mol. Cell Biol. 9:517). To determine whether the cyclic peptides inhibited the intracellular Ras activity, Applicants monitored the phosphorylation levels of Mek, Erk, and Akt in cells before and after treatment with the Ras inhibitors. Treatment of H1299 cells with 13 µM Cyclorasin 9A5 for 5 min resulted in significant reduction in EGF-induced phosphorylation of Akt and Mek (FIG. 3A). Longer exposure to the inhibitor (≥10 min) completely abolished the phosphorylation of the proteins, while the total Akt and Mek protein levels remained constant. The phosphorylation level of Erk also decreased, but to a lesser extent and at a later time point, which is consistent with Erk functioning downstream of Mek on the Ras signaling pathway. In order to rule out that the observed downregulation of P-Mek, P-Erk and P-Akt is caused by inhibition of EGFR signaling, the effect of Cyclosrasin 9A5 on the phosphorylation of the EGFR was tested by performing an IP/Western Blot experiment (FIG. 3E). Active, signaling EGFR is highly autohophosphorylated. Applicants determined that Cyclorasin 9A5 does no affect the EGFR phosphorylation level. Hence, the downregulation of P-Mek, P-Erk and P-Aid is not a result of EGFR inhibition, but instead, likely due to the inhibition of Ras.

Inhibition of Mek and Akt phosphorylation was dose-dependent, with $IC_{50}$ values of ~5 µM when H1299 cells were treated with 9A5 for 10 min (FIG. 3B). Different cell lines showed varying sensitivity to Ras inhibition (FIG. 3C). While a 10-min treatment with 10 µM Cyclorasin 9A5 almost completely abolished Mek, Erk and Akt phosphorylation in H1299, H1975, and H1650 cells, significant Mek and Erk phosphorylation remained in A549 cells, which were previously shown to be less sensitive to K-Ras knockdown by siRNA (Singh, A. (2009) Cancer Cell 15:489). FIG. 4 demonstrates that some cancer cells like A549 are resistant to Ras inhibitors because the MAPK pathway is not downregulated after exposure to the drug. In the MTT assay, A549 cells were also found to be more resistant to the Ras inhibitors than other cell lines.

H1975 and H1650 lung cancer cells are driven by mutated EGFR. These cell lines express wildtype K-Ras in contrast to H1299 and A549 cells which are driven by mutated K-Ras. The Western Blot experiment in FIG. 3C shows that Cyclorasin 9A5 can inhibit both wildtype and mutant K-Ras. Mutated EGFR is an important drug target in lung cancer. The inhibition of mutated EGFR leads to the downregulation of the MAPK and PI3K pathways since the EGFR signals through Ras. The data disclosed herein demonstrates that lung cancer cells driven by mutated EGFR can be inhibited by targeting Ras with compounds like Cyclorasin 9A5 since the inhibition of the EGFR and the inhibition of Ras have the same effect on MAPK/PI3K.

Compound 9A5 inhibited the basal phosphorylation of Mek and Akt in cells unstimulated with EGF (FIG. 8).

The inhibition of Ras affects proliferation and survival of cells. However, cells exposed to Cyclorasin 9A5 also demonstrate rapid morphological changes as reflected in the contraction of plasma membrane extensions and a general rounding up of the cells. These morphological changes are consistent with a collapse of the actin cytoskeleton. The dephosphorylation of cofilin activates the actin filament severing activity of this protein. The severing of actin filaments results in the collapse of the actin cytoskeleton. Using immunofluorescence to visualize actin filaments, Applicants demonstrated that actin filaments are absent from cells treated with Cyclorasin 9A-5 (FIG. 3D). Without actin filaments, cells tend to round up and lose attachment to the substrate.

TABLE 1

Cyclic Peptides and Their Affinities for K-Ras

| Cyclorasin | Sequence | $K_D$ (µM) |
|---|---|---|
| 1A | (Arg-Arg-nal-Arg-Fpa-Arg-Tyr-Fpa-val-Gln) | >10 |
| 2A | (Arg-Arg-nal-Arg-Fpa-asn-Tyr-Thr-asn-Gln) | >10 |
| 3A | (Arg-Arg-nal-Arg-Fpa-asn-nal-MeLeu-Gln) | 0.91 ± 0.23 |
| 4A | (Arg-Arg-nal-Arg-Fpa-Gly-Fpa-ala-ala-Gln) | 0.77 ± 0.24 |
| 5A | (Arg-Arg-nal-Arg-Fpa-nle-val-glu-Ile-val-Gln) | >10 |
| 6A | (Arg-Arg-nal-Arg-Fpa-nle-phe-Gly-His-Tyr-Gln) | Resynthesis failed |
| 7A | (Arg-Arg-nal-Arg-Fpa-Arg-Tyr-val-Fpa-Gln) | 0.88 ± 0.27 |
| 8A | (Arg-Arg-nal-Arg-Fpa-Phg-Tyr-ser-phe-Gln) | >10 |
| 9A | (Arg-Arg-nal-Arg-Fpa-nle-ser-Trp-Thr-ala-Gln) | 0.24 ± 0.06 |
| 10A | (Arg-Arg-nal-Arg-Fpa-nle-Tyr-asn-ala-Ile-Gln) | >10 |
| 11A | (Arg-Arg-nal-Arg-Fpa-ala-Fpa-Thr-nal-Gln) | >10 |
| 12A | (Arg-Arg-nal-Arg-Fpa-Arg-Trp-Arg-ala-Gln) | 0.44 ± 0.13 |
| 13A | (Arg-Arg-nal-Arg-Fpa-asn-Fpa-phe-Abu-Gln) | 1.0 ± 0.2 |

TABLE 2

Cyclorasin 9A Analogs and their Biological Activities

| Cyclorasin | Structure | HTRF $IC_{50}$ (µM) | Anti-proliferative Activity $IC_{50}$ (µM) | Binding affinity $K_D$ (µM) |
|---|---|---|---|---|
| 9A | (Arg-Arg-nal-Arg-Fpa-nle-ser-Trp-Thr-ala-Gln)-Lys | 0.65 ± 0.11 | 18 ± 4 | 0.24 ± 0.06 |
| 9A(Arg1A) | (Ala-Arg-nal-Arg-Fpa-nle-ser-Trp-Thr-ala-Gln)-Lys | 1.3 ± 0.2 | | |
| 9A(Arg2A) | (Arg-Ala-nal-Arg-Fpa-nle-ser-Trp-Thr-ala-Gln)-Lys | 0.94 ± 0.29 | | |
| 9A(nal3dA) | (Arg-Arg-ala-Arg-Fpa-nle-ser-Trp-Thr-ala-Gln)-Lys | NA | | |
| 9A(Arg4A) | (Arg-Arg-nal-Ala-Fpa-nle-ser-Trp-Thr-ala-Gln)-Lys | 0.39 ± 0.28 | | |
| 9A(Fpa5A) | (Arg-Arg-nal-Arg-Ala-nle-ser-Trp-Thr-ala-Gln)-Lys | >10 | | |

TABLE 2-continued

Cyclorasin 9A Analogs and their Biological Activities

| Cyclorasin | Structure | HTRF IC$_{50}$ (µM) | Anti-proliferative Activity IC$_{50}$ (µM) | Binding affinity K$_D$ (µM) |
|---|---|---|---|---|
| 9A(nle6dA) | (Arg-Arg-nal-Arg-Fpa-ala-ser-Trp-Thr-ala-Gln)-Lys | 7.7 ± 5.6 | | |
| 9A(ser7dA) | (Arg-Arg-nal-Arg-Fpa-nle-ala-Trp-Thr-ala-Gln)-Lys | 0.77 ± 0.49 | | |
| 9A(Trp8A) | (Arg-Arg-nal-Arg-Fpa-nle-ser-Ala-Thr-ala-Gln)-Lys | 7.2 ± 1.0 | | |
| 9A(Thr9A) | (Arg-Arg-nal-Arg-Fpa-nle-ser-Trp-Ala-ala-Gln)-Lys | >10 | | |
| 9A1 | (Arg-Arg-nal-Arg-Fpa-dNle-Gln-Trp-Thr-ala-Gln)-Lys | 0.43 ± 0.38 | 13 ± 2 | |
| 9A2 | (Arg-Arg-nal-Arg-Fpa-dNle-Gln-Trp-Thr-ala-Gln)-lys | 0.58 ± 0.41 | | |
| 9A3 | (Arg-Arg-nal-Arg-Fpa-dNle-Gln-Trp-Thr-ala-Gln)-Arg | 0.58 ± 0.61 | | |
| 9A4 | (Arg-Arg-nal-Arg-Fpa-dNle-Gln-Trp-Thr-ala-Gln)-Nle | 0.50 ± 0.10 | | |
| 9A5 | (Trp-Thr-ala-Arg-Arg-Arg-nal-Arg-Fpa-nle-Gln) | 0.12 ± 0.01 | 3.1 ± 0.3 | |
| 9A6 | (Trp-Thr-ala-arg-Arg-Arg-nal-Arg-Fpa-nle-Gln) | 0.17 ± 0.10 | | |
| 9A7 | (BzlHis-Thr-ala-Arg-Arg-Arg-nal-Arg-Fpa-nle-Gln) | 0.44 ± 0.16 | 10 ± 1 | |
| 9A8 | (BzlHis-Thr-ala-arg-Arg-Arg-nal-Arg-Fpa-nle-Gln) | 0.59 ± 0.12 | | |
| 9A9 | (Trp-Thr-ala-arg-Arg-Arg-nal-Arg-Fpa-phe-Gln) | NP | | |
| 9A10 | (Trp-Thr-ala-arg-Arg-Arg-nal-Arg-Fpa-leu-Gln) | 0.24 ± 0.13 | 10 ± 3 | |
| 9A11 | (Trp-Thr-ala-arg-Arg-Arg-nal-Arg-Fpa-val-Gln) | 0.31 ± 0.08 | | |
| 9A12 | (Trp-Thr-ala-arg-Arg-Arg-nal-Arg-Phe-nle-Gln) | 0.43 ± 0.68 | 9.6 ± 1.3 | |
| 9A13 | (Trp-Thr-ala-arg-Arg-Arg-nal-Arg-Tyr-nle-Gln) | NI | | |
| 9A14 | (Trp-Thr-val-arg-Arg-Arg-nal-Arg-Fpa-nle-Gln) | 0.13 ± 0.07 | 5.4 ± 2.4 | |
| 9A15 | (Trp-Thr-leu-arg-Arg-Arg-nal-Arg-Fpa-nle-Gln) | 0.11 ± 0.04 | 12 ± 1 | |
| 9A16 | (Trp-Tle-ala-arg-Arg-Arg-nal-Arg-Fpa-nle-Gln) | 0.11 ± 0.01 | 3.5 ± 0.6 | |
| 9A17 | (Trp-Ser-ala-arg-Arg-Arg-nal-Arg-Fpa-nle-Gln) | 0.72 ± 0.31 | | |
| 9A18 | (Trp-Val-ala-arg-Arg-Arg-nal-Arg-Fpa-nle-Gln) | 0.23 ± 0.11 | | |
| 9A25 | (Dap(3-bromo-5-fluorobenzoyl)-Tle-ala-Arg-Arg-Lys(FITC)-nal-Arg-Fpa-lys-Gln) | | | 0.47 ± 0.10 |
| 9A26 | (Thr(Bzl)-Tle-ala-Arg-Arg-Lys(FITC)-nal-Arg-Fpa-lys-Gln) | | | 0.71 ± 0.07 |
| 9A27 | (Dap(6-chloronicotinoyl)-Tle-ala-Arg-Arg-Lys(FITC)-nal-Arg-Fpa-lys-Gln) | | | 1.0 ± 0.1 |
| 9A28 | (Dap(4-chlorocinnamoyl)-Tle-ala-Arg-Arg-Lys(FITC)-nal-Arg-Fpa-lys-Gln) | | | 0.16 ± 0.02 |
| 9A29 | (Dap(isonicotinoyl)-Tle-ala-Arg-Arg-Lys(FITC)-nal-Arg-Fpa-lys-Gln) | | | 1.2 ± 0.1 |
| 9A30 | (Dap(3-bromobenzoyl)-Tle-ala-Arg-Arg-Lys(FITC)-nal-Arg-Fpa-lys-Gln) | | | 0.64 ± 0.07 |
| 9A31 | (Trp-Tle-ala-Arg-Arg-Lys(FITC)-nal-Arg-Fpa-lys-Gln) | | | 0.11 ± 0.01 |
| 9A32 | (Trp-Tle-ala-Arg-Arg-Lys(FITC)-nal-Arg-Fpa-lys(3-bromo-5-fluorobenzoyl)-Gln) | | | NB |
| 9A33 | (Trp-Tle-ala-Arg-Arg-Lys(FITC)-nal-Arg-Fpa-lys(6-chloronicotinoyl)-Gln) | | | NB |
| 9A34 | (Trp-Tle-ala-Arg-Arg-Lys(FITC)-nal-Arg-Fpa-lys(4-chlorocinnamoyl)-Gln) | | | NB |

TABLE 2-continued

Cyclorasin 9A Analogs and their Biological Activities

| Cyclorasin | Structure | HTRF IC$_{50}$ (µM) | Anti-proliferative Activity IC$_{50}$ (µM) | Binding affinity K$_D$ (µM) |
|---|---|---|---|---|
| 9A35 | (Trp-Tle-ala-Arg-Arg-Lys(FITC)-nal-Arg-Fpa-lys(isonicotinoyl)-Gln) | | | NB |
| 9A36 | (Trp-Tle-ala-Arg-Arg-Lys(FITC)-nal-Arg-Fpa-lys(3-bromobenzoyl)-Gln) | | | NB |
| 9A41 | (Trp-Tle-leu-Arg-Arg-Arg-nal-Arg-Fpa-nle-Gln) | 2.0 ± 0.9 | | |
| 9A42 | (Trp-Thr-ala-Arg-Arg-Arg-nal-Arg-Phe(4-chloro)-nle-Gln) | 0.13 ± 0.02 | | |
| 9A43 | (Trp-Thr-ala-Arg-Arg-Arg-nal-Arg-Phe(3,4-difluoro)-nle-Gln) | 0.064 ± 0.007 | 6.9 ± 0.8 | |
| 9A44a | (Trp-Thr-ala-Arg-Arg-Arg-nal-Arg-Dap(3-bromo-5-fluorobenzoyl)-nle-Gln) | 0.083 ± 0.008 | | |
| 9A44b | (Trp-Tle-ala-Arg-Arg-Arg-nal-Arg-Dap(6-chloronicotinoyl)--nle-Gln) | 0.52 ± 0.16 | | |
| 9A44c | (Trp-Tle-ala-Arg-Arg-Arg-nal-Arg-Dap(4-cyanobenzoyl)-nle-Gln) | 0.15 ± 0.05 | | |
| 9A44d | (Trp-Tle-ala-Arg-Arg-Arg-nal-Arg-Dap(3-chlorobenzoyl)-nle-Gln) | 0.049 ± 0.007 | 14 ± 2 | |
| 9A45 | (Trp-Thr-ala-Arg-Arg-Arg-nal-Arg-Fpa-arg-Gln) | 0.036 ± 0.004 | 8.9 ± 2.1 | |
| 9A46 | (Trp-Tle-ala-Arg-Arg-Arg-nal-Arg-Fpa-nle-Gln) | 0.13 ± 0.02 | | |
| 9A47 | (Trp-Thr-val-Arg-Arg-Arg-nal-Arg-Fpa-nle-Gln) | 0.086 ± 0.011 | | |
| 9A48 | (Trp-Tle-val-Arg-Arg-Arg-nal-Arg-Fpa-nle-Gln) | 0.048 ± 0.003 | 11 ± 3 | |
| 9A49 | (Nal-Thr-ala-Arg-Arg-Arg-nal-Arg-Fpa-nle-Gln) | 0.10 ± 0.01 | 6.3 ± 0.4 | |
| 9A50 | (Trp-Tle-val-Arg-Arg-Arg-nal-Arg-Phe(3,4-difluoro)-arg-Gln) | >1 | | |
| 9A51 | (Trp-Tle-val-arg-Arg-Arg-nal-Arg-Phe(3,4-difluoro)-nle-Gln) | 0.015 ± 0.009 | 6.7 ± 0.8 | |
| 9A52 | (Trp-Thr-ala-Arg-Arg-Arg-nal-Arg-Phe(3,4-difluoro)-arg-Gln) | >1 | | |
| 9A53 | (Trp-Tle-val-arg-Arg-Arg-nal-Arg-Fpa-nle-Gln) | 0.027 ± 0.011 | 13 ± 1 | |
| 9A54 | (Trp-Tle-val-Arg-Arg-Arg-nal-Arg-Phe(3,4-difluoro)-nle-Gln) | 0.018 ± 0.003 | 7.2 ± 0.4 | |
| 9A55 | (Trp-Thr-ala-Arg-Arg-Arg-Nal-Arg-Fpa-nle-Gln) | 0.94 ± 0.28 | 12 ± 1 | |

In Tables 1 and 2, a three-letter code starting with a capital letter indicates an "L" amino acid, unless preceded with "d", which then denotes a "D" amino acid. Further, a three-letter code starting with a lowercase letter indicates an "D" amino acid. For example, "Nle" denotes L-norleucine, "dNle" and "nle" both denote D-norleucine.

Experimental Details

Materials.

Reagents for peptide synthesis were purchased from Peptides International (Louisville, Ky.), NovaBiochem (La Jolla, Calif.), Anaspec (San Jose, Calif.), Chem-Impex International Inc. (Wood Dale, Ill.), or Aapptec (Lousiville, Ky.). N-Hydroxysuccinimidyl biotin was purchased from Chem-Impex International (Wood Dale, Ill.) and N-(9-fluorenyl-methoxycarbonyloxy)succinimide (Fmoc-OSu) from Advanced ChemTech. Phenyl isothiocyanate (PITC), isopropyl β-D-1-thiogalactopyranoside (IPTG), protease inhibitor cocktail tablets, ampicillin and kanamycin were purchased from Sigma-Aldrich. Cell proliferation kit (MTT) was purchased from Roche (Indianapolis, Ind.). Cell culture media, fetal bovine serum, penicillin-streptomycin, 0.25% trypsin-EDTA, DPBS (2.67 mM potassium chloride, 1.47 mM potassium phosphate monobasic, 137 mM sodium chloride, 8.06 mM sodium phosphate dibasic), streptavidin-coated Dynabeads M-280, Texas red N-hydroxysuccinimide ester, and tetramethylrhodamine (TMR) azide were purchased from Invitrogen (Carlsbad, Calif.). Anti-GST-Tb and Anti-HA d2 antibodies were purchased from Cisbio (Bedford, Mass.). Recombinant K-Ras WT, H-Ras WT, Rac1, RhoA and CDC42 were purchased from Origene (Rockville, Md.). Solvents and other chemical reagents were purchased from Sigma-Aldrich or VWR (West Chester, Pa.).

Expression and Purification of K-Ras and GST-Raf RBD.

The G12V mutant K-Ras (amino acids 1-185) was recombinantly fused to glutathione S-transferase (GST) at its N-terminus and a hemagglutinin (HA) tag (YPYDVPDYA) at its C-terminus and expressed in Escherichia coli BL21 cells. The cells were grown at 37° C. in Luria broth supplemented with 0.05 mg/mL kanamycin to an OD600 of 0.6 when protein expression was induced by addition of IPTG for a final concentration of 1 mM. After 5 h of incubation at 30° C., the cells were harvested by centrifugation. The cell pellets were lysed by sonication in a lysis buffer (40 mM Tris-HCl, 150 mM NaCl, 0.5% Triton X-100, 5 mM β-mercaptoethanol, pH 8.0) containing a protease inhibitor cocktail tablets (Sigma). The crude cell lysate was loaded onto a glutathione-Sepharose 4B column (GE Healthcare) and the bound GST-K-Ras was eluted with an elution buffer (50 mM Tris, pH 8.0, 10 mM glutathione). After buffer exchange into PBS, the protein was quickly frozen and stored at −80° C. To generate K-Ras without the GST tag, the GST-K-Ras protein (2 mg in PBS) was treated with 20 units of thrombin (GE Healthcare) for 16 h at 4° C. The reaction mixture was passed through a glutathione-Sepharose 4B column to remove the released GST and the resulting K-Ras protein was stored at −80° C. GST-Ras RBD was expressed in *Escherichia coli* BL21 cells. The cells were grown at 37° C. in Luria broth supplemented with 0.05 mg/mL ampicillin to an OD600 of 0.6 when protein expression was induced by addition of IPTG for a final concentration of 1 mM. GST-Raf RBD was purified as described above for GST-K-Ras.

Preparation of Ras-GDP, Ras-GTP, and Ras-GPPNP.

K-Ras bound with guanosine diphosphate (GDP) or guanosine 5'-[β,γ-imido] triphosphate (GPPNP) was prepared as previously described (Maurer, T. et al. (2012) Proc. Natl. Acad. Sci. U.S.A. 109:5299). To prepare Ras-GTP, purified K-Ras was incubated with 20 mM EDTA plus 2 mM GTP in PBS overnight at 4° C. After addition of 40 mM of $MgCl_2$, the protein was dialyzed against PBS. The nucleotide loading was monitored by reversed-phase HPLC under ion pairing conditions as previously described (John, J. et al. (1990) Biochemistry 29:6058).

Protein Labeling.

To label GST-K-Ras with biotin, a freshly thawed Ras protein solution (50 μM, 1 mL) was adjusted to pH 8.0 by the addition of 1 M $NaHCO_3$ and treated with 2 equivalents of N-hydroxysuccinimidyl biotin dissolved in DMSO. The reaction was allowed to proceed for 2 h at 4° C. and quenched by the addition of 500 μL of 1 M Tris buffer (pH 8.0). The mixture was passed through a Sephadex G-25 column (which was eluted with PBS) to remove any free biotin. Labeling with Texas red was carried out in a similar manner.

Library Synthesis.

The cyclic peptide library was synthesized on 2.0 g of TentaGel S $NH_2$ resin (130 μm, ~300 pmol/bead). All of the manipulations were performed at room temperature unless otherwise noted. The linker sequence (ABBFM) was synthesized using 4 equiv of Fmoc-amino acids and HBTU/HOBt/diisopropylethylamine (DIPEA) as the coupling reagents. The coupling reaction was typically allowed to proceed for 1 h, and the beads were washed with DMF (3×) and DCM (3×). The Fmoc group was removed by treatment twice with 20% piperidine in DMF (5+15 min), and the beads were exhaustively washed with DMF (6×). To spatially segregate the beads into outer and inner layers, the resin (after removal of N-terminal Fmoc group) was washed with DMF and water, and soaked in water overnight. The resin was quickly drained and suspended in a solution of Fmoc-OSu (0.26 mmol, 0.50 equiv) and DIPEA (1.2 mmol or 2.0 equiv) in 30 mL of 55:45 (v/v) DCM/diethyl ether. The mixture was incubated on a carousel shaker for 30 min. The beads were washed with 55:45 DCM/diethyl ether (3×) and DMF (8×) to remove water from the beads and then treated with 5 equiv of Boc-Ala-OH, 5 equiv. HBTU/HOBT and 10 equiv. of DIPEA in DMF. Next, the Fmoc group was removed by piperidine treatment and 2 equiv of 4-hydroxymethylbenzoic (HMB) acid and HBTU/HOBt/DIEA (2:2:4 equiv) were added to the resin. Fmoc-β-Ala-OH (5 equiv) was coupled to the HMB linker by using DIC/DMAP (5.5:0.1 equiv), and the coupling was repeated twice to drive the reaction to completion. Then, Fmoc-L-Pra-OH (Pra=propargylglycine), two Fmoc-β-Ala-OH, and Fmoc-L-Glu-OAll were sequentially coupled by standard Fmoc/HBTU chemistry. The Boc protecting group on the encoding peptide was removed by treatment with TFA/water/triisopropylsilane (95:2.5:2.5), and the exposed amine was coupled with Fmoc-Arg(Pbf)-OH. After piperidine treatment, Fmoc-D-Nle-OH was coupled to half of the resin. A few beads were removed before further synthesis. The random region was synthesized by the split-and-pool method with a few modifications as described below. After the first, second and third random positions were coupled, 100 beads, 2 mg and 100 mg of beads, respectively, were removed from the library to generate cyclic peptides of different ring sizes. To ensure complete reaction, each coupling reaction was repeated once. Isobaric amino acids were differentiated by adding 4% (mol/mol) of $CD_3CO_2D$ to the coupling reactions of D-Ala, Abu, Leu, D-Lys, and Orn or 4% $CH_3CD_2CO_2D$ to the D-Nle reaction (Thakkar, A. et al. (2006) Anal. Chem. 78:5935-5939). After the last random residue was added, all of the resin fractions were combined and the allyl group on the C-terminal Glu residue was removed by treatment with a DCM solution containing tetrakis(triphenylphosphine)palladium (0.5 equiv), triphenylphosphine (5 equiv) and N-methylaniline (5 equiv) for 40 min. The N-terminal Fmoc group was then removed with 20% piperidine in DMF (twice for 5+15 min). The beads were washed with DMF (6×), 1 M HOBt in DMF (3×), DMF (3×), and DCM (3×). For peptide cyclization, a solution of PyBOP/HOBt/NMM (5, 5, 10 equiv, respectively) in DMF was mixed with the resin and the mixture was incubated on a carousel shaker for 3 h. The resin was washed with DMF (3×) and DCM (3×) and dried under vacuum for >1 h. Sidechain deprotection was carried out with a modified reagent K (7.5% phenol, 5% water, 5% thioanisole, 2.5% ethanedithiol, 1% anisole, and 1% triisopropylsilane in TFA) for 1 h. The resin was washed with TFA and DCM and dried under vacuum before storage at −20° C.

Library Screening (On-Bead).

The peptide library (1 g) was swollen in DCM, washed exhaustively with DMF, doubly distilled $H_2O$, and buffer A (30 mM sodium phosphate, pH 7.4, 150 mM NaCl, 0.05% Tween 20, and 0.1% gelatin), and incubated overnight at 4° C. in a blocking buffer (buffer A plus 3% BSA). The resin was drained and incubated in the blocking buffer (20 mL) containing 250 nM biotinylated GST-K-Ras for 3 h at 4° C. The unbound protein was removed by washing with buffer A. The resin was resuspended in the blocking buffer (15 mL) and 40 μL of M280 streptavidin-coated Dynabeads was added. The mixture was incubated for 1 h at 4° C. with gentle rotary mixing and the magnetic beads were collected using a TA Dynal MPC-1 magnetic particle concentrator (Invitrogen). The positive beads (~2000 beads) were transferred into a Bio-Spin column (0.8 mL, BioRad) and incubated in 0.8 mL of the blocking buffer containing the SA-AP conjugate (1 μg/mL final concentration) at 4° C. for 10 min. The beads were quickly washed with the blocking buffer (3×1 mL) and a staining buffer (30 mM Tris, pH 8.5, 100 mM NaCl, 5 mM $MgCl_2$, 20 μM $ZnCl_2$) (3×1 mL). The beads were suspended in 1 mL of the staining buffer and 100 μL of a 5-bromo-4-chloro-3-indolyl phosphate (BCIP) stock solution (5 mg/mL) was added. The mixture was incubated at room temperature with rotary mixing and intense turquoise color developed on positive beads in 25 min. The staining reaction was quenched by the addition of 1 M HCl and the most intensely colored beads (389 beads) were manually removed with a micropipette under a dissecting microscope. After exhaustive washing with buffer A, ddH$_2$O, and 8 M guanidine hydrochloride to remove the bound proteins, the beads were incubated overnight at 4° C. with 150 nM Texas red-labeled GST-K-Ras in the blocking buffer in a petri dish. The beads were viewed under an Olympus SZX12 microscope equipped with a fluorescence illuminator (Olympus America, Center Valley, Pa.) and the most intensely colored beads (62 beads) were manually collected.

Library Screening (In-Solution).

The 62 positive beads obtained from on-bead screening were pooled and washed extensively. The beads were soaked in 20 µL of 1:1 (vol/vol) DMF/water mixture and mixed with 10 µL of a freshly made ascorbic acid solution (30 mM) and 10 µL of copper sulfate solution (30 mM). Five µL of 10 mM TMR azide (in DMSO) was added and the mixture was incubated overnight at room temperature and in the dark. The beads were then extensively washed with water/DMF and transferred into individual microcentrifuge tubes (1 bead/tube). The cyclic peptides were cleaved off the beads by treating each bead with 5 µL of 1 M NaOH for 0.5 h. The peptide solution was neutralized with 5.5 µL of 1 M HCl, transferred to a clean tube, and evaporated to dryness under vacuum. The resulting TMR-labeled peptide derived from each bead was dissolved in 30 µL of water to generate a stock solution of ~1 µM for FA analysis. A primary FA analysis was performed by incubating each TMR-labeled cyclic peptide (100 nM) with a single concentration of K-Ras(G12V) (7 µM) in the blocking buffer for 2 h and measuring the FA increase. Any peptides that showed ≥35% FA increase (relative to control without K-Ras protein) were selected for a second round of FA binding analysis (as described below) to determine their dissociation constants ($K_D$ values) for K-Ras. After the above 4 rounds of screening, 25 beads containing cyclic peptides of the highest binding affinities for K-Ras (lowest $K_D$ values) were selected for sequence analysis by partial Edman degradation-mass spectrometry (PED-MS) (Thakkar, A. et al. (2006) Anal. Chem. 78:5935-5939).

Fluorescence Anisotropy.

For cyclic peptides derived from single library beads (library screening), K-Ras protein (non-GST fusion, 0-20 µM) was incubated with the TMR-labeled peptide (50 or 100 nM) in 20 µL of the blocking buffer for 2.5 h at 24° C. The FA values were measured on a Molecular Devices Spectramax M5 spectrofluorimeter, with excitation and emission wavelengths at 545 and 585 nm, respectively. Equilibrium dissociation constants ($K_D$) were determined by plotting the FA values as a function of K-Ras concentration and fitting the data to the equation $$Y = \frac{\left(A_{min} + \left(A_{max} \times \frac{Q_b}{Q_f} - A_{min}\right)\left(\frac{(L+x+K_d) - \sqrt{(L+x+K_d)^2 - 4Lx}}{2L}\right)\right)}{\left(1 + \left(\frac{Q_b}{Q_f} - 1\right)\left(\frac{(L+x+K_d) - \sqrt{(L+x+K_d)^2 - 4Lx}}{2L}\right)\right)}$$

where Y is the measured anisotropy at a given K-Ras concentration x; L is the peptide concentration; Qb/Qf is the correction fact for dye-protein interaction; Amax is the maximum anisotropy at saturating K-Ras concentration; and Amin is the minimum anisotropy. FA analyses with resynthesized FITC-labeled peptides were similarly carried out, except that the excitation and emission wavelengths were at 494 and 520 nm, respectively.

Peptide Sequencing by PED-MS.

Figure 10:
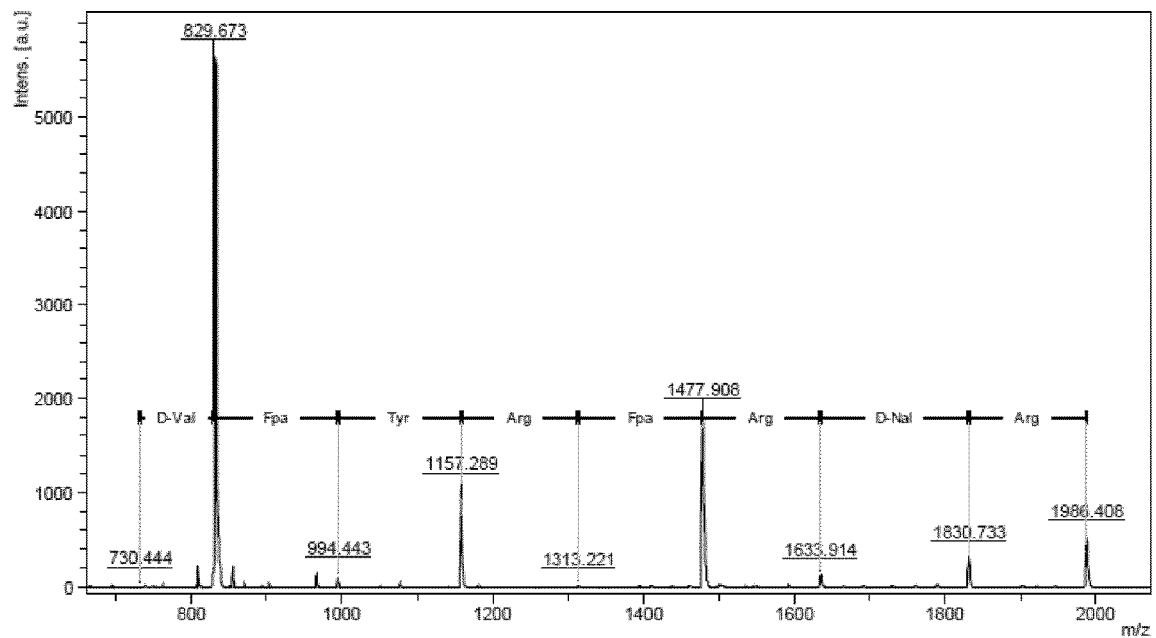
Figure 11:
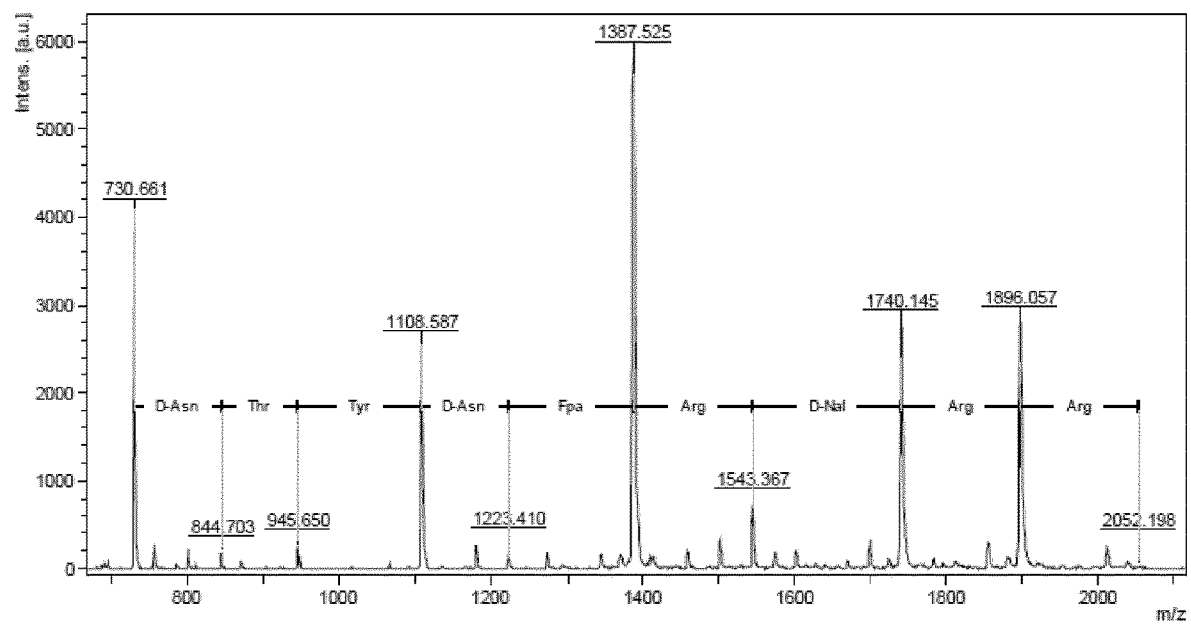
Figure 12:
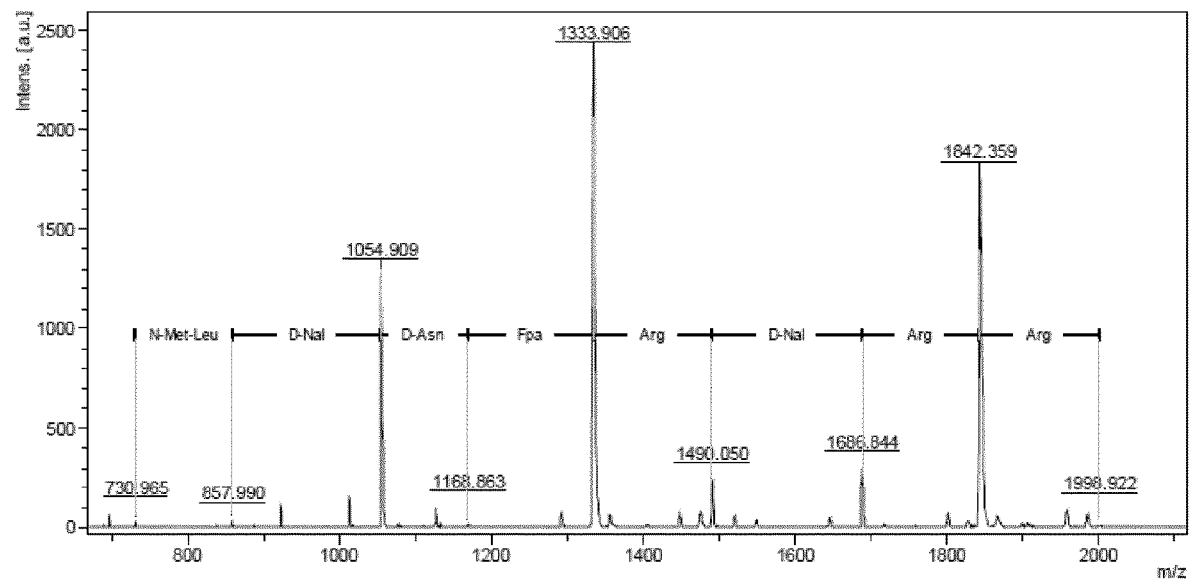
Figure 13:
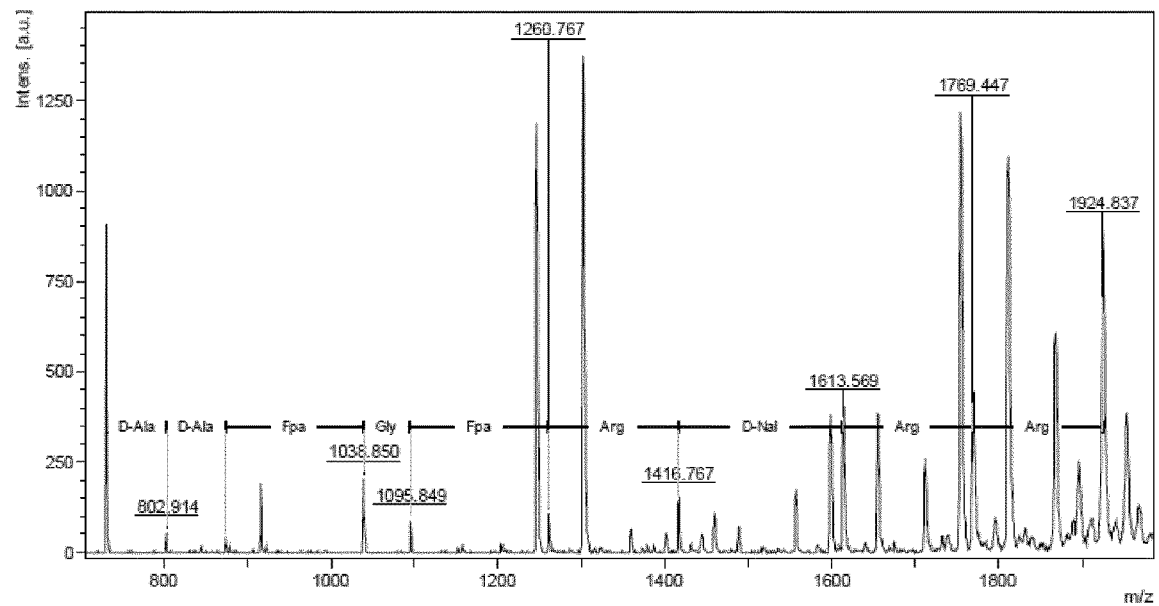
Figure 14:
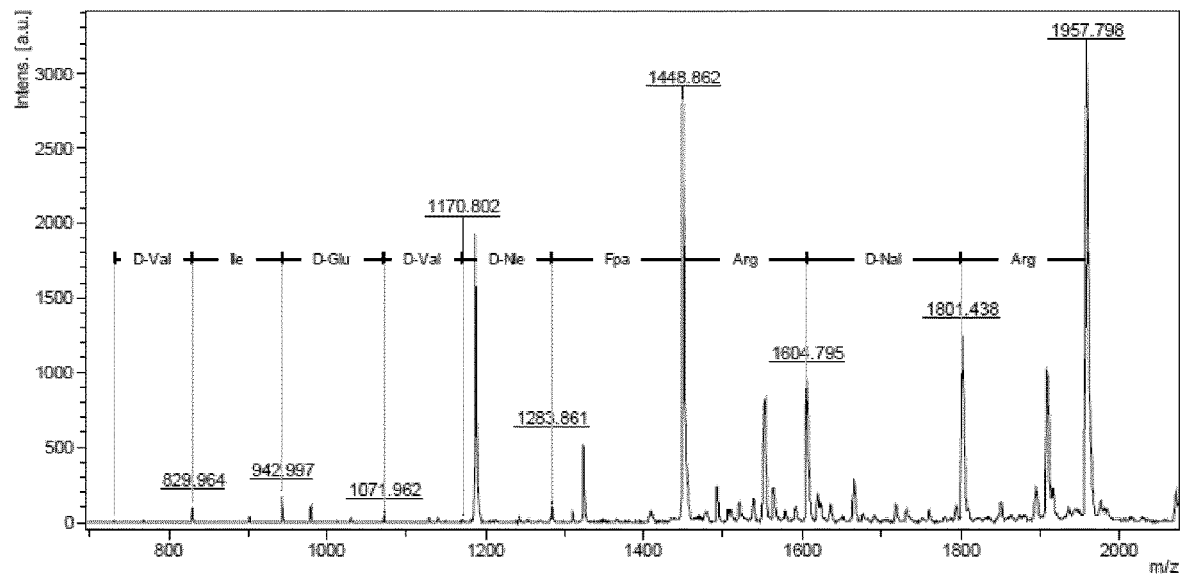
Figure 15:
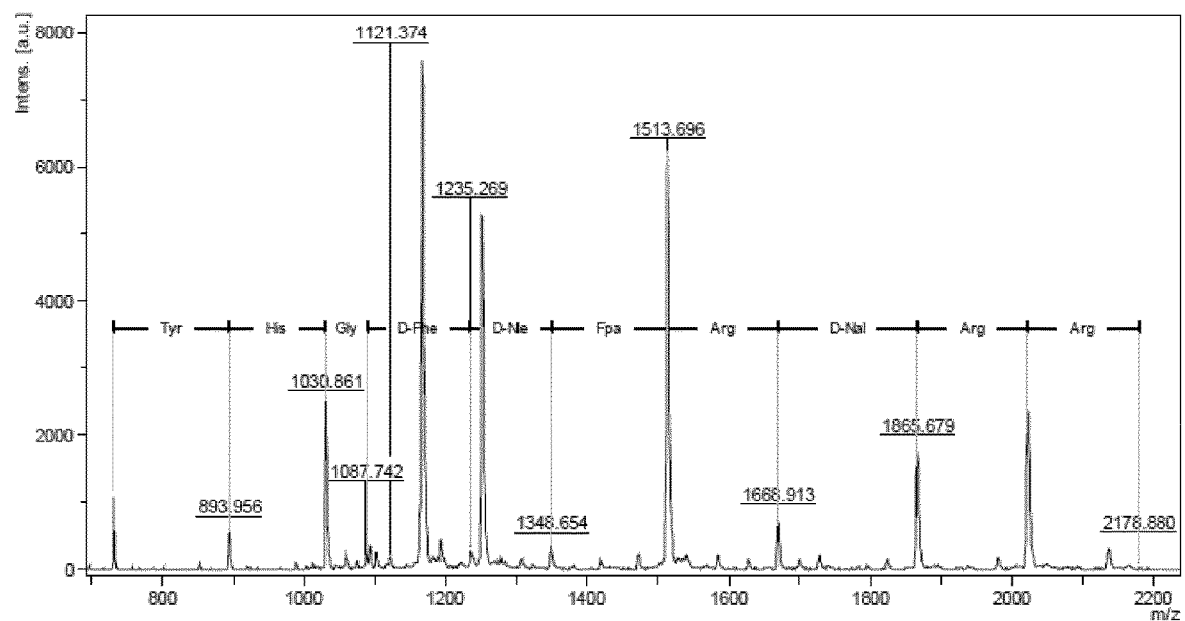
Figure 16:
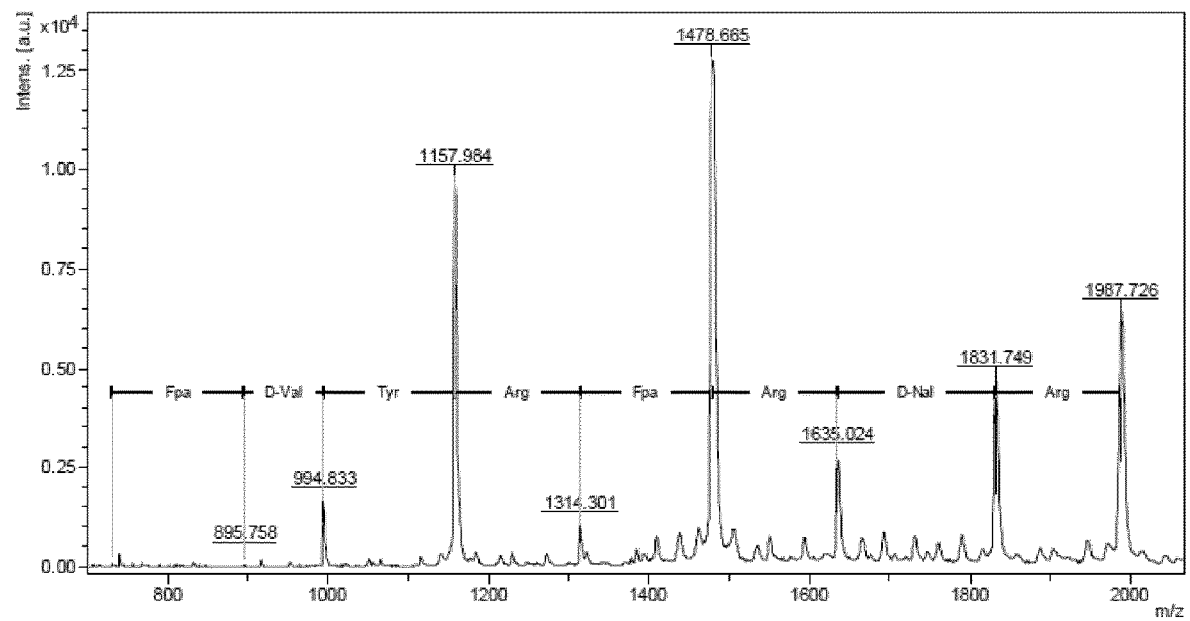
Figure 17:
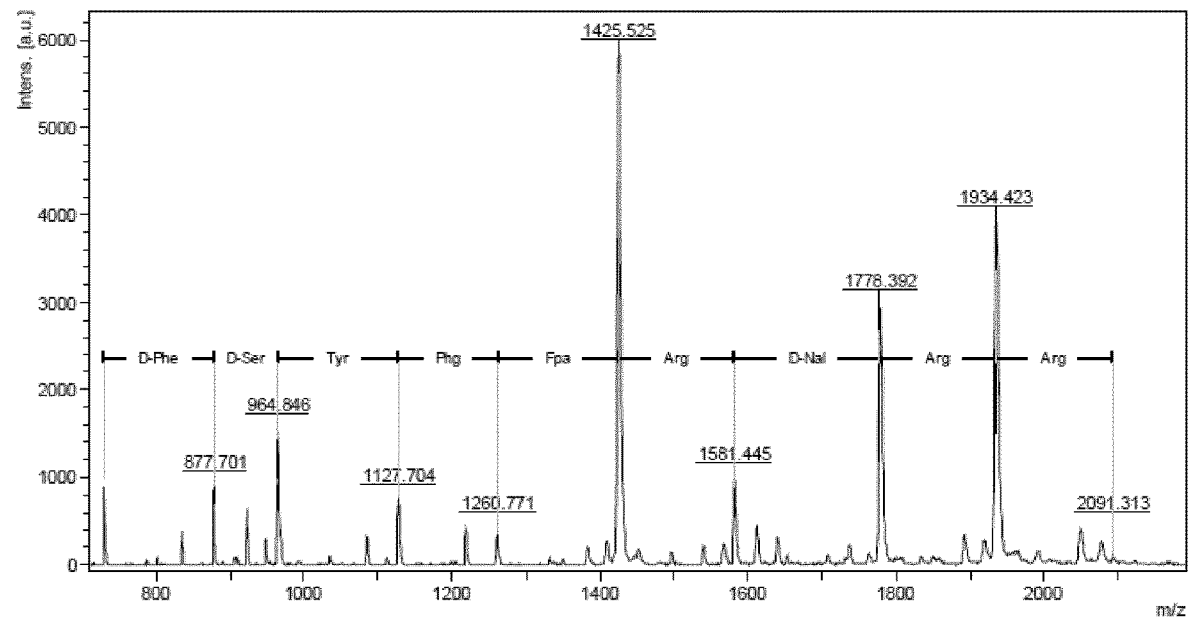
Figure 18:
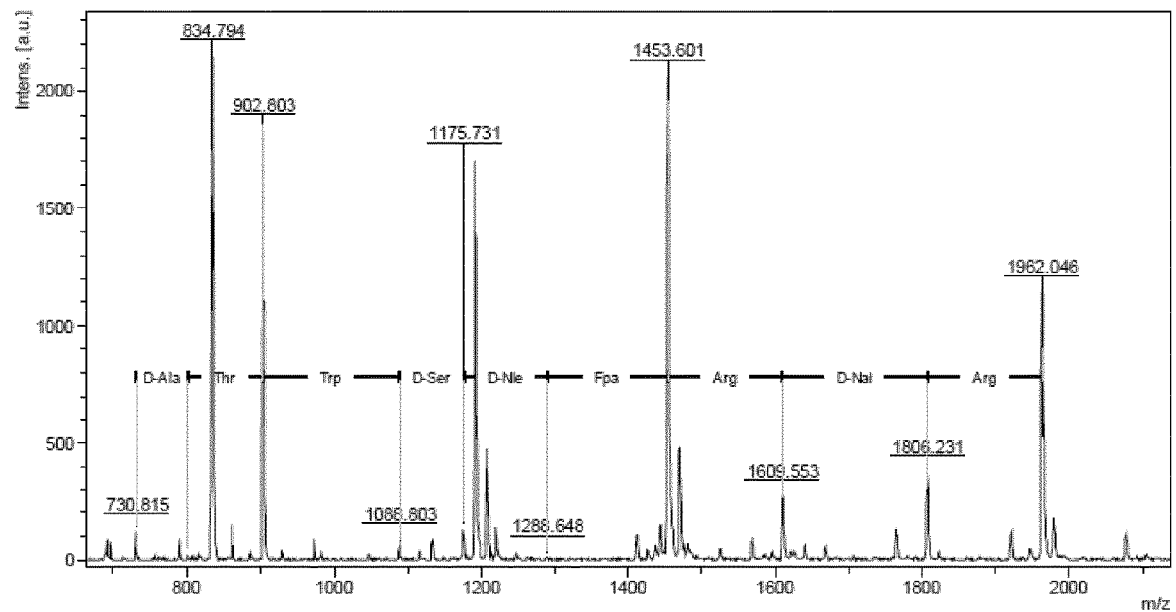
Figure 19:
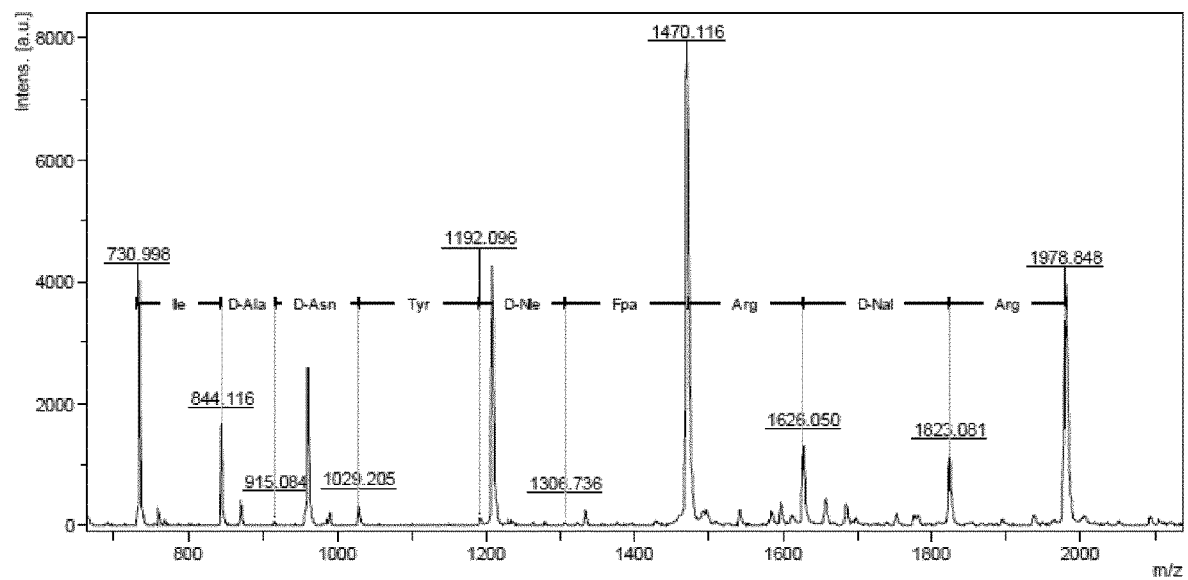
Figure 20:
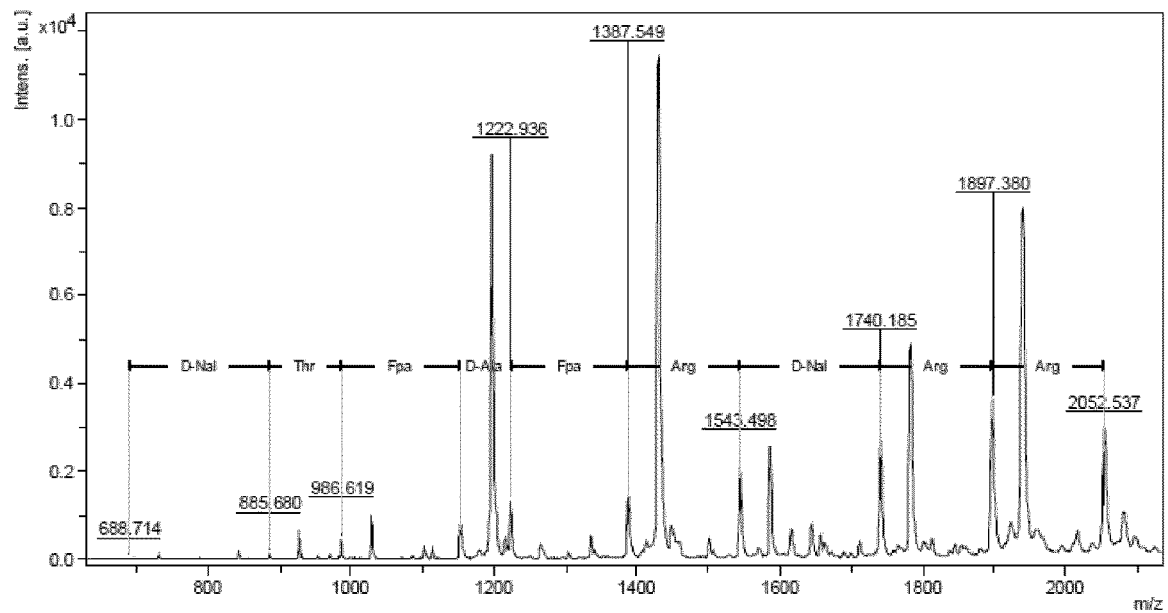
Figure 21:
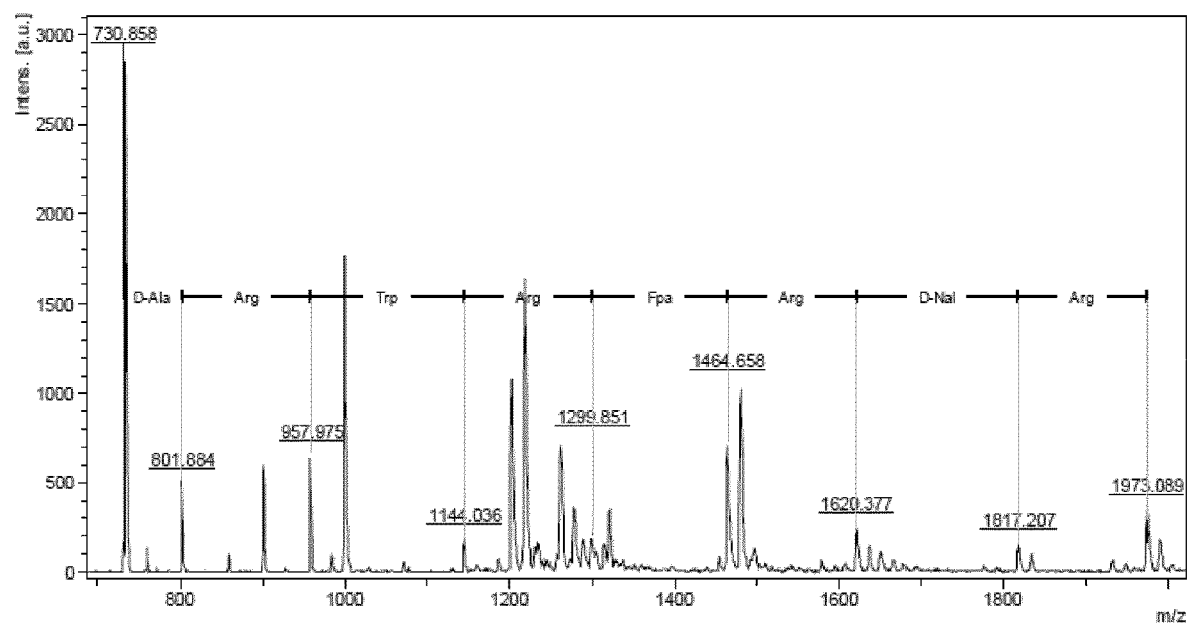
Figure 22:
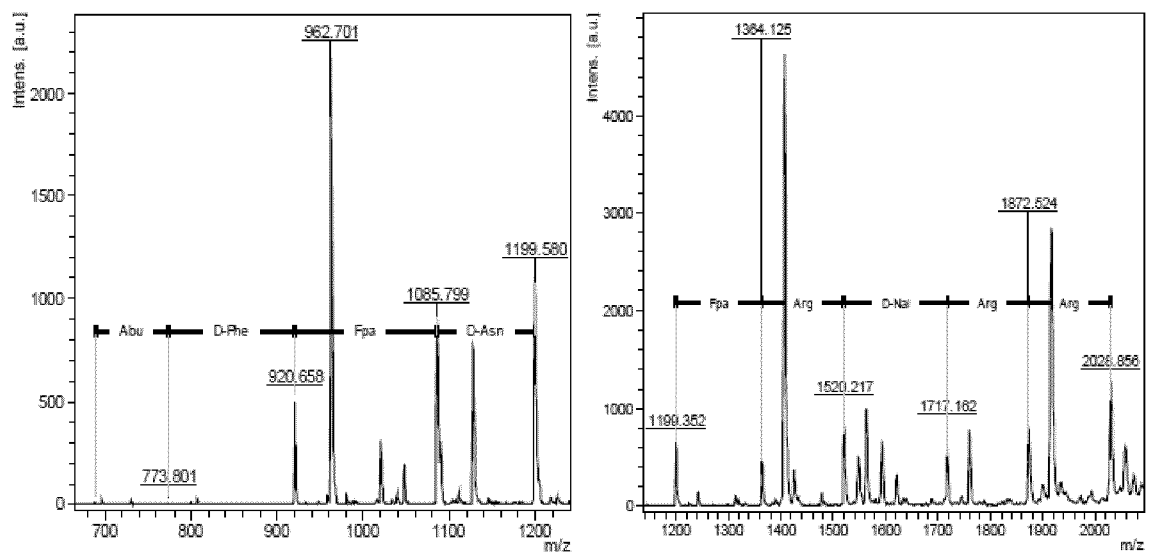

The 25 hit beads containing the linear encoding peptides were divided into two categories on the basis of the $K_D$ values (0-5 µM, 5-11 µM) and subjected to partial Edman degradation in two different reaction vessels. Briefly, 160 µL of pyridine/water (v:v 2:1) containing 0.1% triethylamine was quickly mixed with 160 µL of Fmoc-OSU/PITC (1:80 solution in pyridine) and the resulting mixture was immediately added to each reaction vessel. The reaction was allowed to proceed for 6 min and drained. The beads were washed with pyridine (2×), DCM (3×), and TFA once and incubated with 300 µL of TFA for 6 min twice. The beads were washed with DCM twice and pyridine twice and the PED cycle was repeated 10 times. After the last PED cycle, the N-terminal Fmoc group was removed using 20% piperidine in DMF (300 µL) and the beads were incubated with ammonium iodide (3.0 mg) and dimethylsulfide (30 µL) in TFA (300 µL) for 20 min to reduce any oxidized methionine. The beads were washed with water, transferred to individual microcentrifuge tubes (1 bead/tube), and treated overnight in the dark with 20 µL of CNBr in 70% TFA (40 mg/ml). The released peptides from each bead were dried under vacuum and dissolved in 5 µL of 0.1% TFA in water. One µL of the peptide solution was mixed with 2 µL of a saturated MALDI matrix solution (αCCA) and spotted onto a MALDI sample plate. Mass spectrometry was performed on a Bruker Microflex MALDI-TOF instrument and analyzed by Bruker Baltonics FlexAnalysis 3.3 software (Bruker Daltonic Gmb, Germany). The mass spectra of the 13 positive hits are shown in FIG. 10.

Individual Peptide Synthesis.

Peptides were synthesized on Rink-LS resin (0.28 mmol/g) in a manner similar to that described for the library synthesis. Briefly, Fmoc-lysine(Boc)-OH was coupled onto the Rink resin to provide a side chain amine for later labeling with a fluorescent probe. Fmoc-Glu-O-allyl was added next to provide a cyclization point. Coupling of the remaining residues followed standard Fmoc/HBTU chemistry. After synthesizing the linear peptide, the allyl group on Glu was removed by treatment with Pd(PPh$_3$)$_4$, PPh$_3$, and N-methylaniline (0.5, 5, and 5 equivalents) for 40 min. After removing the N-terminal Fmoc group by piperidine, the peptide was cyclized using PyBOP, HOBT and DIPEA (5, 5, and 10 equivalents) for 2 h after washing the beads extensively with DMF, DCM and 1 M HOBT. The peptides were released from the resin and deprotected by treatment with 94% TFA, 2.5% TIPS, 2.5% H$_2$O and 1% methoxybenzene and purified to homogeneity by reversed-phase HPLC on a C-18 column. Peptide identity was confirmed by MALDI-TOF mass spectrometric analysis. For fluorescent labeling, peptides (~1 mg) were dissolved in 20 µL of DMSO, 30 µL of H$_2$O, and 5 µL of 1 M NaHCO$_3$ and treated with 2 equiv of fluorescein isothiocyanate (Sigma) for 2 h and purified again by reversed-phase HPLC. Unlabeled peptides were similarly synthesized except that Fmoc-Glu-O-allyl was directly coupled to the Rink resin (no lysine linker).

HTRF Assay.

Recombinant HA-tagged K-Ras (no GST, 50 nM), GST-Raf RBD (50 nM each), a monoclonal anti-HA antibody labeled with acceptor d2 (2 µg/mL), a monoclonal anti-GST antibody labeled with donor Tb (0.25 µg/mL) (Cisbio), and increasing concentrations of cyclic peptide (0-20 µM) were mixed inPBS (total volume of 20 µL) in a 384-well plate. The plate was incubated overnight at 4° C. and the HTRF signal was measured on a Molecular Devices Spectramax M5 or a Tecan infinite M1000 Pro plate reader. The data were analyzed by Prism 6.0 from Graphpad Software, Inc. (La Jolla, Calif.) and IC50 values were obtained by fitting the data to dose-response-inhibition curve.

MTT Assay.

MTT assays (17) were performed with H1299 lung cancer cells. One hundred µL of H1299 cells (0.5×105 cells/mL) were seeded in each well of a 96-well culture plate and allowed to grow overnight in Advanced RPMI medium supplemented with 10% fetal bovine serum (FBS) and 1% penicillin-streptomycin. Varying concentrations of cyclic peptide (0-25 µM) were added to the each well and the cells were incubated at 37° C. with 5% $CO_2$ for 72 hours. Ten µL of a MTT stock solution (Roche) was added into each well. The plate was incubated at 37° C. for 4 h. Then 100 µL of SDS-HCl solubilizing buffer was added into each well, and the resulting solution was mixed thoroughly. The plate was incubated at 37° C. overnight. The absorbance of the formazan product was measured at 570 nm using a Molecular Devices Spectramax M5 plate reader. Each experiment was performed in triplicates and the cells without any peptide added were treated as control.

Cellular Activity Against Wildtype Ras

The cell lines H1650 and H1975 express wildtype Ras. These lung cancer cell lines are driven by mutant EGFR which upregulates the MAPK and PI3K signaling pathways via activation of Ras.

Mutant EGFR in H1650 cells can be inhibited with Tarceva® (erlotinib) which is a small molecule EGFR inhibitor. As a result of EGFR inhibition, the MAPK and PI3K signaling pathways are inhibited so that H1650 cells stop proliferating and undergo apoptosis.

In H1975 the EGFR is also mutated. Certain mutated EGFR cannot be inhibited with Tarceva® due to the resistance conferring T790M mutation which precludes binding of the drug. Western Blot experiments demonstrated that the MAPK and PI3K/Akt pathway can be inhibited with 9A5 in both the H1650 and H1975 cell lines. This data suggests that lung cancer cells driven by mutant EGFR may respond to Ras inhibitors. Furthermore, the data suggests that resistance to EGFR inhibitors can be overcome with Ras inhibitors like 9A5.

Pre-Clinical Animal Model

Confirmation of the biological activity of Ras inhibitors is tested in a mouse xenograft model. Two mouse strains, nude mice and SCID mice, are used due to their immunocompromised state and therefor immune rejection of the implanted cells is avoided.

Four to six week old mice are injected with about $3.0 \times 10^6$ cells of the tumor or cancer cells to be tested. The cells can be primary cancer cells or a relevant cell line as noted below. Cells are injected subcutaneously into the lower flank of the mice. Therapy is started when the tumor has reached an average volume of 50-60 mm³ which usually takes 1-3 weeks.

Routes of administration also can be tested and confirmed. If the Ras inhibitor is orally bioavailable, the drug can be administered by oral gavage. Alternatively, the drug may be administered by peritoneal injection or by injection into the tail vein.

Frequency and dose of administration of the drug can be determined. The growth of the tumor in treated and control cohorts will be monitored on a regular basis to demonstrate a therapeutic effect of the compound.

Non-limiting examples of acceptable tumor or cancer cell lines are as follows: Lung Cancer (mutant K-Ras and mutant N-Ras): H1299, H727, H2009, H358, H441. Pancreatic Cancer (mutant K-Ras): YAPC, HPAF-II, PA-TU-8902, Capan-1.

Colon Cancer (mutant K-Ras): CO-115, DLD-1, HCT-116, LS-174T, EB, FRI, IS1, IS3, SW1116, SW480, SW620.

Melanoma (mutant N-Ras): WM1366, WM306, WM3623, WM852, WM3451, WM3629, WM3670.

Cell lines with mutant EGFR to respond to a Ras inhibitor: H1650.

Cell lines with mutant EGFR plus resistance conferring mutation (T790M) for EGFR inhibitors for responsiveness to a Ras inhibitor: H1975.

Colon cancer cell lines with wildtype EGFR and mutant K-Ras for responsiveness to ADC therapy (Ras inhibitor coupled to cetuximab or panitumumab): CO-115, DLD-1, HCT-116, LS-174T, EB, FRI, IS1, IS3, SW1116, SW480, SW620.

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention such as for example, embodiments described in Appendix A attached hereto. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A compound of formula I, II or III

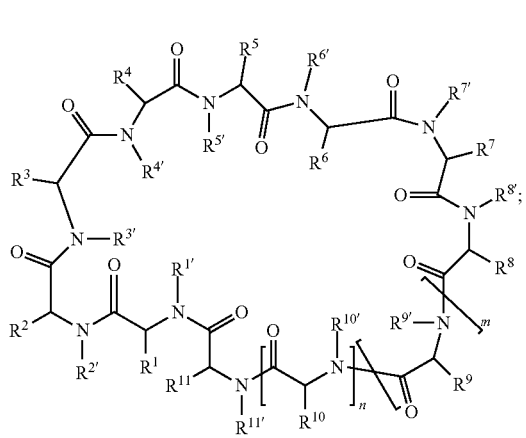

-continued

II

III or a tautomer or a pharmaceutically acceptable salt thereof; wherein
  $R^1$ and $R^2$ are each independently $C_1$-$C_6$ alkyl substituted with NHC(=NH)NH$_2$
  $R^3$ and $R^5$ are independently L-R, wherein L is covalent bond or $C_1$-$C_6$ alkylene, and R is aryl, substituted aryl, heteroaryl or substituted heteroaryl;
  $R^4$, $R^6$, $R^7$, $R^8$, $R^{10}$, $R^{11}$ are each independently H, $C_1$-$C_6$ alkyl, substituted $C_1$-$C_6$ alkyl, phenyl or substituted phenyl,
  $R^9$ is $C_1$-$C_6$ alkyl or $C_1$-$C_6$ alkyl substituted with OH;
  $R^{1'}$, $R^{2'}$, $R^{3'}$, $R^{4'}$, $R^{5'}$, $R^{6'}$, $R^{7'}$, $R^{8'}$, $R^{9'}$, $R^{10'}$ and $R^{11'}$ are independently H or methyl;
  m is 0 or 1; and
  n is 0 or 1.

2. The compound of claim 1, wherein $C_1$-$C_6$ alkyl substituted with $R^{20}$, wherein $R^{20}$ is —NHC(=NH)NH$_2$.

3. The compound of claim 1, wherein:
  a) $R^3$ is —(CH$_2$)$_p$-L$^3$-R$^{23}$, wherein p is 0, 1, 2 or 3, L$^3$ is a covalent bond, and $R^{23}$ is phenyl or naphthyl; or
  b) $R^5$ is —(CH$_2$)$_p$-L$^5$-R$^{25}$, wherein p is 0, 1, 2 or 3, L$^5$ is a covalent bond, and $R^{25}$ is phenyl or pyridyl, wherein the phenyl and pyridyl are optionally substituted with 1 to 3 substituents independently selected from halo, cyano and OH.

4. The compound of claim 1, wherein:
  a) $R^6$ is selected from the group consisting of H, phenyl, $C_1$-$C_6$ alkyl or $C_1$-$C_6$ alkyl substituted with $R^{26}$, wherein $R^{26}$ is selected from the group consisting of NH$_2$, C(O)NH$_2$, NHC(=NH)NH$_2$, and NH-L$^6$-R$^{36}$, wherein L$^6$ is a covalent bond, C(O), C(O)CH=CH, C(O)NH or C(S)NH, and $R^{36}$ is selected from the group consisting of phenyl, pyridyl, or a fluorescent label, wherein the phenyl or pyridyl are optionally substituted with 1 to 3 halo; or
  b) $R^7$ is —(CH$_2$)$_q$-L$^7$-R$^{27}$, wherein q is 0, 1, 2 or 3, L$^7$ is a covalent bond, C(O)NH or NHC(O), and $R^{27}$ is H, OH, C(O)NH$_2$, heteroaryl, phenyl or naphthyl, wherein the heteroaryl, phenyl or naphthyl is optionally substituted with 1 to 3 substituents independently selected from halo and OH; and wherein $R^7$ is optionally selected from the group consisting of —CH$_3$, —CH$_2$Ph, —CH$_2$Ph(4-fluoro), —CH$_2$Ph(4-OH), —CH$_2$OH, —CH$_2$CH$_2$C(O)NH$_2$, —CH$_2$-naphthyl, —CH$_2$CH$_2$C(O)NH$_2$ and —CH$_2$C(O)NH$_2$.

5. The compound of claim 1, wherein $R^8$ is selected from the group consisting of H, phenyl, $C_1$-$C_6$ alkyl or $C_1$-$C_6$ alkyl substituted with $R^{28}$, wherein $R^{28}$ is selected from the group consisting of OH, phenyl, naphthyl, heteroaryl, NH$_2$, NHC(=NH)NH$_2$, and NH-L$^8$-R$^{38}$, wherein the phenyl, naphthyl, and heteroaryl are optionally substituted with 1 to 3 halo or aralkyl; L$^8$ is a covalent bond, C(O), C(O)CH=CH, C(O)NH, NHC(O)CH=CH, or C(S)NH, and $R^{38}$ is selected from the group consisting of H, alkyl, phenyl, pyridyl, or a fluorescent label, wherein the phenyl or pyridyl are optionally substituted with 1 to 3 halo.

6. The compound of claim 5, wherein $R^8$ is selected from the group consisting of H, phenyl, n-butyl, isobutyl, —CH$_2$-indolyl, —(CH$_2$)$_3$NHC(=NH)NH$_2$, —CH$_2$C(O)NH$_2$, —(CH$_2$)$_2$COOH, —CH$_2$OH, —CH(CH$_3$)OH, —(CH$_2$)$_4$NH$_2$, —CH(CH$_3$)OCH$_2$Ph, —CH$_2$Ph, —CH$_2$-naphthyl, —CH(CH$_3$)$_2$, —CH$_2$NH(3-bromo-5-fluorobenzoyl), —CH$_2$NH(6-chloronicotinoyl), —CH$_2$(4-chlorocinnamoyl), —CH$_2$NH (isonicotinoyl), and —CH$_2$NH(3-bromobenzoyl).

7. The compound of claim 1, wherein:
  a) $R^9$ is —(CH$_2$)$_p$-L$^9$-R$^{29}$, wherein p is 0, 1, 2 or 3, L$^9$ is a covalent bond, C(O)NH or NHC(O), and $R^{29}$ is H, OH, aryl or heteroaryl, wherein the aryl or heteroaryl are optionally substituted with 1 to 3 substituents independently selected from halo, cyano and OH; and wherein $R^9$ is optionally selected from the group consisting of $C_1$-$C_3$ alkyl, —C(CH$_3$)$_3$, —CH$_2$OH, and —CH (CH$_3$)OH; or
  b) $R^{29}$ is selected from the group consisting of OH, phenyl, imidazole and pyridyl, and wherein the phenyl, imidazole and pyridyl are optionally substituted with 1 to 3 substituents independently selected from halo, cyano and OH; or
  c) $R^{10}$ is H or $C_1$-$C_6$ alkyl.

8. The compound of claim 1, wherein $R^{11}$ is —(CH$_2$)$_p$—R$^{41}$, wherein p is 0, 1, 2 or 3, and $R^{41}$ is C(O)NH$_2$, NHC(=NH)NH$_2$, C(O)NHR$^{42}$, NHC(=NH)NHR$^{42}$, and wherein $R^{42}$ is an amino acid residue; and wherein $R^{11}$ is optionally —CH$_2$CH$_2$C(O)NH$_2$, —(CH$_2$)$_3$—NHC(=NH)NH$_2$, —CH$_2$CH$_2$C(O)NHR$^{42}$, or —(CH$_2$)$_3$—NHC(=NH)NH—R$^{42}$, wherein $R^{42}$ is a norleucine residue, a lysine residue or an arginine residue.

9. The compound of claim 1, wherein the compound is selected from compound 1A-9A55 in Table 1 or 2 or a pharmaceutically acceptable salt thereof.

10. A composition comprising a compound of claim 1 and a carrier, optionally, a pharmaceutically acceptable carrier.

11. A kit comprising a compound of claim 1 and instructions for use.

12. A compound of formula IB, IIB, IIIB, IVB, VB or VIB:

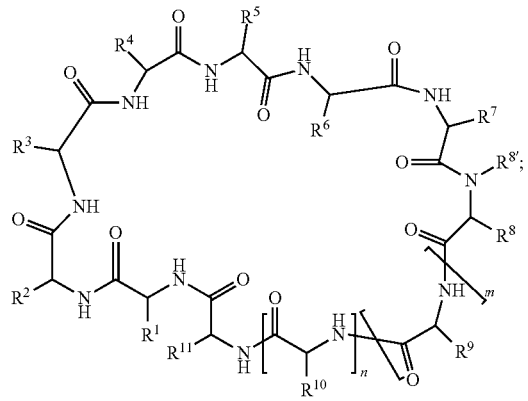

IB

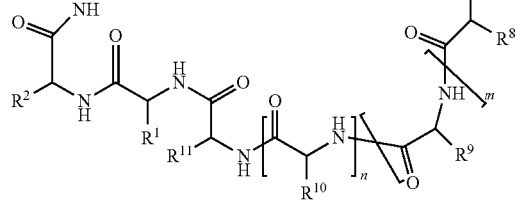

IIB

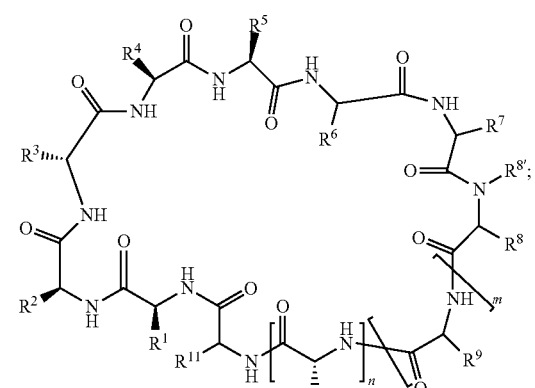

IIIB

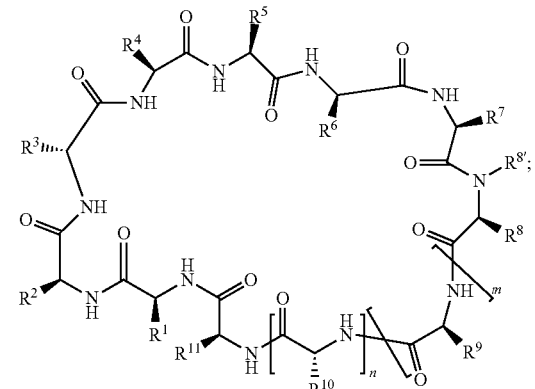

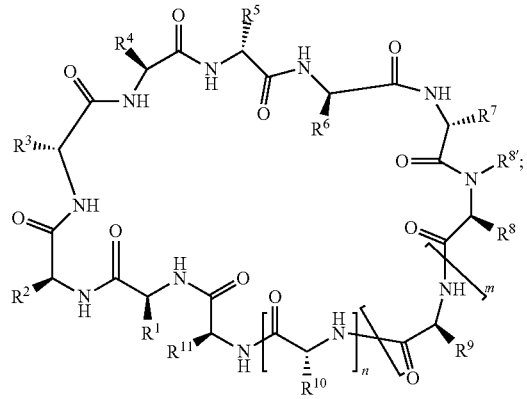

IVB

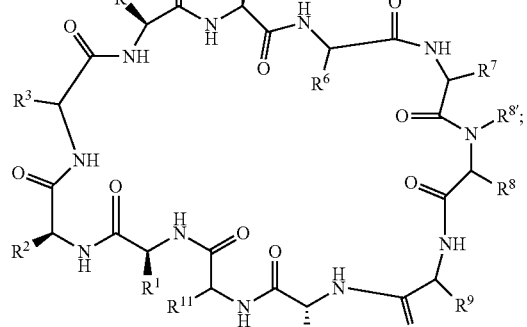

VB

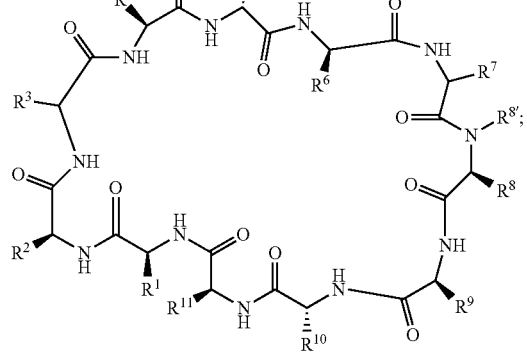

VIB or a tautomer or a pharmaceutically acceptable salt thereof; wherein $R^1$ and $R^2$ are each independently $C_1$-$C_6$ alkyl substituted with $NHC(=NH)NH_2$ $R^3$ and $R^5$ are independently L-R, wherein L is covalent bond or $C_1$-$C_6$ alkylene and R is aryl, substituted aryl, heteroaryl or substituted heteroaryl;

$R^4$, $R^6$, $R^7$, $R^8$, $R^{10}$, $R^{11}$ are each independently H, $C_1$-$C_6$ alkyl, substituted $C_1$-$C_6$ alkyl, phenyl or substituted phenyl, $R^9$ is $C_1$-$C_6$ alkyl or $C_1$-$C_6$ alkyl substituted with OH;
$R^{1'}$, $R^{2'}$, $R^{3'}$, $R^{4'}$, $R^{5'}$, $R^{6'}$, $R^{7'}$, $R^{8'}$, $R^{9'}$, $R^{10'}$ and $R^{11'}$ are independently H or methyl;
m is 0 or 1; and
n is 0 or 1.

* * * * *